(12) United States Patent
Huang et al.

(10) Patent No.: US 10,988,440 B2
(45) Date of Patent: *Apr. 27, 2021

(54) FTO INHIBITORS

(71) Applicant: National Institute of Biological Sciences, Beijing, Beijing (CN)

(72) Inventors: Niu Huang, Beijing (CN); Shiming Peng, Beijing (CN)

(73) Assignee: National Institute of Biological Sciences, Beijing, Beijing (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/740,466

(22) Filed: Jan. 12, 2020

(65) Prior Publication Data
US 2020/0148628 A1    May 14, 2020

Related U.S. Application Data

(63) Continuation of application No. 15/853,653, filed on Dec. 22, 2017, now Pat. No. 10,532,976, which is a
(Continued)

(30) Foreign Application Priority Data

Jun. 23, 2015 (WO) ................ PCT/CN2015/082052
Jun. 20, 2016 (WO) ................ PCT/CN2016/086340
Dec. 22, 2016 (WO) ................ PCT/CN2016/111524

(51) Int. Cl.
| | |
|---|---|
| *C07C 255/34* | (2006.01) |
| *A61P 25/28* | (2006.01) |
| *A61P 3/04* | (2006.01) |
| *C07D 277/30* | (2006.01) |
| *C07D 277/46* | (2006.01) |
| *C07D 213/57* | (2006.01) |
| *C07D 237/14* | (2006.01) |
| *C07D 239/36* | (2006.01) |
| *C07D 241/24* | (2006.01) |
| *C07D 251/16* | (2006.01) |
| *C07D 241/52* | (2006.01) |
| *C07D 471/04* | (2006.01) |
| *C07D 213/80* | (2006.01) |
| *C07D 241/20* | (2006.01) |
| *C07D 285/08* | (2006.01) |
| *C07D 295/185* | (2006.01) |
| *C07D 241/12* | (2006.01) |
| *C07D 249/08* | (2006.01) |
| *C07D 261/12* | (2006.01) |
| *C07D 239/42* | (2006.01) |
| *C07D 215/233* | (2006.01) |
| *C07D 277/56* | (2006.01) |
| *C07D 249/12* | (2006.01) |
| *C07D 211/82* | (2006.01) |
| *C07D 487/04* | (2006.01) |

(Continued)

(52) U.S. Cl.
CPC .............. *C07C 255/34* (2013.01); *A61P 3/04* (2018.01); *A61P 25/28* (2018.01); *C07C 255/43* (2013.01); *C07D 209/08* (2013.01); *C07D 211/82* (2013.01); *C07D 213/57* (2013.01); *C07D 213/75* (2013.01); *C07D 213/80* (2013.01); *C07D 215/233* (2013.01); *C07D 231/14* (2013.01); *C07D 233/56* (2013.01); *C07D 235/08* (2013.01); *C07D 237/14* (2013.01); *C07D 239/26* (2013.01); *C07D 239/36* (2013.01); *C07D 239/42* (2013.01); *C07D 241/12* (2013.01); *C07D 241/20* (2013.01); *C07D 241/24* (2013.01); *C07D 241/52* (2013.01); *C07D 249/08* (2013.01); *C07D 249/12* (2013.01); *C07D 251/16* (2013.01); *C07D 257/04* (2013.01); *C07D 261/08* (2013.01); *C07D 261/12* (2013.01); *C07D 277/24* (2013.01); *C07D 277/30* (2013.01); *C07D 277/46* (2013.01); *C07D 277/56* (2013.01); *C07D 277/64* (2013.01); *C07D 285/08* (2013.01); *C07D 295/185* (2013.01); *C07D 307/46* (2013.01); *C07D 471/04* (2013.01); *C07D 487/04* (2013.01)

(58) Field of Classification Search
CPC ........... C07C 255/34; A61P 25/28; A61P 3/04
USPC ....................................................... 514/653
See application file for complete search history.

(56) References Cited

U.S. PATENT DOCUMENTS 4,963,590 A * 10/1990 Backstrom .............. C07C 59/68
                                                                514/678
10,532,976 B2 * 1/2020 Huang ................. C07D 277/24
(Continued)

FOREIGN PATENT DOCUMENTS

WO    WO-2008119793 A1 * 10/2008 ........... C07C 255/41

OTHER PUBLICATIONS

Lotta; Journal of Computer-Aided Molecular Design, 6 (1992) 253-272. (Year: 1992).*

(Continued)

*Primary Examiner* — Daniel R Carcanague
(74) *Attorney, Agent, or Firm* — Richard Aron Osman

(57) ABSTRACT

The invention provides compounds that inhibit FTO (fat mass and obesity), including pharmaceutically acceptable salts, hydrides and stereoisomers thereof. The compounds are employed in pharmaceutical compositions, and methods of making and use, including treating a person in need thereof, particularly obesity, with an effective amount of the compound or composition, and detecting a resultant improvement in the person's health or condition.

20 Claims, No Drawings

Related U.S. Application Data continuation-in-part of application No. PCT/CN2016/086340, filed on Jun. 20, 2016, which is a continuation-in-part of application No. PCT/CN2015/082052, filed on Jun. 23, 2015, which is a continuation of application No. PCT/CN2016/111524, filed on Dec. 22, 2016.

(51) Int. Cl.
| | |
|---|---|
| *C07D 235/08* | (2006.01) |
| *C07D 231/14* | (2006.01) |
| *C07D 209/08* | (2006.01) |
| *C07D 239/26* | (2006.01) |
| *C07D 233/56* | (2006.01) |
| *C07D 277/24* | (2006.01) |
| *C07D 261/08* | (2006.01) |
| *C07D 307/46* | (2006.01) |
| *C07D 257/04* | (2006.01) |
| *C07D 213/75* | (2006.01) |
| *C07D 277/64* | (2006.01) |
| *C07C 255/43* | (2006.01) |

(56) References Cited

U.S. PATENT DOCUMENTS

2010/0168113 A1* 7/2010 Learmonth .......... C07D 213/26
514/242
2019/0183842 A1* 6/2019 Huang .................. A61K 45/06

OTHER PUBLICATIONS

Taskinen; Quant. Struct.—Act. Relat, 1989, 8, 210-213. (Year: 1989).*
Bonifacio; CNS Drug Reviews, 2007, 13, 352-379. (Year: 2007).*
Di Giovanni; J Biol Chem. 2010, 285, 14941-14954. (Year: 2010).*
Fawcett; Trends in Genetics 2010, 26, 266-274. (Year: 2010).*
Guh; BMC Public Health 2009, 9, 88. (Year: 2009).*
Keller; Journal of Alzheimer's Disease 2011, 23, 461-469. (Year: 2011).*
"Effect of Entacapone on Bodyweight Loss in Obese Population", ClinicalTrials.gov Identifier: NCT02349243 (Jan. 28, 2015). Downloaded from https://clinicaltrials.gov/ct2/show/NCT02349243 on Oct. 17, 2019. (Year: 2015).*
Tervo; Journal of Computer-Aided Molecular Design 17, 797-810, 2003. (Year: 2003).*

* cited by examiner

FTO INHIBITORS

INTRODUCTION

Obesity is a severe health problem worldwide and many factors contribute to this chronic disease, including environmental factors and genetic factors. Genome-wide association studies to investigate patients with obesity revealed a gene for FTO (fat mass and obesity) to strongly associate with obesity. FTO's functional role in obesity was confirmed in transgenic animal models, such as FTO knockout mouse, FTO-overexpression mouse and FTO-I367F mutation mouse. FTO protein is an α-ketoglutarate and iron (II) dependent nucleic acid demethylase. Its preferred substrate is N6-meA in message RNA, which locates near the stop codon and influences gene translation.

We disclosed in US2014/0148383A1 identification of a known FDA approved drug-entacapone as an FTO inhibitor using structure-based virtual screening method in combination with biological activity measurements, including enzymatic activity, cellular activity and in high-fat diet induced obesity (DIO) animal model. Entacapone is a COMT (Catechol-O-methyltransferase) inhibitor used for treating Parkinson disease.

We synthesized numerous derivative and analogs, however activity assays revealed many substitutions reduced or obliterated FTO inhibitory activity, discouraging conventional SAR investigation. Undeterred we pursued a radical derivitization program introducing disruptive functional groups. Here we disclose a novel structural class of FTO inhibitors, composition and methods of use.

EP1978014 discloses processes for preparing entacapone (I) by demethylation of dimethoxy-entacapone (II), wherein II may be prepared by reacting a hydroxyl intermediary (III) with $MHB(OCOR)_3$. This hydroxyl intermediary is coincidentally structurally related to some of the subject compounds.

SUMMARY OF THE INVENTION

The invention provides compounds, compositions and methods for inhibiting FTO and treating disease associated with excess FTO activity, including obesity, obesity-related diseases and Alzheimer's disease. In one aspect the invention provides an FTO inhibitor selected from a compound formula I, a stereoisomer thereof, a hydride thereof, and a pharmaceutically-acceptable salt thereof, or a pharmaceutical composition formulated and suitable for administration to a person and comprising in unit dosage the inhibitor:

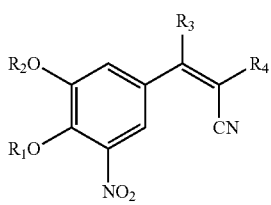

I wherein:
(a)
R1 and R2 are independently H or Me;
R3 is OH or NHR, wherein R is H or an optionally substituted, optionally hetero-, optionally cyclic C1-C18 hydrocarbyl; and
R4 is optionally substituted, optionally hetero-, optionally cyclic C1-C18 hydrocarbyl;
(b)
R1 and R2 are independently H or Me;
R3 is H, OH or NHR, wherein R is H or C1-C4 alkyl, esp. Me;
R4 is CONHR5; and
R5 is optionally substituted, optionally hetero-, optionally cyclic C1-C18 hydrocarbyl;
(c)
R1 and R2 are independently H or Me;
R3 is H, OH or NHR, wherein R is H or C1-C4 alkyl, esp. Me;
R4 is COR5; and
R5 is optionally substituted, heterocyclic C3-C18 hydrocarbyl comprising an n-membered ring wherein n=3-18 (3, 4, 5, 6, 9 or 10) including 1 to n−1 heteroatoms independently selected from N, O, S and P; or
(d)
R1 and R2 are independently H or Me;
R3 is H, OH or NHR, wherein R is H or C1-C4 alkyl, esp. Me; and
R4 is optionally substituted, heterocyclic C3-C18 hydrocarbyl comprising an n-membered ring wherein n=3-18 (3, 4, 5, 6, 9 or 10) including 1 to n−1 heteroatoms independently selected from N, O, S and P;
wherein excluded from the inhibitor, unless present in the composition, are compounds identified by CAS ID number: 309, CAS ID: 1364322-41-7; 365, CAS ID:1150310-12-5; 371, CAS ID: 1150310-15-8; and
361, CAS ID: 143542-72-7, such as if R3 is diethylamide and R4 is OH then one or both R1 and R2 is H.

In embodiments of the inhibitor or composition the heterocyclic C3-C18 hydrocarbyl comprises:
a 3 membered ring that is an optionally substituted: aziridine, oxirane, oxaziridine;
a 4 membered ring that is an optionally substituted: azetidine, oxetane, oxazetidine;
a 5 membered ring that is an optionally substituted: pyrrole, 1,2-diazole (pyrazole), 1,3 diazole (imidazole), thiazole, isothiazole, oxazole, isoxazole, furan, dioxole, thiophene;
a 6 membered ring that is an optionally substituted: pyridine, diazine, triazine, oxazine, thiazine, dioxine, oxathiine, dithiine;
a 9 membered ring that is an optionally substituted: indole, benzothiazole, benzooxazole, benzofuran, benzodioxole, benzothiophene, benzodithiole; or
a 10 membered ring that is an optionally substituted: quinoline, quinoxaline, quinazoline, chromene, benzodioxine, thiochromene, benzodithiine.

In embodiments of the inhibitor or composition the optionally substituted, optionally hetero-, optionally cyclic $C_1$-$C_{18}$ hydrocarbyl in each instance is an optionally substituted C1-C9 alkyl, C2-C9 alkenyl, C2-C9 alkynyl, or C5-C14 aryl hydrocarbon, comprising 1-5 heteroatoms that are N, S, O or P, including 1-5 nitrogen atoms, or a heteroatom substituted with the hydrocarbon.

In embodiments of the inhibitor or composition:
one or both R1 and R2 is H;
R3 is OH; and/or
R is H or C1-C4 alkyl, esp. Me.

In an aspect the inventors surprising and unexpectedly found that the compounds disclosed herein wherein $R_3$ is OH demonstrated a much longer $T_{1/2}$ and a lower $Cl_{int}$ compared with entacapone, and that the introduction of hydroxyl imparts better inhibitory activity of FTO receptor over COMT receptor.

In another aspect the FTO inhibitor is a compound of formula I, supra, or a stereoisomer thereof, a hydride thereof, or a pharmaceutically-acceptable salt thereof, wherein:

$R_1$ and $R_2$ are each independently H or $C_{1-4}$alkyl;

$R_3$ is OH or NHR, wherein R is hydrogen, —$C_{1-4}$alkyl, cycloalkyl, heterocyclyl, aryl or heteroaryl;

$R_4$ is hydrogen, —$C_{1-6}$alkyl, —$C_{2-6}$alkenyl, —$C_{2-6}$alkynyl, cycloalkyl, heterocyclyl, aryl, heteroaryl, —$SO_2R_a$, —$COR_a$, —$CO_2R_a$, —$CONR_aR_b$, $NR_aR_b$, —$NR_aCOR_b$, —$NR_aCO_2R_b$, or —$NR_aSO_2R_b$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_c$;

wherein $R_a$ and $R_b$ are each independently hydrogen, $C_{1-4}$alkyl, heteroaryl$C_{1-4}$alkyl-, heterocyclyl$C_{1-4}$alkyl-, aryl, heteroaryl, or $C_{3-6}$cycloalkyl; or $R_a$ and $R_b$, together with the atom(s) to which they are attached form a 3- or 4- or 5- or 6-membered ring optionally comprising an additional heteroatom selected from the group of O, NH, S and P; and $R_c$ is hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, oxo, —OH, $C_{1-6}$alkyloxy, —$SO_2H$, $C_{1-6}$alkylSO$_2$-, —COH, $C_{1-6}$alkylCO—, $CO_2H$, $C_{1-6}$alkylCO$_2$-, $CONH_2$ or —$NH_2$, provided that said compound is not (Z)-2-cyano-3-(3,4-dimethoxy-5-nitrophenyl)-N,N-diethyl-3-hydroxyacrylamide.

In another embodiment, the FTO inhibitor is a compound of formula I, supra, or a stereoisomer thereof, a hydride thereof, or a pharmaceutically-acceptable salt thereof, wherein:

$R_1$ and $R_2$ are each independently H or $C_{1-4}$alkyl;

$R_3$ is OH;

$R_4$ is heteroaryl, —$COR_a$, or —$CONR_aR_b$; wherein said heteroaryl is optionally substituted with at least one substituent $R_c$;

wherein $R_a$ and $R_b$ are each independently hydrogen, $C_{1-4}$alkyl, heteroaryl$C_{1-4}$alkyl-, heterocyclyl$C_{1-4}$alkyl-, aryl, heteroaryl, or $C_{3-6}$cycloalkyl; or $R_a$ and $R_b$, together with the nitrogen atom to which they are attached form a 3- or 4- or 5- or 6-membered monocyclic ring optionally comprising an additional heteroatom selected from the group of O, NH, S and P; and $R_c$ is hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, oxo, —OH, $C_{1-6}$alkyloxy, —$SO_2H$, $C_{1-6}$alkylSO$_2$-, —COH, $C_{1-6}$alkylCO—, $CO_2H$, $C_{1-6}$alkylCO$_2$-, $CONH_2$ or —$NH_2$, provided that said compound is not (Z)-2-cyano-3-(3,4-dimethoxy-5-nitrophenyl)-N,N-diethyl-3-hydroxyacrylamide.

In particular embodiments, $R_1$ and $R_2$ are each H; one of $R_1$ and $R_2$ is H, the other is $C_{1-4}$alkyl, preferably methyl; or $R_1$ and $R_2$ are each $C_{1-4}$alkyl, preferably methyl.

In particular embodiments, $R_4$ is —$COR_a$, wherein $R_a$ is heteroaryl, wherein preferably $R_a$ is a 5-membered heteroaryl comprising one nitrogen atom and one sulfur atom, preferably, $R_a$ is thiazolyl, e.g., thiazole-4-yl.

In embodiments $R_4$ is —$CONR_aR_b$, $R_a$ and $R_b$ are each independently hydrogen, $C_{1-4}$alkyl, heteroaryl$C_{1-4}$alkyl-, heterocyclyl$C_{1-4}$alkyl-, heteroaryl, or $C_{3-6}$cycloalkyl, wherein preferably, $R_a$ and $R_b$ are both $C_{1-4}$alkyl; more preferably, $R_a$ and $R_b$ are both ethyl. Alternatively, one of $R_a$ and $R_b$ is hydrogen, the other is $C_{1-4}$alkyl, heteroaryl$C_{1-4}$alkyl-, heterocyclyl$C_{1-4}$alkyl-, heteroaryl or $C_{3-6}$cycloalkyl; preferably, one of $R_a$ and $R_b$ is hydrogen, the other is $C_{1-4}$alkyl, pyrimidinyl$C_{1-4}$alkyl- (e.g., pyrimidin-4-ylmethyl), 5- to 10-membered heteroaryl (e.g., pyridinyl, pyrizinyl, pyrimidinyl, thiazolyl, benzo[d]thiazolyl, thiadiazolyl), or $C_{3-6}$cycloalkyl (e.g., cyclopropyl, cyclobutyl, cyclopentyl or cyclohexyl). Alternatively, $R_a$ and $R_b$, together with the nitrogen atom to which they are attached form a 3- or 4- or 5- or 6-membered monocyclic ring optionally comprising an additional heteroatom selected from the group of O, NH, and S; $R_a$ and $R_b$, together with the nitrogen atom to which they are attached form a 3- or 4- or 5- or 6-membered monocyclic ring optionally comprising one additional oxygen atom. Preferably, $R_a$ and $R_b$, together with the nitrogen atom to which they are attached form a 4- or 6-membered monocyclic ring optionally comprising one additional oxygen atom. More preferably, $R_a$ and $R_b$, together with the nitrogen atom to which they are attached form a 4-membered monocyclic ring, or a 6-membered monocyclic ring or a 6-membered monocyclic ring comprising one additional oxygen atom. Most preferably, $R_a$ and $R_b$, together with the nitrogen atom to which they are attached form a piperidinyl, azetidinyl or 1,3-oxazinanyl.

In embodiments, $R_4$ is heteroaryl optionally substituted with at least one substituent $R_c$, wherein $R_c$ is as defined above; wherein peferably, $R_4$ is a 5- or 6-membered monocyclic heteroaryl comprising one or two or three or four heteroatoms selected from NH, O, S and P (preferably 5- or 6-membered monocyclic heteroaryl comprising one or two or three or four heteroatoms selected from NH, O and S); or a 9 or 10-membered bicylic heteroaryl comprising one or two or three or four heteroatoms selected from NH, O, S and P (preferably, a 9 or 10-membered bicylic heteroaryl comprising one or two or three or four heteroatoms selected from NH, O and S). More preferably, $R_4$ is pyridinyl, pyrizinyl optionally substituted by carboxyl, pyrimidinyl, thiazolyl, benzo[d]thiazolyl, or 1,2,4-thiadiazolyl. Most preferably, $R_4$ is pyridin-2-yl, pyrizin-2-yl optionally substituted by carboxyl, pyrimidin-4-yl, thiazol-2-yl, benzo[d]thiazol-2-yl, or 1,2,4-thiadiazol-5-yl.

In embodiments the inhibitor is of the following Tables. We measured compound inhibition activity in a demethylation reaction catalyzed by FTO (US2014/0148383A1). The reaction system was incubated at 37° C. for 2 h and stopped by heating at 95° C. for 5 min. ssDNA was digested by nuclease P1 and alkaline phosphatase. The concentrations of N6-mA and A were analyzed by HPLC-MS/MS. When concentration of substrate and enzyme are 0.5 μM and 0.1 μM, respectively, the measured IC50 value of entacapone against FTO is ~3 μM.

TABLE 1

Subsection (a) inhibitors, wherein R3 is OH, demonstrating IC50 value <10 μM in demethylation reaction catalyzed by FTO; experimental details below.

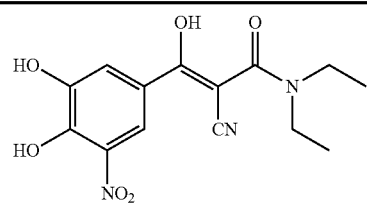

347

TABLE 1-continued
Subsection (a) inhibitors, wherein R3 is OH, demonstrating IC50 value <10 μM in demethylation reaction catalyzed by FTO; experimental details below.
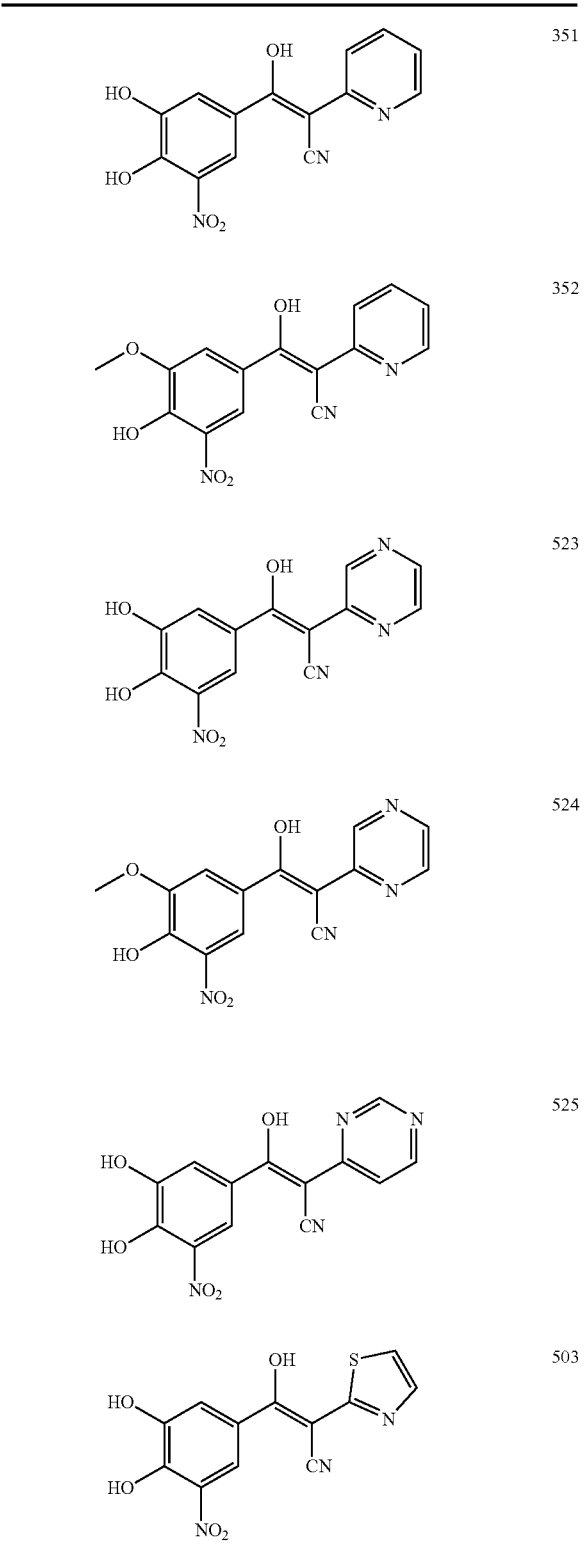
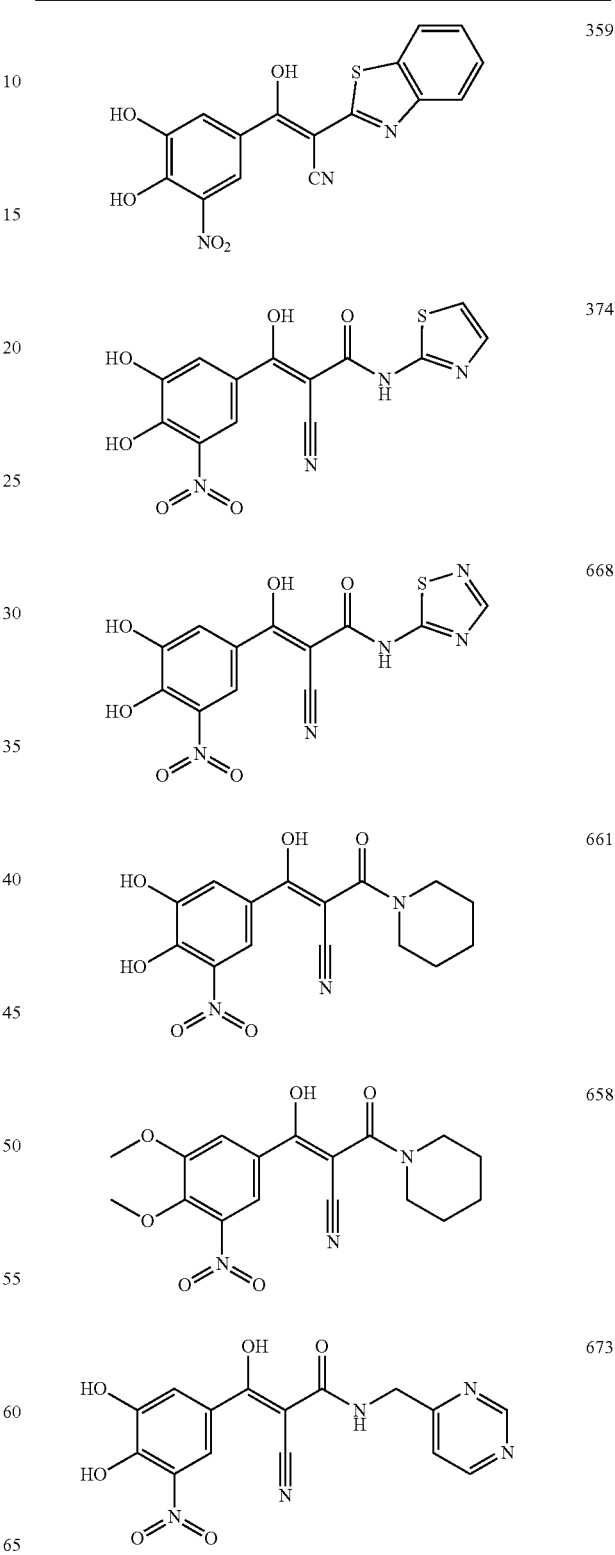

TABLE 1-continued

Subsection (a) inhibitors, wherein R3 is OH, demonstrating IC50 value <10 μM in demethylation reaction catalyzed by FTO; experimental details below.

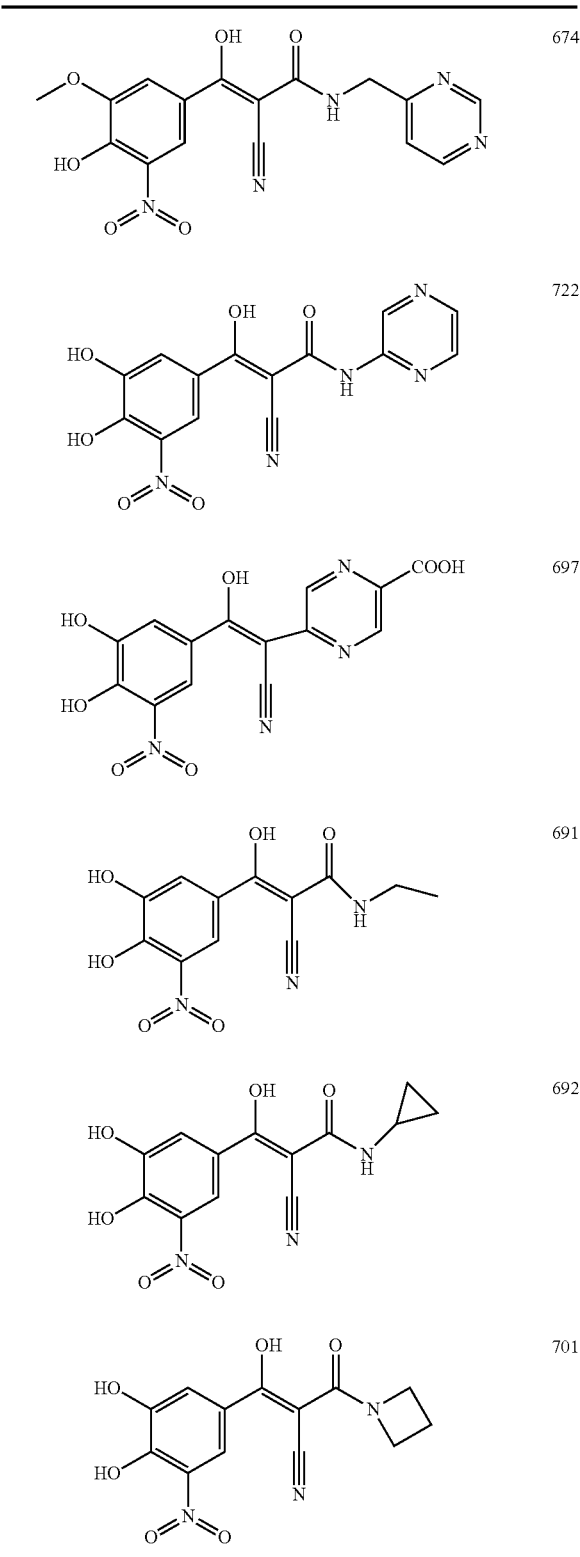

TABLE 1-continued

Subsection (a) inhibitors, wherein R3 is OH, demonstrating IC50 value <10 μM in demethylation reaction catalyzed by FTO; experimental details below.

TABLE 2

Subsection (a) inhibitors, wherein R3 is NHR, demonstrating IC50 value <10 μM in demethylation reaction catalyzed by FTO; experimental details below.

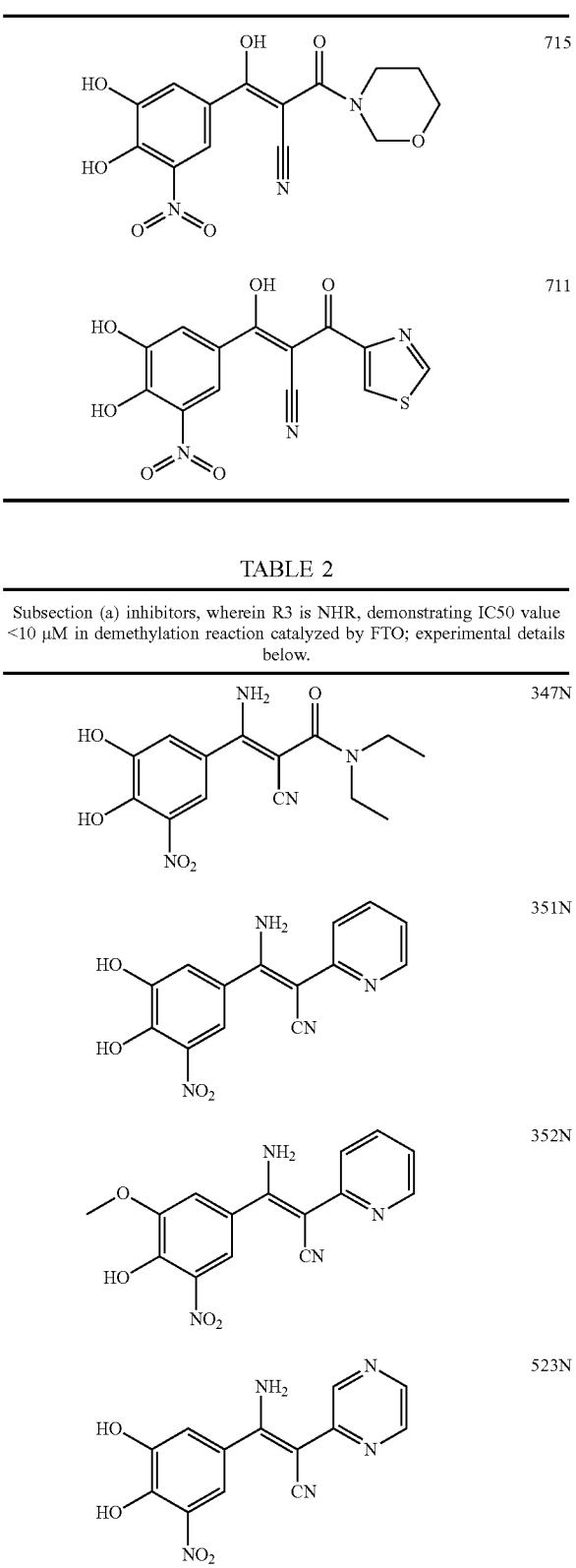

TABLE 2-continued
Subsection (a) inhibitors, wherein R3 is NHR, demonstrating IC50 value <10 μM in demethylation reaction catalyzed by FTO; experimental details below.
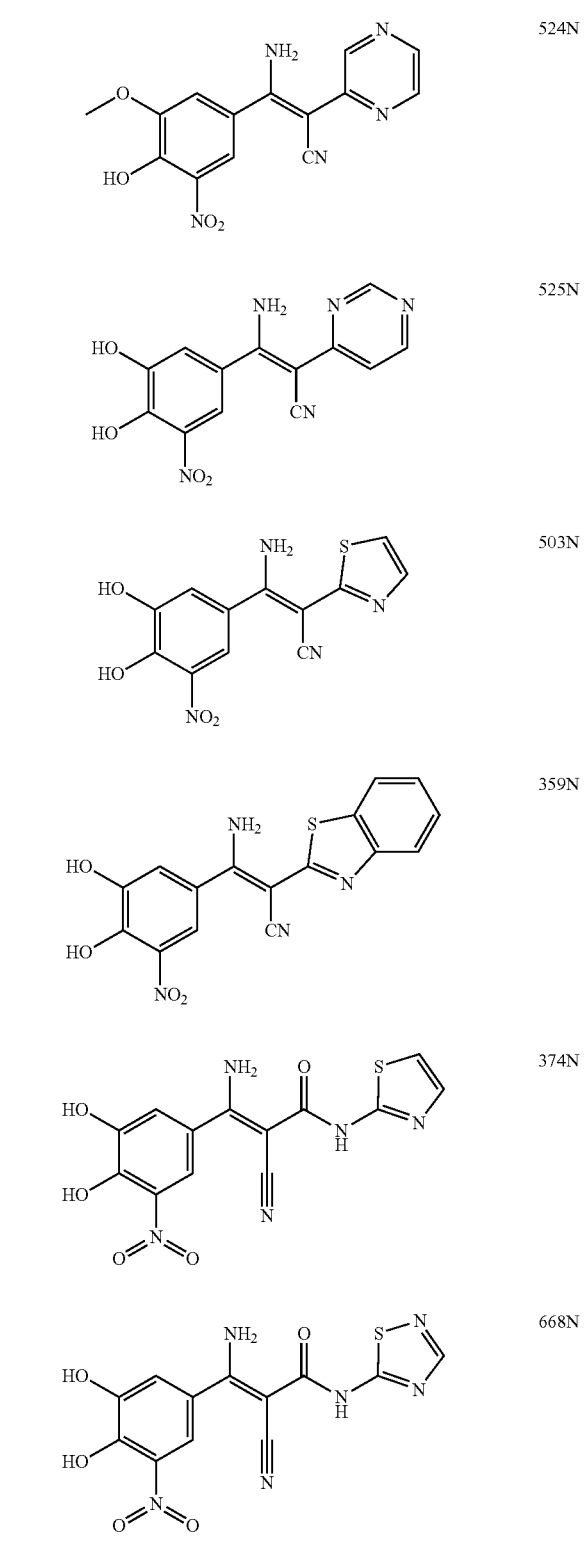
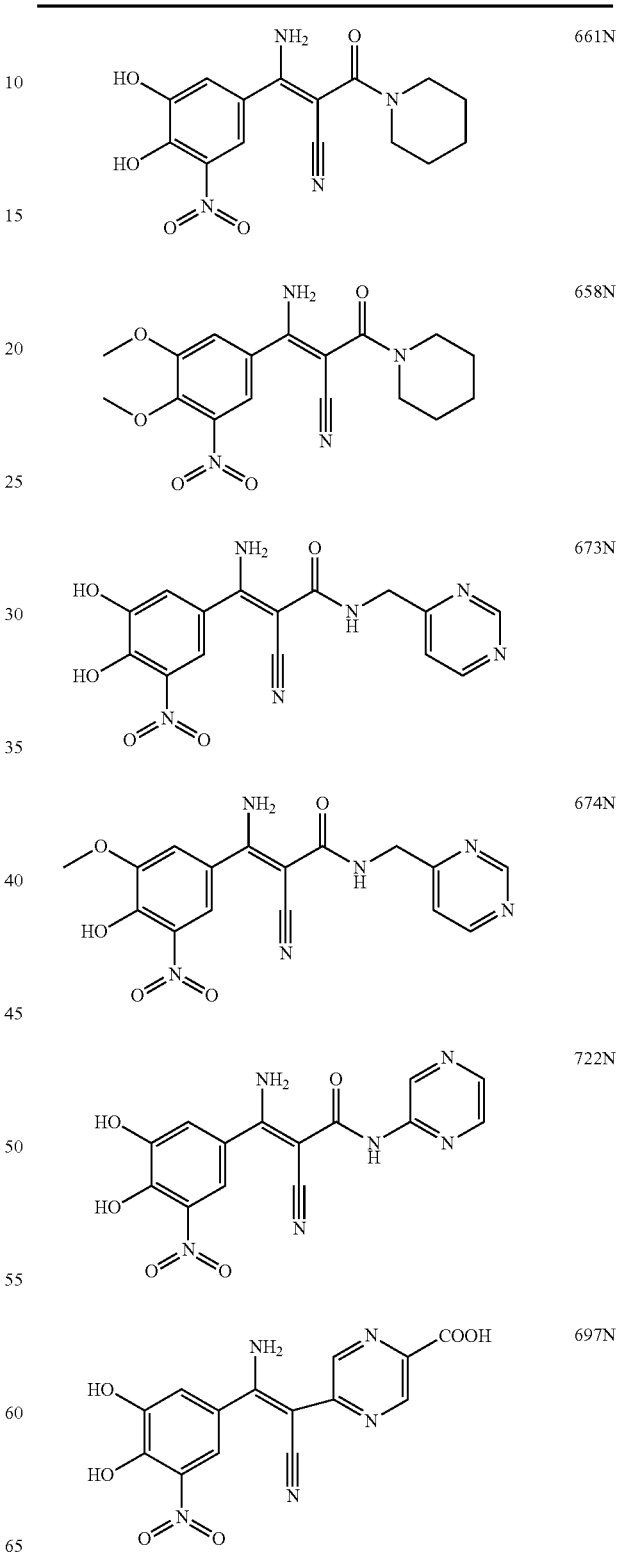

TABLE 2-continued

Subsection (a) inhibitors, wherein R3 is NHR, demonstrating IC50 value <10 µM in demethylation reaction catalyzed by FTO; experimental details below.

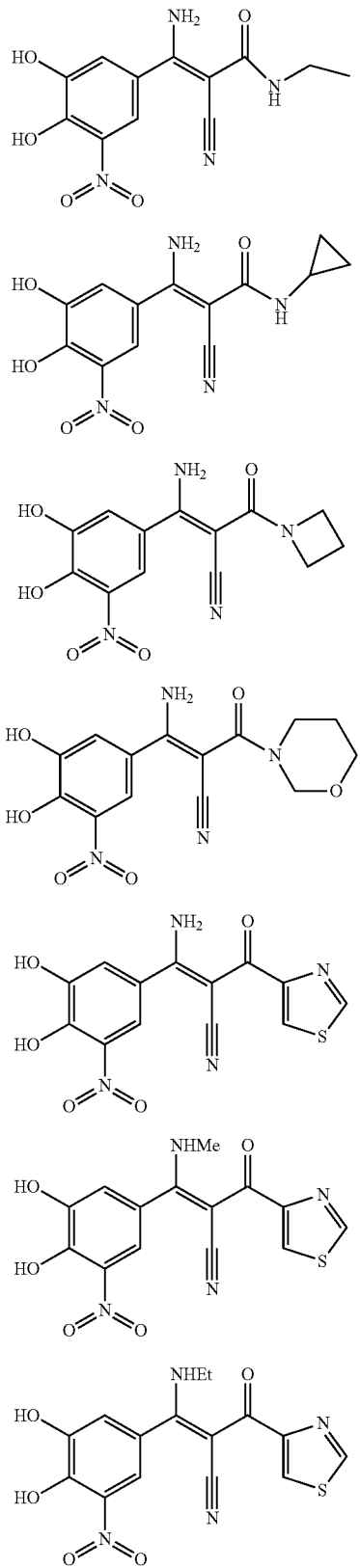

TABLE 2-continued

Subsection (a) inhibitors, wherein R3 is NHR, demonstrating IC50 value <10 µM in demethylation reaction catalyzed by FTO; experimental details below.

TABLE 3

Subsection (b) inhibitors, wherein R4 is CONHR5, demonstrating IC50 value <10 µM in demethylation reaction catalyzed by FTO; experimental details below.

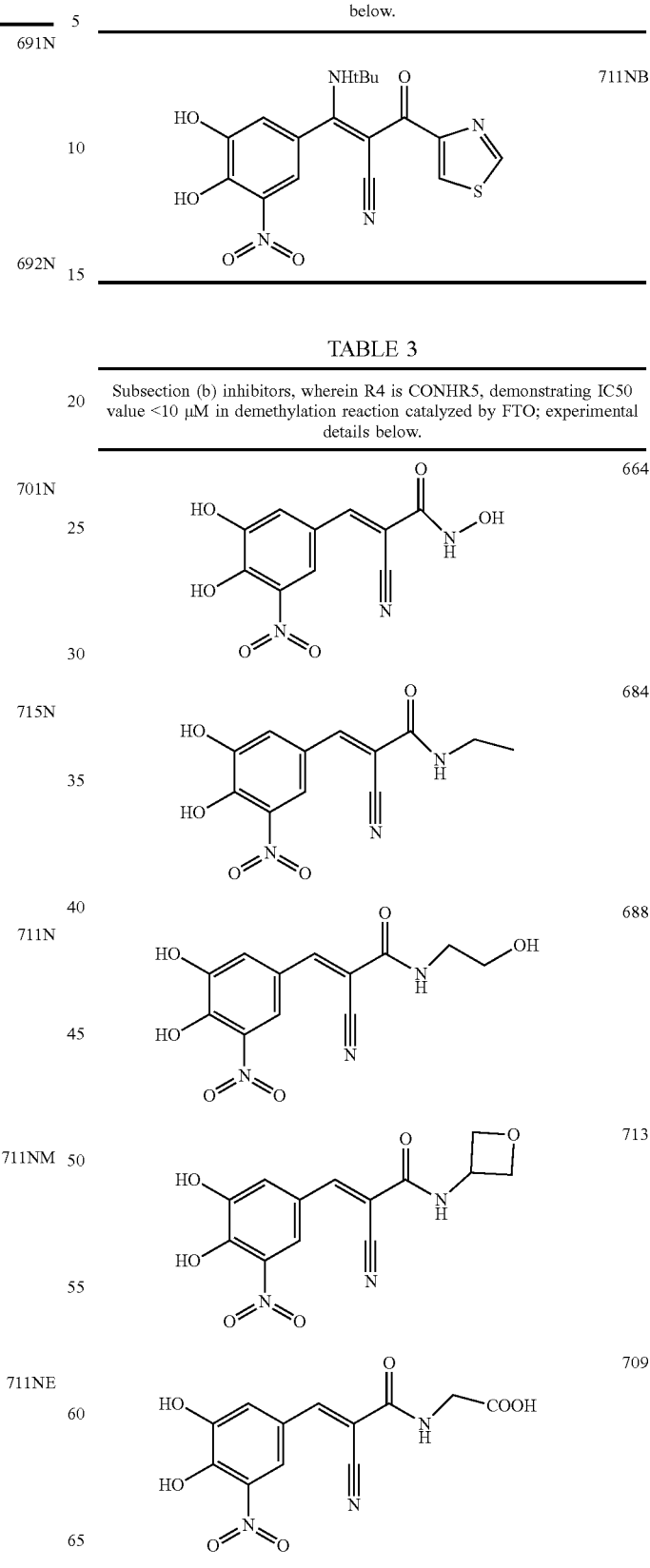

TABLE 3-continued
Subsection (b) inhibitors, wherein R4 is CONHR5, demonstrating IC50 value <10 µM in demethylation reaction catalyzed by FTO; experimental details below.
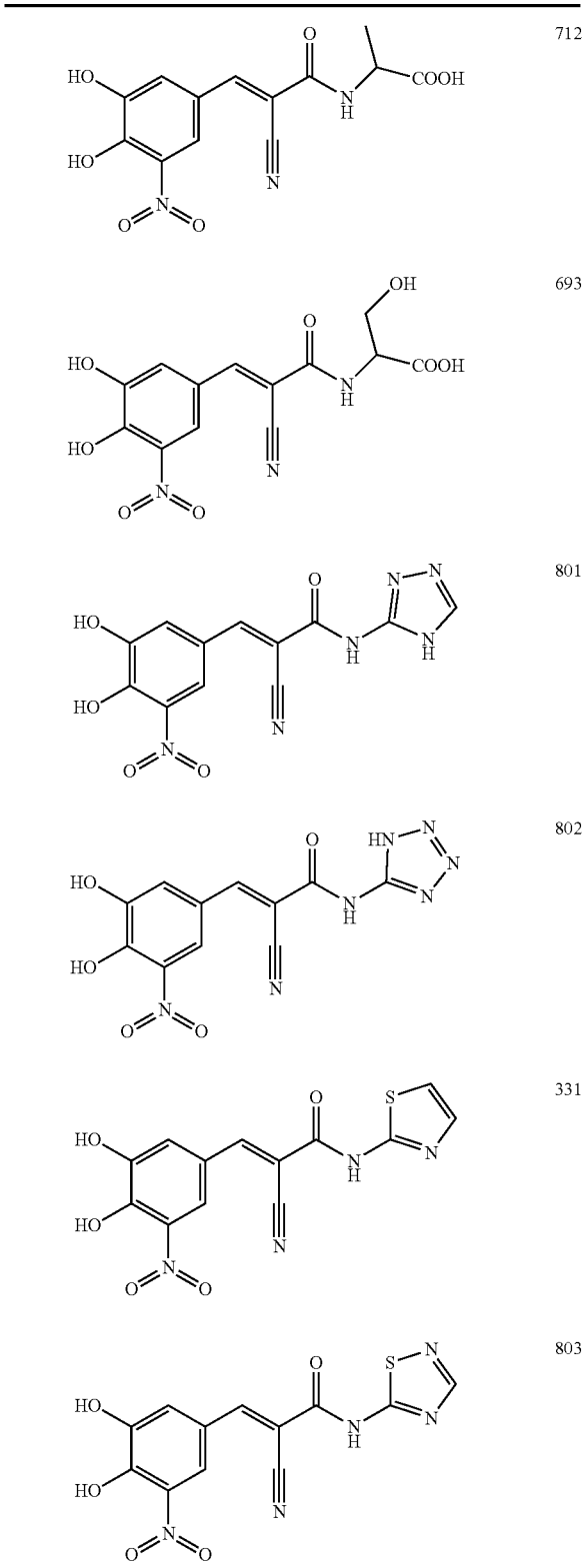
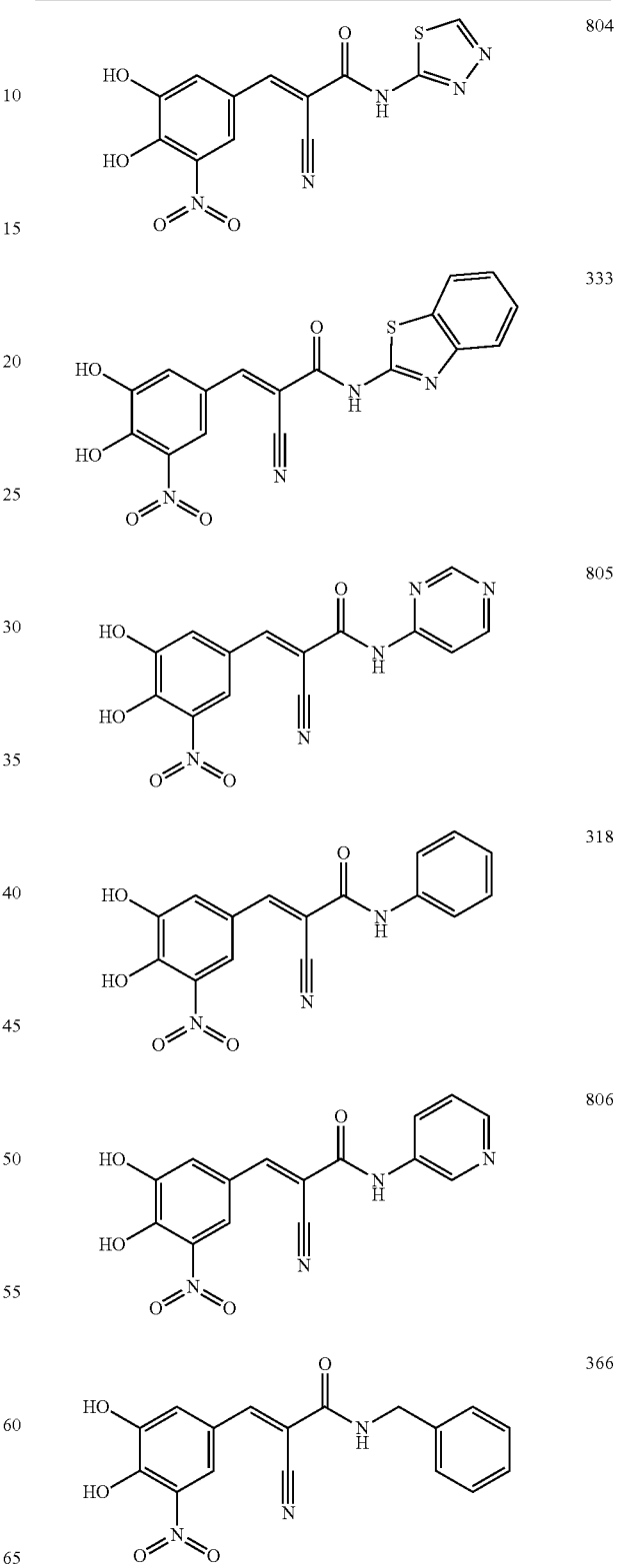

TABLE 3-continued

Subsection (b) inhibitors, wherein R4 is CONHR5, demonstrating IC50 value <10 μM in demethylation reaction catalyzed by FTO; experimental details below.

807

365

CAS ID: 1150310-12-5

380

374

668

673

674

722

374N

668N

673N

674N

TABLE 3-continued

Subsection (b) inhibitors, wherein R4 is CONHR5, demonstrating IC50 value <10 μM in demethylation reaction catalyzed by FTO; experimental details below.

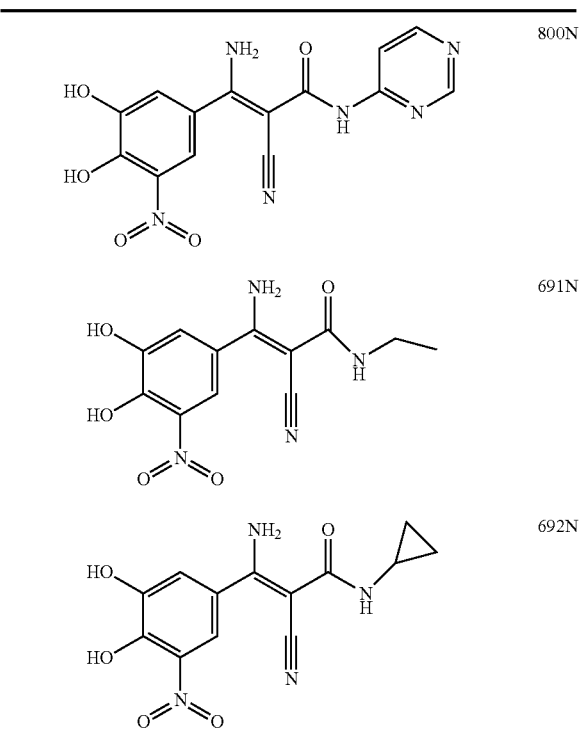

800N

691N

692N

TABLE 4

Subsection (c) inhibitors, wherein R4 is COR5, demonstrating IC50 value <10 μM in demethylation reaction catalyzed by FTO; experimental details below.

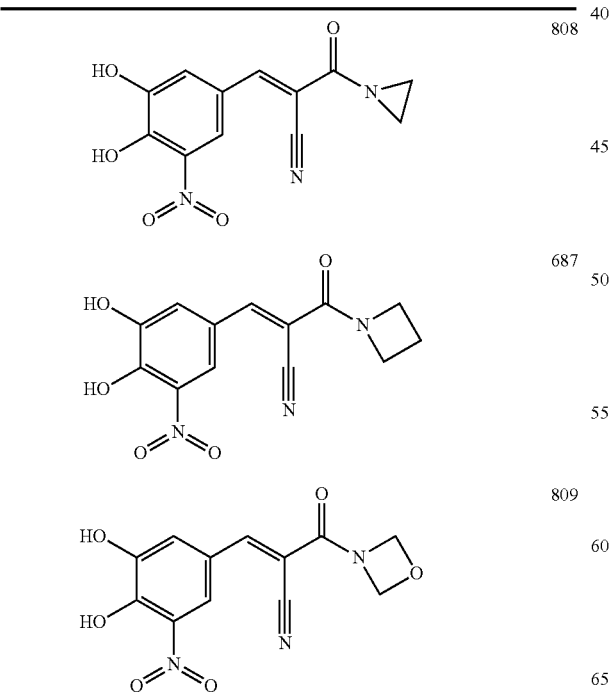

808

687

809

TABLE 4-continued

Subsection (c) inhibitors, wherein R4 is COR5, demonstrating IC50 value <10 μM in demethylation reaction catalyzed by FTO; experimental details below.

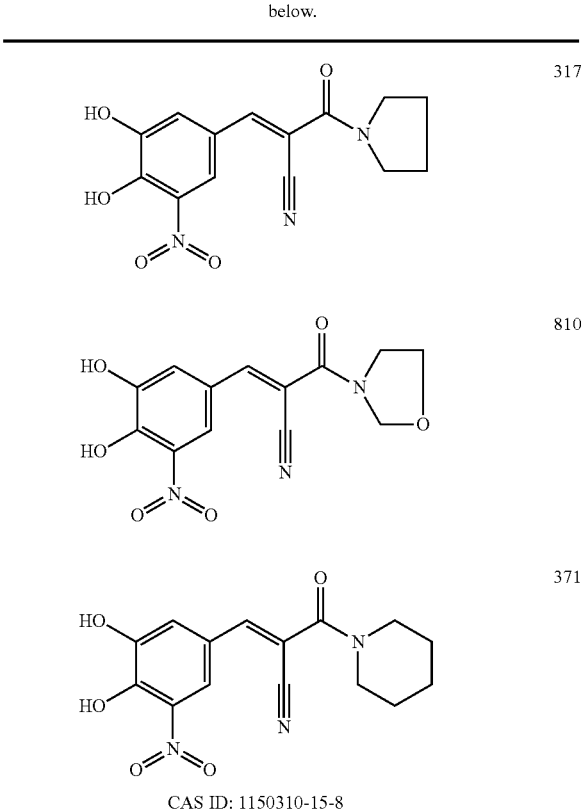

317

810

371

CAS ID: 1150310-15-8

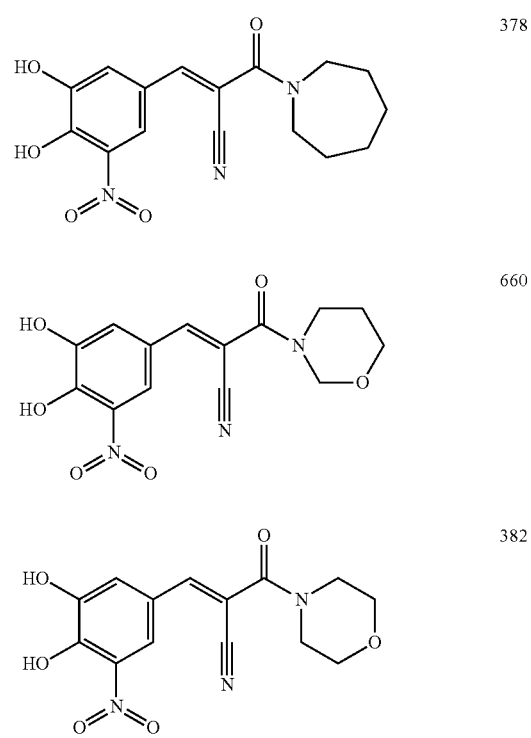

378

660

382

TABLE 4-continued
Subsection (c) inhibitors, wherein R4 is COR5, demonstrating IC50 value <10 μM in demethylation reaction catalyzed by FTO; experimental details below.
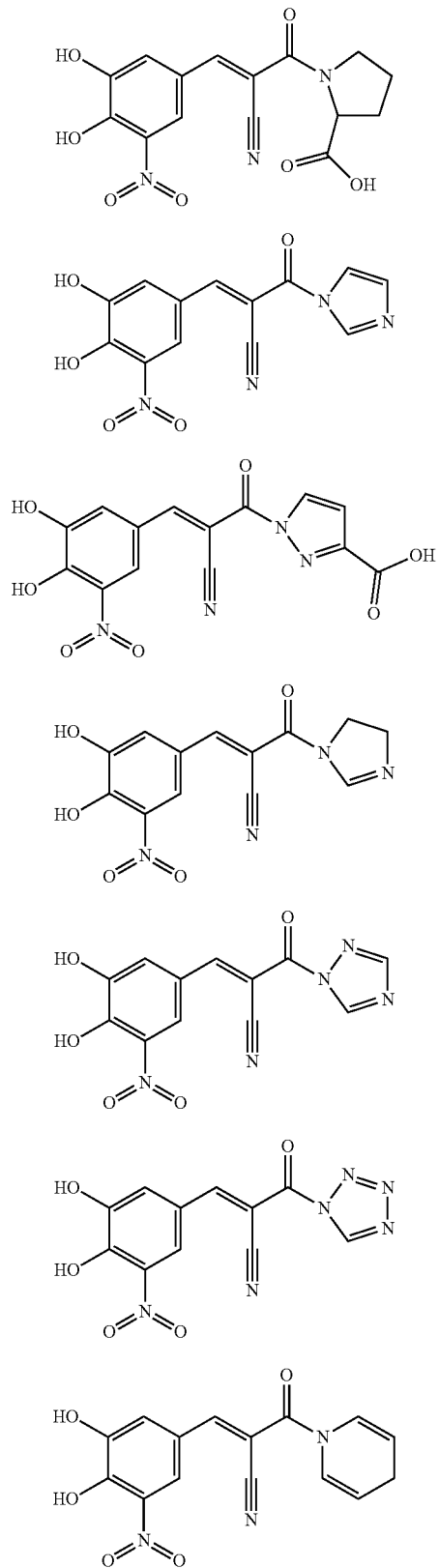
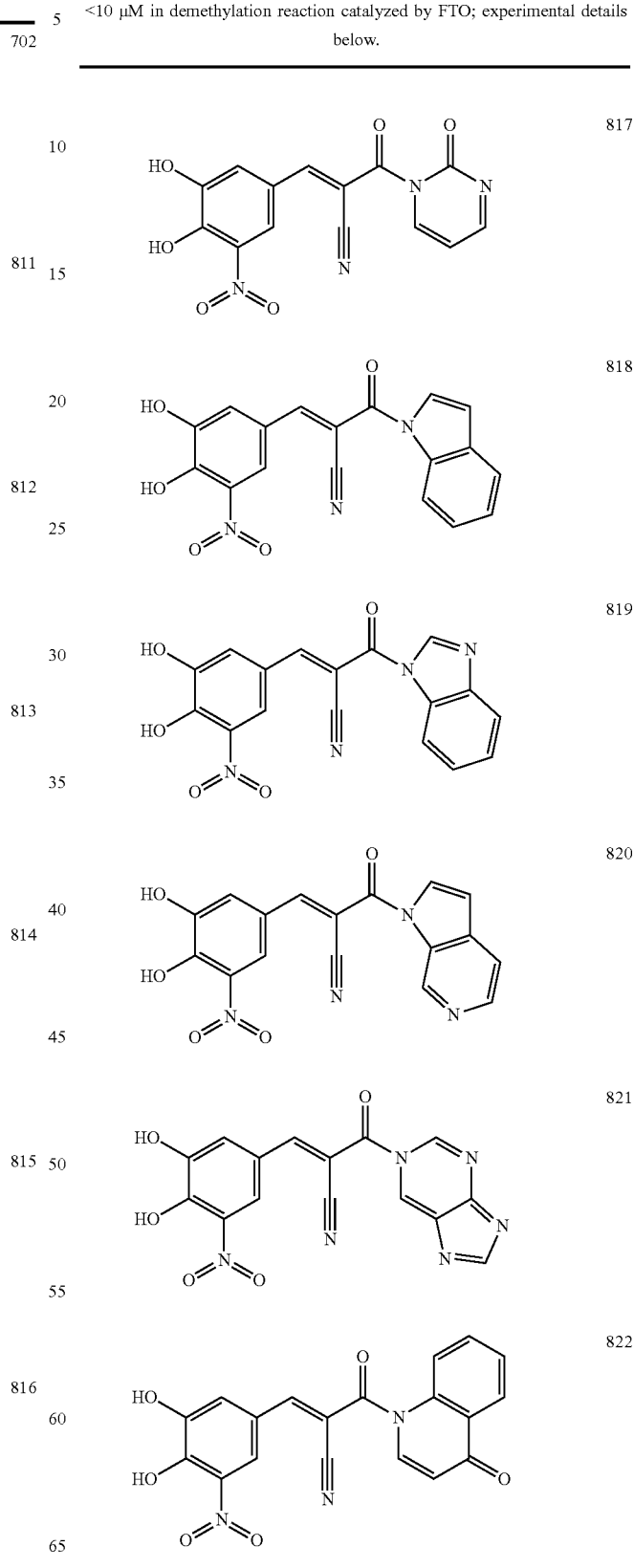

TABLE 4-continued
Subsection (c) inhibitors, wherein R4 is COR5, demonstrating IC50 value <10 μM in demethylation reaction catalyzed by FTO; experimental details below.
| | |
|---|---|
| 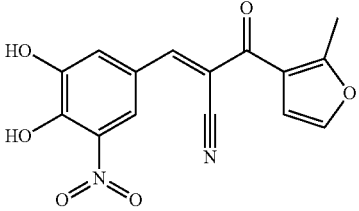 [SMILES: Cc1occc1C(=O)/C(C#N)=C/c1cc(O)c(O)c([N+](=O)[O-])c1] | 823 |
| 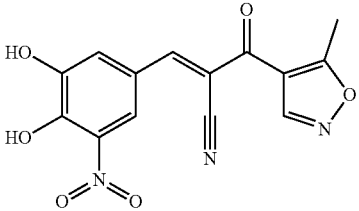 [SMILES: Cc1oncc1C(=O)/C(C#N)=C/c1cc(O)c(O)c([N+](=O)[O-])c1] | 824 |
| 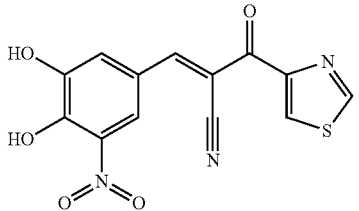 [SMILES: N#C/C(=C\c1cc(O)c(O)c([N+](=O)[O-])c1)C(=O)c1cscn1] | 698 |
| 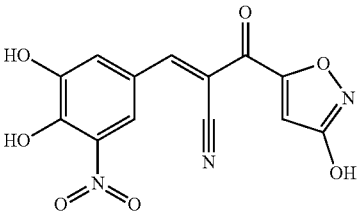 [SMILES: N#C/C(=C\c1cc(O)c(O)c([N+](=O)[O-])c1)C(=O)c1cc(O)no1] | 675 |
| 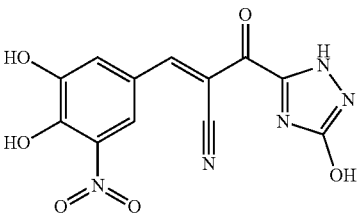 [SMILES: N#C/C(=C\c1cc(O)c(O)c([N+](=O)[O-])c1)C(=O)c1nc(O)n[nH]1] | 825 |
| 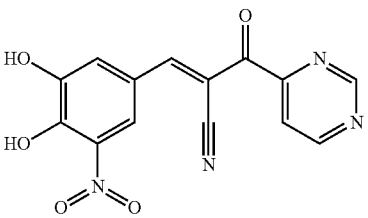 [SMILES: N#C/C(=C\c1cc(O)c(O)c([N+](=O)[O-])c1)C(=O)c1ccncn1] | 826 |
| 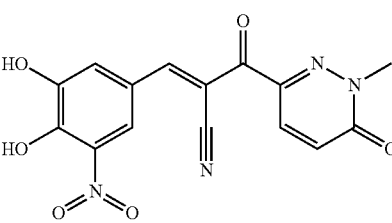 | 827 |
TABLE 4-continued
Subsection (c) inhibitors, wherein R4 is COR5, demonstrating IC50 value <10 μM in demethylation reaction catalyzed by FTO; experimental details below.
| | |
|---|---|
| 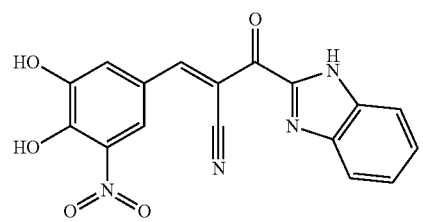 [SMILES: N#C/C(=C\c1cc(O)c(O)c([N+](=O)[O-])c1)C(=O)c1nc2ccccc2[nH]1] | 394 |
| 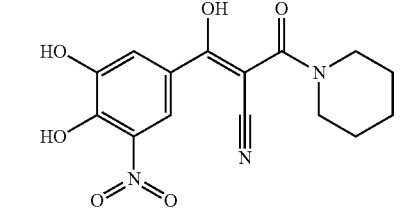 [SMILES: N#C/C(C(=O)N1CCCCC1)=C(/O)c1cc(O)c(O)c([N+](=O)[O-])c1] | 661 |
| 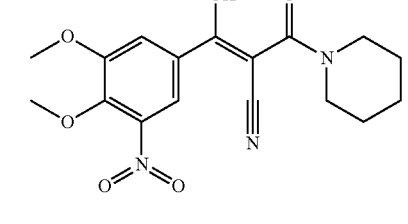 | 658 |
| 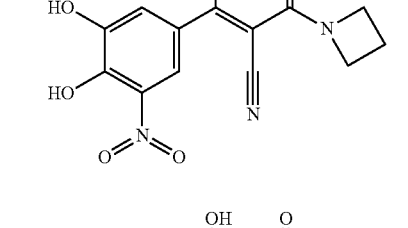 | 701 |
| 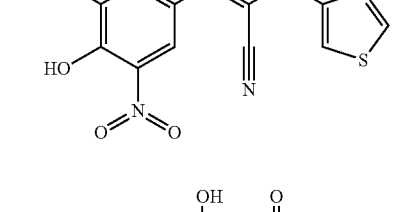 | 711 |
| 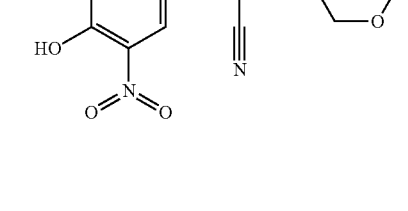 | 715 |

TABLE 4-continued

Subsection (c) inhibitors, wherein R4 is COR5, demonstrating IC50 value <10 μM in demethylation reaction catalyzed by FTO; experimental details below.

711N

661N

658N

701N

715N

TABLE 5

Subsection (d) inhibitors, wherein R4 is heterocyclic, demonstrating IC50 value <10 μM in demethylation reaction catalyzed by FTO; experimental details below.

390

TABLE 5-continued

Subsection (d) inhibitors, wherein R4 is heterocyclic, demonstrating IC50 value <10 μM in demethylation reaction catalyzed by FTO; experimental details below.

656

666

829

315

400

319

TABLE 5-continued
Subsection (d) inhibitors, wherein R4 is heterocyclic, demonstrating IC50 value <10 µM in demethylation reaction catalyzed by FTO; experimental details below.
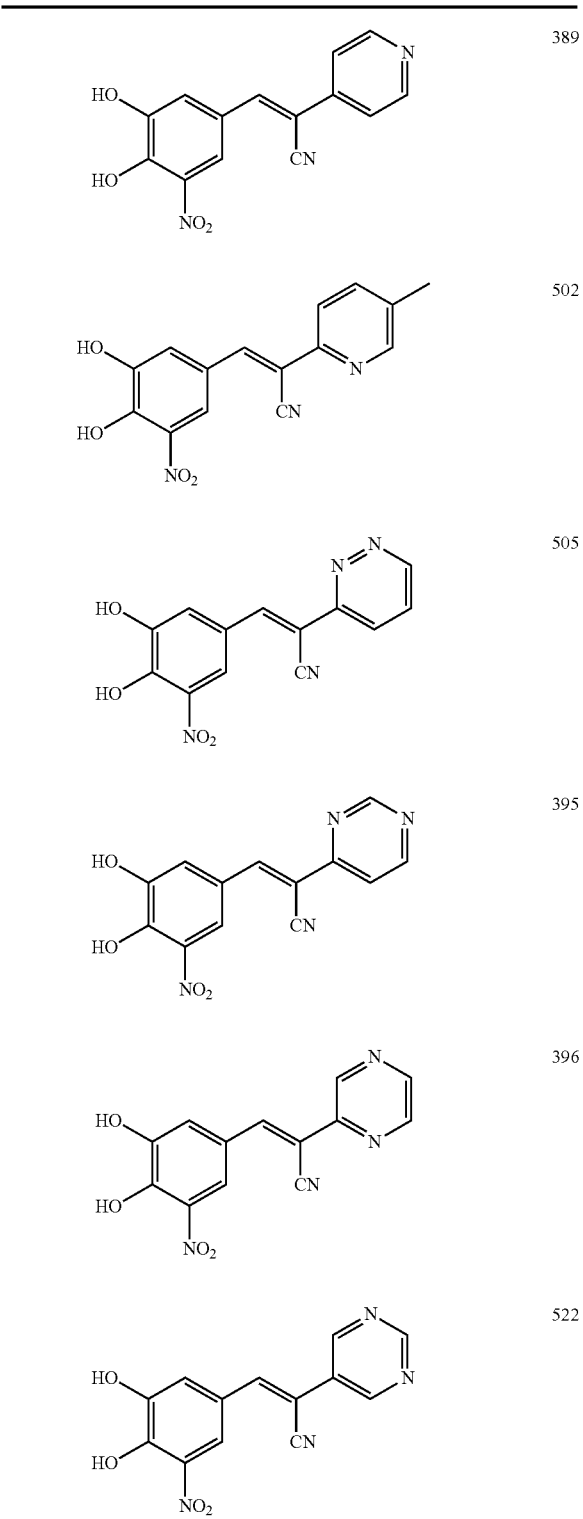
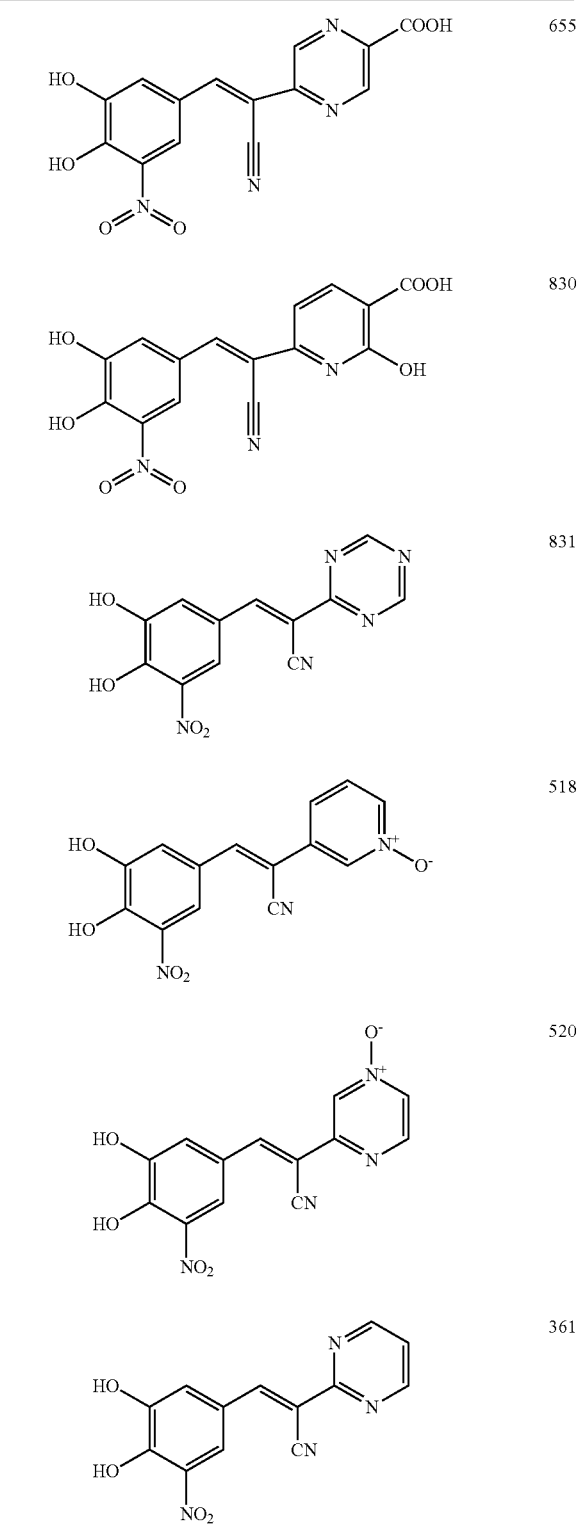
CAS ID: 143542-72-7

TABLE 5-continued
Subsection (d) inhibitors, wherein R4 is heterocyclic, demonstrating IC50 value <10 μM in demethylation reaction catalyzed by FTO; experimental details below.
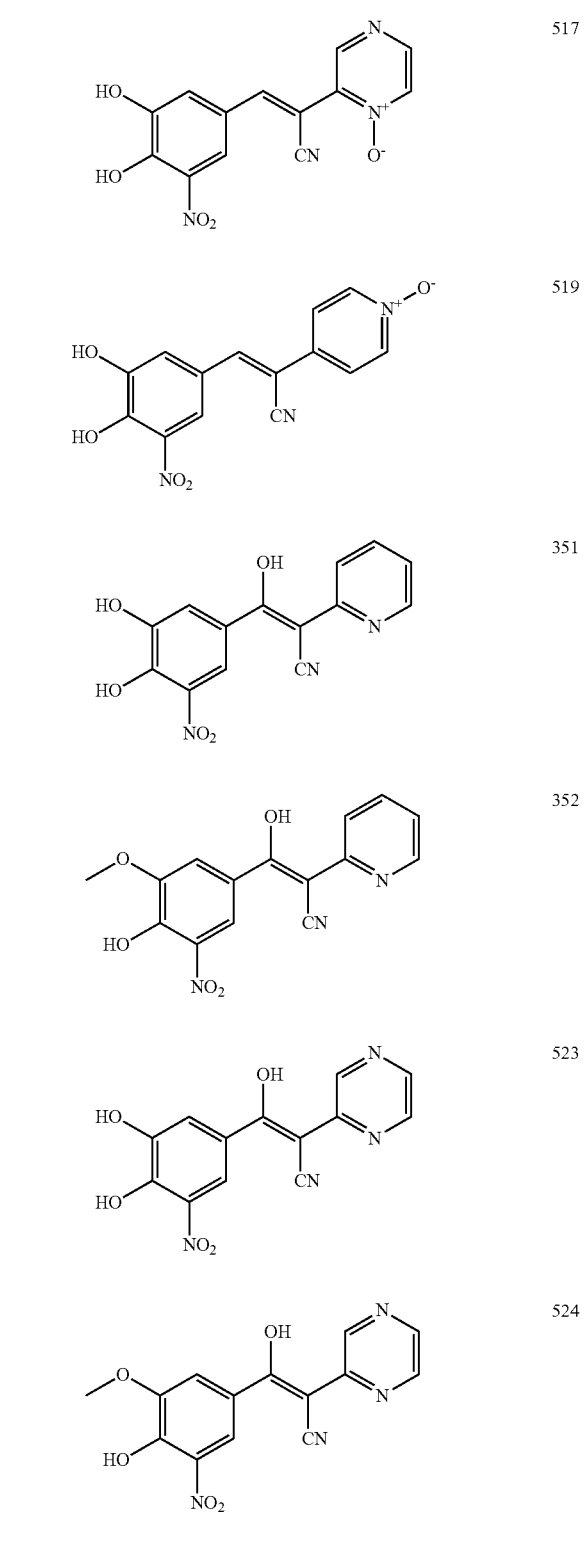
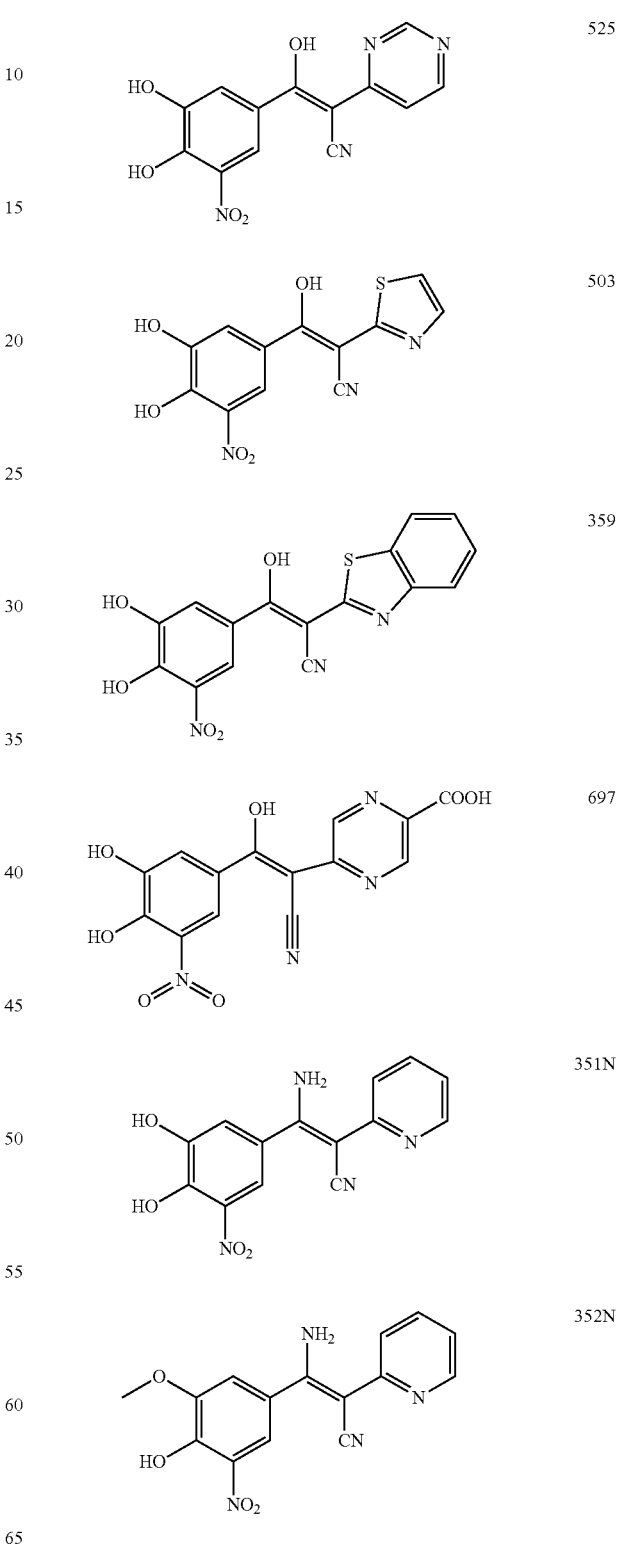

TABLE 5-continued

Subsection (d) inhibitors, wherein R4 is heterocyclic, demonstrating IC50 value <10 μM in demethylation reaction catalyzed by FTO; experimental details below.

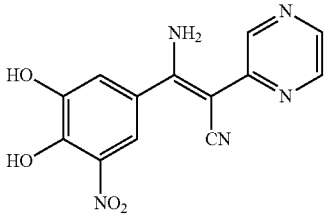
523N

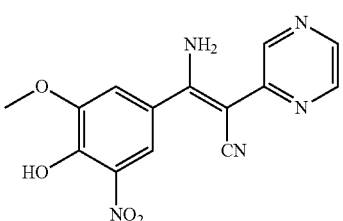
524N

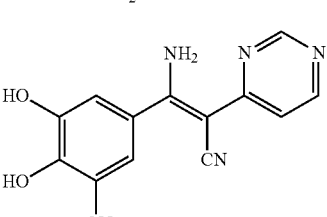
525N

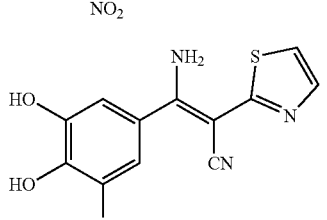
503N

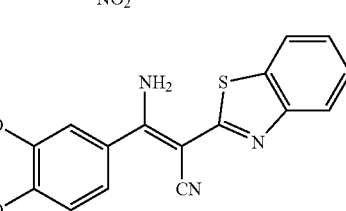
359N

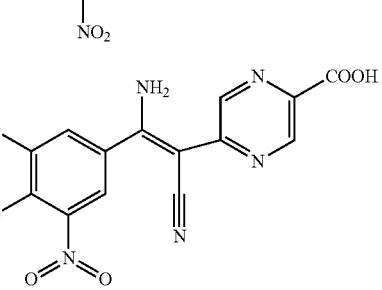
697N

In another aspect the invention provides a pharmaceutical composition suitable for administration to a human and comprising a subject or disclosed inhibitor.

The compositions may comprise a pharmaceutically-acceptable excipient, be in effective, unit dosage form, and/or comprise another, different therapeutic agents for the targeted disease or condition. In embodiments, the compositions may further comprise or be copackaged or coformulated with a second, different medicament for inhibiting weight gain, promoting weight loss, reducing serum LDL, cholesterol, LDL-c, or triglycerides, or treating obesity or an obesity related disease (esp. obesity-related diabetes, hyperglycemia, diabetic nephropathy, hyperlipemia, coronary heart disease, atherosclerosis, hypertension, cardiovascular or cerebrovascular disease) or Alzheimer's disease.

In embodiments:

the medicament is an AD drug that is an acetylcholinesterase inhibitor (esp. tacrine, rivastigmine, galantamine and donepezil) or an NMDA receptor antagonist (esp. memantine);

the medicament is a medicament for inhibiting weight gain that is a food intake inhibitor or a food absorption inhibitor;

the medicament is a medicament for inhibiting weight gain that is Orlistat, Sibutramine, Lorcaserin, Rimonabant, Metformin, Exenatide, Pramlintide, phentermine/topiramate, or a pharmaceutically-acceptable salt thereof;

the medicament is a medicament for reducing serum LDL, cholesterol, LDL-c, or triglycerides, that is atorvastatin (Lipitor), fluvastatin (Lescol), lovastatin (Altoprev, Mevacor), pravastatin (Pravachol), rosuvastatin (Crestor), simvastatin (Zocor), cholestyramine (Prevalite, Questran), colesevelam (Welchol), colestipol (Colestid), ezetimibe (Zetia), ezetimibe-simvastatin (Vytorin), fenofibrate (Lofibra, TriCor), gemfibrozil (Lopid), Niacin (Niaspan), Omega-3 fatty acid (Lovaza), or a pharmaceutically-acceptable salt thereof.

the medicament is a diabetes or hypoglycemia medicament, such as glibenclamide, glipizide, gliquidone, gliclazide, glimepiride, glibornuride, repaglinide, nateglinide, metformin, acarbose, voglibose, rosiglitazone, pioglitazone, exenatide, liraglutide, sitagliptin, saxagliptin, vildagliptin, canagliflozin, dapaglifozin, or a pharmaceutically-acceptable salt thereof.

In another aspect the invention provides methods of treating a person in need thereof with an effective amount of the subject inhibitor or pharmaceutical composition, and optionally, detecting a resultant improvement in the person's health or condition. The methods may also optionally include the antecedent step of determining that the person, particularly diagnosing and applicable disease or condition (herein). In embodiments the invention provides methods and uses of a subject inhibitor or composition in a person in need thereof, to inhibit FTO, inhibit weight gain, promote weight loss, reduce serum LDL, cholesterol, LDL-c, or triglycerides, or treat obesity or an obesity related disease or Alzheimer's Disease.

The invention encompasses all combination of the particular embodiments recited herein, as if each had been separately, laboriously recited. For example, subsection (a) encompasses combinations wherein: R1 and R2 are H; R3 is NH$_2$; and R4 is a 6 membered ring that is pyridine, and subsection (d) encompasses combinations wherein R1 and R2 are Me; R3 is OH; and R4 is 1,3 diazole.

DESCRIPTION OF PARTICULAR EMBODIMENTS OF THE INVENTION

The following descriptions of particular embodiments and examples are provided by way of illustration and not by way of limitation. Those skilled in the art will readily recognize a variety of noncritical parameters that could be changed or modified to yield essentially similar results.

Unless contraindicated or noted otherwise, in these descriptions and throughout this specification, the terms "a"

and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

A hydrocarbyl group is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which comprises 1-15 carbon atoms and optionally includes one or more heteroatoms in its carbon skeleton.

The term "heteroatom" as used herein generally means any atom other than carbon or hydrogen. Preferred heteroatoms include oxygen (O), phosphorus (P), sulfur (S), nitrogen (N), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2$—$CH_2$—$CH_2$—$CH_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N(CH3)-$CH_3$. Up to two heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent means a divalent radical derived from heteroalkyl, as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo($C_1$-$C_4$)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R'" each independently refer to hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO2R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO2R', —NR'—C(O)NR"R'", —NR'—SO$_2$NR"R'", —NH—C(NH2)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C1-C4)alko-xy and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C$_3$-C$_7$)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R, —N$_3$, —CH(Ph)$_2$, perfluoro(C$_1$-C$_4$)alkoxy and perfluoro(C$_1$-C$_4$)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C$_1$-C$_4$) alkoxy and perfluoro(C1-C4)alkyl.

The substituent —CO$_2$H, as used herein, includes bioisosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH$_2$)q-U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C1-C6)alkyl.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, optionally heteroatom C1-C6 alkyl, substituted or unsubstituted, optionally heteroatom C2-C6 alkenyl, substituted or unsubstituted, optionally heteroatom C2-C6 alkynyl, or substituted or unsubstituted, optionally heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

The term "pharmaceutically acceptable salts" is meant to include salts of the active compounds which are prepared with relatively nontoxic acids or bases, depending on the particular substituents found on the compounds described herein, and suitable for pharmaceutical use. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Some of the subject compounds possess asymmetric carbon atoms (optical centers) or double bonds; the racemates, diastereomers, geometric isomers and specifically designated or depicted chirality is preferred and in many cases critical for optimal activity; however all such isomers are all intended to be encompassed within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat an applicable disease or condition (herein).

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the compounds may be advantageously used in conjunction with other therapeutic agents as described herein or otherwise known in the art, particularly other anti-necrosis agents. Hence the compositions may be administered separately, jointly, or combined in a single dosage unit.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 5, 25 or 100 to about 5, 25, 100, 500, 1000 or 2000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10, 100, 1000, 10000, 20000 ug/kg to about 10, 100, 1000, 10000, 20000 or 80000 ug/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compounds can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

In particular embodiments thereof, the person to be treated has a genotype associated with obesity or pathogenic or medically-undesirable weight gain, such as SNP rs7202116 (G), rs1421085 (C), or rs9939609 (A), or a surrogate or proxy SNP in linkage disequilibrium therewith (with respect to the correlative phenotype; see references below) and having a $r^2$ value greater than 0.5; and/or (f) pathogenically expresses or over-expresses FTO or Fto (e.g. comprises and expresses a multi-copy fto gene). Re rs7202116 G, see e.g. Yang et al., FTO genotype is associated with phenotypic variability of body mass index, Nature, Sep. 16, 2012, doi: 10.1038/nature11401 [epub]; re rs9939609 A, see e.g. Freathy R M, et al (2008). "Common variation in the FTO gene alters diabetes-related metabolic traits to the extent expected, given its effect on BMI". Diabetes 57 (5): 1419-26. doi:10.2337/db07-1466. PMC 3073395. PMID 18346983; re rs1421085 C, see e.g. Dina C, et al., (2007). "Variation in FTO contributes to childhood obesity and severe adult obesity". Nature Genetics 39 (6): 724-6. doi:10.1038/ng2048. PMID 17496; and for multi-copy fto gene mouse, see e.g. Church et al., Overexpression of Fto leads to increased food intake and results in obesity, Nature Genetics, published online 14 Nov. 2010, doi: 10.1038/ng.713.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Examples: Compound Preparation

Compound 347:

347 was prepared in two synthetic steps from 3,4-dimethoxy-5-nitrobenzoic acid, according to the following procedure:

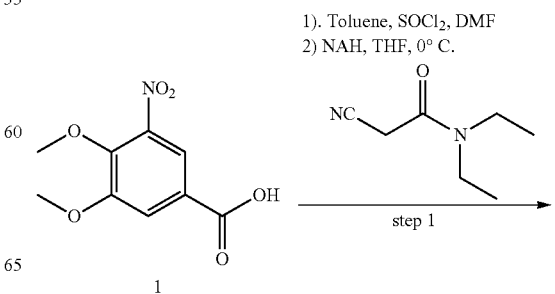

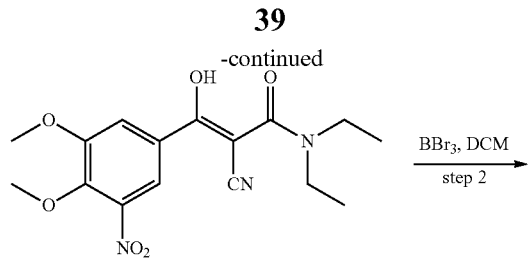

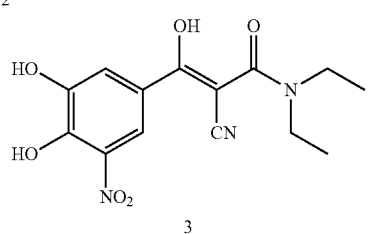

Step1: Synthesis of 2-cyano-3-(3,4-dimethoxy-5-nitrophenyl)-/N,N-diethyl-3-oxopropanamide (2)

Under a nitrogen atmosphere, SOCl$_2$ (0.38 mL, 5.28 mmol) and anhydrous DMF (0.01 mL, 0.22 mmol) were added to a suspension of 3,4-dimethoxy-5-nitrobenzoic acid (1.0 g, 4.4 mmol) in toluene (11 mL) at room temperature. The mixture was heated at 60° C. and stirred for 15 hours. The organic solvent was eliminated by distillation under reduced pressure. More toluene was added and eliminated again. The resulting yellowish solid 3,4-dimethoxy-5-nitrobenzoyl chloride was dissolved in anhydrous THF (10 mL).

Under a nitrogen atmosphere, 60% NaH (0.35 g, 8.8 mmol) was added to solution of 2-cyano-N,N-diethylacetamide (0.56 g, 4.0 mmol) in anhydrous THF (15 mL) at −5° C. The resulting suspension was stirred at −5° C. for 15 min and the THF solution of 3,4-dimethoxy-5-nitrobenzoyl chloride was added over 10 min and stirred for an additional 1 h at −5° C. The reaction mixture was warmed to 0° C., quenched by the addition of 1N.HCl solution (4 mL) and stirred for 10 min at room temperature, extracted by ethyl acetate (25 mL×2), the organic layers was dried with Na$_2$SO$_4$ and concentrated in vacuo to give the title compound as an orange solid (705 mg, 99%). MS [MH]$^+$ calcd for C$_1$H$_{19}$N$_3$O$_6$ 350.1, found 350.1.

Step2: Synthesis of 2-cyano-3-(3,4-dihydroxy-5-nitrophenyl)-N,N-diethyl-3-oxopropanamide (3)

A solution of 2-cyano-3-(3,4-dimethoxy-5-nitrophenyl)-N,N-diethyl-3-oxopropanamide (500 mg, 1.43 mmol) in DCM (5 mL) was added 1.0 M solution of BBr$_3$ in DCM (5 mL, 5 mmol) at −15° C. under a nitrogen atmosphere. The resulting red suspension was stirred for 1 h at −15° C. and allowed to warm to room temperature overnight. The reaction was quenched by the addition of H$_2$O (2 mL) and stirred for 30 min. The aqueous phase was extracted with ethyl acetate (30 mL×3). The organic layers were combined, washed with brine and dried over Na$_2$SO$_4$. The solvent was eliminated under reduced pressure to give the crude product. Further purification by Prep-HPLC (0.5% TFA, MeOH/H$_2$O) gave the desired product as a bright yellow solid (80 mg, 17%). $^1$H NMR (400 MHz, CDCl$_3$) δ 10.92 (s, 1H), 8.28 (d, J=2.0 Hz, 1H), 7.74 (d, J=1.9 Hz, 1H), 7.26 (s, 3H), 5.93 (s, 1H), 3.66 (d, J=6.0 Hz, 3H), 1.33 (t, J=7.0 Hz, 6H). MS [MH]$^+$ calcd for C$_{14}$H$_{15}$N$_3$O$_6$ 322.0, found 322.0.

Compound 315:

315 was prepared in one synthetic step from 3,4-dihydroxy-5-nitrobenzaldehyde, according to the following procedure:

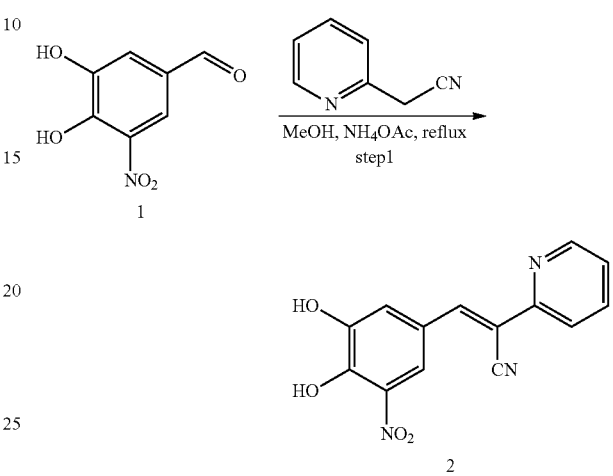

Step1: Synthesis of (E)-3-(3,4-dihydroxy-5-nitrophenyl)-2-(pyridin-2-yl)acrylonitrile (2)

A solution of 2-(pyridin-2-yl)acetonitrile (142 mg, 1.2 mmol), 3,4-dihydroxy-5-nitrobenzaldehyde (182 mg, 1 mmol) and NH$_4$OAc (462 mg, 6 mmol) in MeOH (10 mL) was heated to reflux for overnight. LCMS showed no 3,4-dihydroxy-5-nitrobenzaldehyde left. The reaction mixture was cooled to room temperature. The solid was filtered and washed by MeOH and H$_2$O. The solid was re-dissolved in MeOH (5 mL). 5 mL of 1N aqueous HCl was added to adjust pH 3~4. The desired product was obtained by filter as a bright solid (56 mg, 20%). $^1$H NMR (400 MHz, DMSO) δ 8.57 (m, 1H), 8.12 (s, 1H), 7.92 (d, J=2.2 Hz, 1H), 7.84 (td, J=7.8, 1.8 Hz, 1H), 7.70 (d, J=8.1 Hz, 1H), 7.56 (d, J=2.4 Hz, 1H), 7.31-7.25 (m, 1H). MS [MH]$^+$ calcd for C$_{14}$H$_9$N$_3$O$_4$ 284.0, found 284.0.

Compound 361:

361 was prepared in four synthetic steps from malonamide, according to the following procedure:

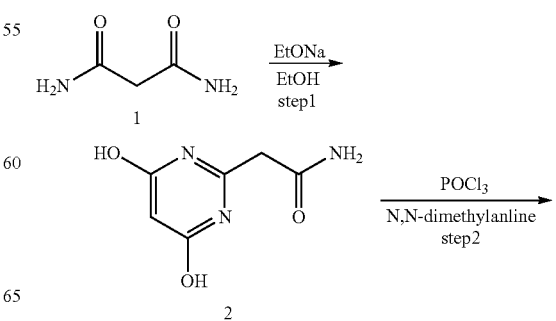

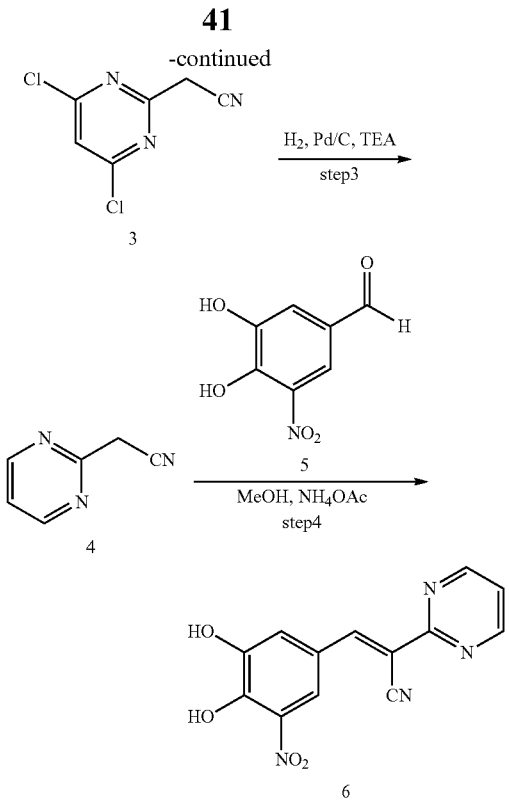

Step1: Synthesis of 2-(4,6-dihydroxypyrimidin-2-yl)acetamide (2)

To a solution of NaOEt (21% in EtOH, 167 mL, 450 mmol) in EtOH (170 mL) was added malonamide (22.9 g, 224 mmol). After being refluxed for 2 hours, half of EtOH was removed under reduced pressure and the precipitated solid was filtered and dried under high vacuum for overnight. The dried solid sodium salt (24 g) was dissolved in ice-cold $H_2O$ (70 mL) and brought to pH 2~3 using 3N. HCl (50 mL), recrystallization from water gave 2-(4,6-dihydroxypyrimidin-2-yl)acetamide as a pale yellow solid (6.28 g, 33%).

Step2: Synthesis of 2-(4,6-dichloropyrimidin-2-yl)acetonitrile (3)

To a solution of 2-(4,6-dihydroxypyrimidin-2-yl)acetamide (6.28 g, 37.1 mmol) in $POCl_3$ (19 mL, 204 mmol) was placed in a flask which was then attached to a reflux condenser. Through the condenser was added N,N-dimethylaniline (10 mL, 79 mmol). The mixture was warmed cautiously in an oil bath which is quickly removed when the reaction began. After the initial vigorous reaction had subsided, the reaction was refluxed for ten minutes longer. The hot material was poured over 100 g ice and the resulting suspension was extracted (DCM). The combined organic layers were dried ($Na_2SO_4$) and concentrated under reduced pressure. The product was purified by column chromatography ($SiO_2$, PE/EA=4/1) to provide the desired product as a yellow solid (5.1 g, 27.1 mmol). MS [MH]$^+$ calcd for $C_6H_3Cl_2N_3$ 189.0, found 189.0.

Step3: Synthesis of 2-(pyrimidin-2-yl)acetonitrile (4)

To a solution of 2-(4,6-dichloropyrimidin-2-yl)acetonitrile (2.2 g, 11.7 mmol) and triethylamine (3.0 mL, 20.8 mmol) in ethyl acetate/MeOH (1/1, 40 mL) was added 10% Pd/C (400 mg) and the solution was vigorously stirred for 2.5 hours under $H_2$ atmosphere (1 atm). The reaction was filtered through celite and washed the celite with MeOH. The combined filtrates were concentrated under reduced pressure and purified by flash chromatography ($SiO_2$, PE/EA=1/1) to give the 2-(pyrimidin-2-yl)acetonitrile as a pale red liquid (618 mg, 54%). MS [MH]$^+$ calcd for $C_6H_5N_3$ 120.1, found 120.1.

Step4: Synthesis of (E)-3-(3,4-dihydroxy-5-nitrophenyl)-2-(pyrimidin-2-yl)acrylonitrile (6)

A solution of 2-(pyrimidin-2-yl)acetonitrile (120 mg, 1 mmol), 3,4-dihydroxy-5-nitrobenzaldehyde (182 mg, 1 mmol) and $NH_4OAc$ (462 mg, 6 mmol) in MeOH (10 mL) was heated to reflux for 5 hours. LCMS showed no starting materials left. The solid was filtered and washed by MeOH and $H_2O$, then dissolved in MeOH (5 mL). 5 mL of 1N.HCl was added to adjust pH 3~4, the solid was filtered and dried in vacuo to give the desired product as a bright yellow solid (250 mg, 88%). $^1$H NMR (400 MHz, DMSO) δ 8.78 (d, J=4.8 Hz, 2H), 8.35 (s, 1H), 7.96 (d, J=2.5 Hz, 1H), 7.59 (d, J=2.5 Hz, 1H), 7.32 (t, J=4.8 Hz, 1H). MS [MH]$^+$ calcd for $C_{13}H_8N_4O_4$ 285.0, found 285.0.

Compound 395:

395 was prepared in four synthetic steps from 4-methylpyrimidine, according to the following procedure:

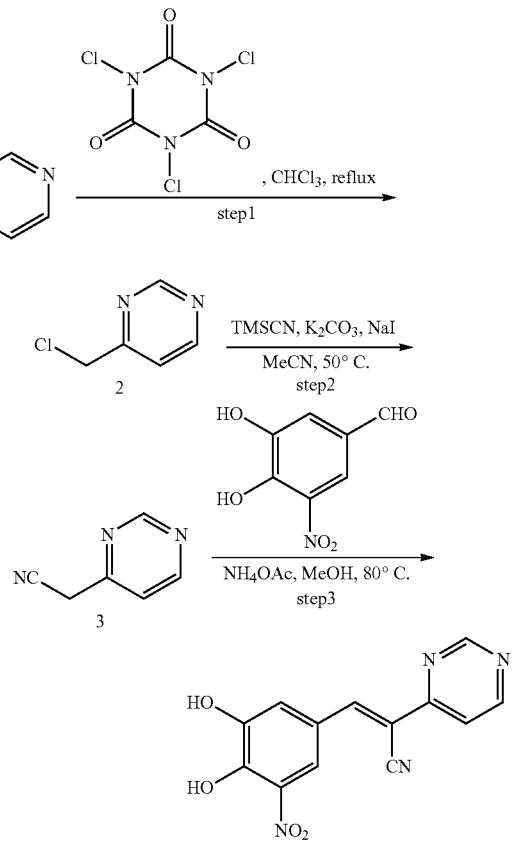

Step1: Synthesis of 4-(chloromethyl)pyrimidine (2)

4-methylpyrimidine (53.1 mmol, 5 g) was dissolved in CHCl$_3$ (100 mL), the mixture was heated to 75° C., then 1,3,5-trichloro-1,3,5-triazinane-2,4,6-trione (26.6 mmol, 6.2 g) was added slowly in two portions. The mixture was stirred at 75° C. overnight. After the completion of the reaction, it was filtered and concentrated in vacco. The residue was purified by column chromatograph (silica gel, PE/EA=30/1 to 10/1) to obtain the desired product (1.64 g, 24%) as a yellow oil. $^1$H-NMR (400 MHz, CDCl$_3$) δ (ppm) 9.16 (s, 1H), 8.77 (d, J=5.2 Hz, 1H), 7.54 (d, J=5.1 Hz, 1H), 4.60 (s, 2H); MS [MH]+ calcd for C$_5$H$_6$ClN$_2$ 129.0, found 129.1;

Step2: Synthesis of 2-(pyrimidin-4-yl)acetonitrile (3)

Anhydrous potassium carbonate (7.78 mmol, 1.08 g), sodium iodide (3.89 mmol, 583 mg) and trimethylsilanecarbonitrile (5.83 mmol, 579 mg) were dissolved in acetonitrile (12 mL), the mixture was heated to 50° C. Finally 4-(chloromethyl)-pyrimidine (3.89 mmol, 500 mg) was dropped into the reaction mixture. The mixture was stirred 50° C. for 2 hours. Then it was concentrated in vacco and the residue was purified by column chromatograph (silica gel, PE/EA=1/1) to obtain the desired product (120 mg, 26%) as a black oil. $^1$H-NMR (400 MHz, CDCl$_3$) δ (ppm) 9.21 (s, 1H), 8.81 (d, J=5.2 Hz, 1H), 7.52 (d, J=5.0 Hz, 1H), 3.94 (s, 2H); MS [MH]+ calcd for C$_6$H$_6$N$_3$ 120.1, found 120.2.

Step3: Synthesis of 3-(3,4-dihydroxy-5-nitrophenyl)-2-(pyrimidin-4-yl)acrylonitrile (4)

A mixture of 2-(pyrimidin-4-yl)acetonitrile (0.95 mmol, 113 mg), 3,4-dihydroxy-5-nitrobenzaldehyde (0.79 mmol, 145 mg) and ammonium acetate (4.75 mmol, 366 mg) in methanol (8 mL) was stirred at 80° C. for 4 hours, then it was filtered and washed with methanol and water to obtain the desired product (200 mg, 89%). $^1$H-NMR (400 MHz, DMSO) δ(ppm) 9.08 (s, 1H), 8.72 (d, J=5.5 Hz, 1H), 8.31 (s, 1H), 8.02 (s, 1H), 7.74 (d, J=5.5 Hz, 1H), 7.59 (s, 1H), 7.08 (s, 2H); MS [MH]$^-$ calcd for C$_{13}$H$_7$N$_4$O$_4$ 283.1, found 283.0;

Compound 505:

505 was prepared in three synthetic steps from 3-chloropyridazine, according to the following procedure:

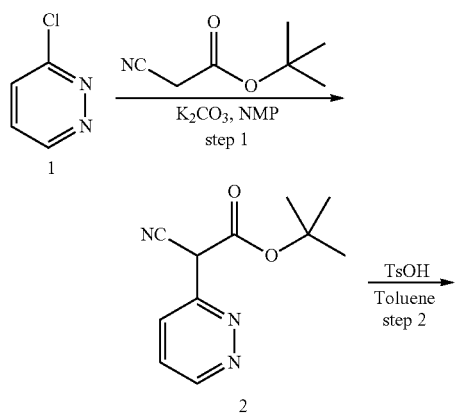

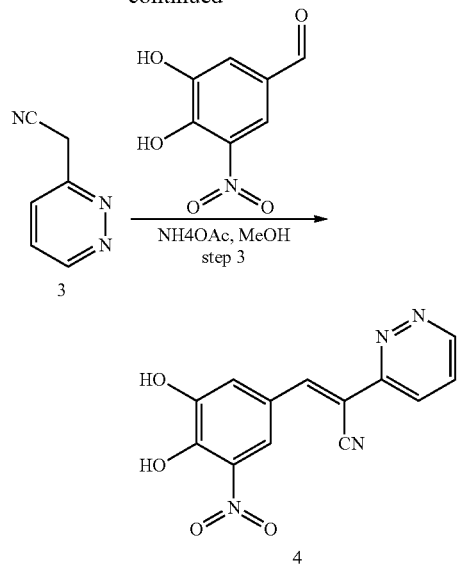

Step1: Synthesis of Tert-Butyl 2-cyano-2-(pyridazin-3-yl)acetate (2)

To a solution of 3-chloropyridazine (0.5 g, 4.38 mmol) in NMP (2.5 mL) was added potassium carbonate (1.8 g, 13.15 mmol). Then tert-Butyl 2-cyanoacetate (0.88 mL, 6.14 mmol) was added. The yellow suspension was warmed up to 80° C. and stirred 3 hours at 80° C. The brown suspension was cooled down to room temperature. Then it was added to water (10 mL). The brown solution was acidified with HCl (gas evolution, strong foaming). There was a precipitation. The suspension was filtrated and the filter cake was washed with water. The filter cake was dissolved in ethyl acetate, dried with Na$_2$SO$_4$, filtrated and the organic phase evaporated to yield 600 mg of desired product as a yellow oil. $^1$H-NMR (400 MHz, CDCl$_3$) δ (ppm): 14.3 (bs, 1H), 7.68 (dd, 1H), 7.35 (d, 1H), 1.55 (s, 9H). MS [MH]$^+$ calcd for C$_{10}$H$_{11}$N$_3$O$_2$ 206.1, found 206.1;

Step2: Synthesis of 2-(pyridazin-3-yl)acetonitrile (3)

The product prepared above was combined with TsOH (142 mg) in toluene (50 mL). After being stirred at refluxing for 12 hours, the reaction was cooled to 25° C., diluted with sat. NaHCO$_3$ and extracted (10 percent MeOH/CH$_2$Cl$_2$×3). The organic layers were washed with brine, dried with Na$_2$SO$_4$, filtered and concentrated under reduced pressure. Purification of the crude material by flash chromatography (silica gel, 40-45 percent EtOAc/Hexanes) gave the desired product (87 mg, 17% for two steps) as light yellow oil. MS [MH]$^+$ calcd for C$_6$H$_5$N$_3$ 120.0, found 120.0.

Step3: Synthesis of (E)-3-(3,4-dihydroxy-5-nitrophenyl)-2-(pyridazin-3-yl)acrylonitrile (4)

A mixture of 2-(pyrazin-2-yl)acetonitrile (87 mg, 0.73 mmol), 3,4-dihydroxy-5-nitrobenzaldehyde (0.79 mmol, 145 mg) and ammonium acetate (366 mg, 4.75 mmol) in methanol (8 mL) was stirred at 80° C. for 4 hours. Then it was filtered and washed with methanol and water, and dried in vacuo to obtain the desired product (155 mg, 75%) as a yellow solid. ¹H NMR (400 MHz, DMSO) δ 10.92 (s, 2H), 9.25 (d, J=4.8 Hz, 1H), 8.43 (s, 1H), 8.20 (d, J=8.7 Hz, 1H), 8.08 (d, J=2.0 Hz, 1H), 7.95 (d, J=2.0 Hz, 1H), 7.85 (dd, J=8.7, 4.9 Hz, 1H). MS [MH]⁻ calcd for C₆H₅N₃ 283.1, found 283.0.

Compound 331:

331 was prepared in one synthetic step from 3,4-dihydroxy-5-nitrobenzaldehyde, according to the following procedure:

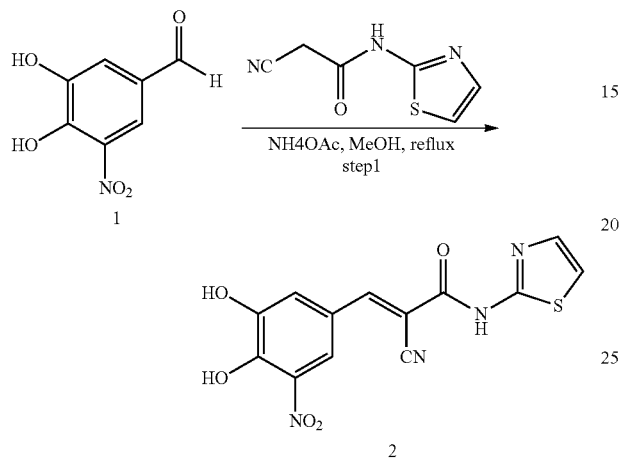

Step1: Synthesis of (E)-2-cyano-3-(3,4-dihydroxy-5-nitrophenyl)-N-(thiazol-2-yl)acrylamide (2)

A solution of 2-cyano-N-(thiazol-2-yl)acetamide (184 mg, 1.1 mmol), 3,4-dihydroxy-5-nitrobenzaldehyde (200 mg, 1.1 mmol) and NH₄OAc (462 mg, 6 mmol) in MeOH (10 mL) was heated to reflux for overnight. LCMS showed no 3,4-dihydroxy-5-nitrobenzaldehyde left. The reaction mixture was cooled to room temperature. The solid was filtered and washed by MeOH and H₂O. The solid was re-dissolved in MeOH (5 mL). 5 mL of 1N aqueous HCl was added to adjust pH 3~4. The desired product was obtained by filter as a bright solid (90 mg, 25%). ¹H NMR (400 MHz, DMSO) δ 8.17 (s, 1H), 7.95 (s, 1H), 7.50 (s, 2H), 7.20 (s, 1H). MS [MH]⁺ calcd for C₁₃H₈N₄O₅S 333.0, found 333.0.

Compound 394:

394 was prepared in four synthetic steps from benzene-1,2-diamine, according to the following procedure:

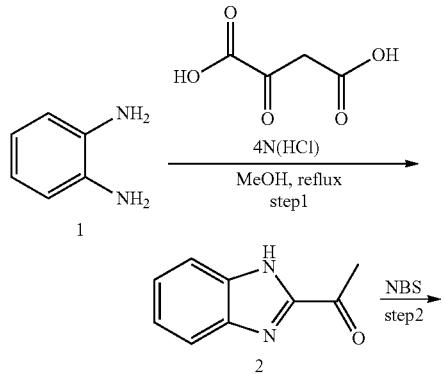

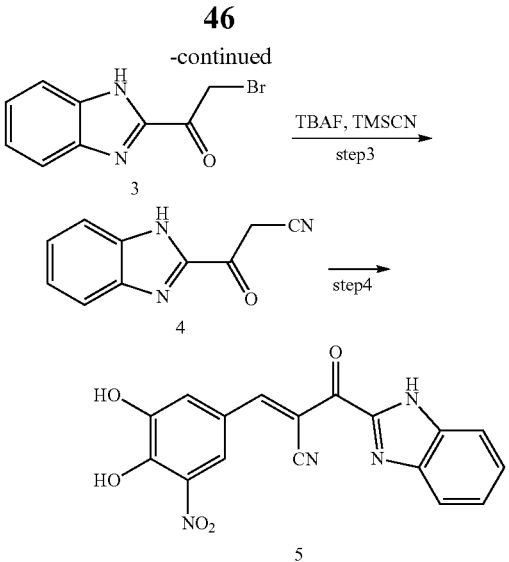

Step1: Synthesis of 1-(1H-benzo[d]imidazol-2-yl)ethanone (2)

A mixture of 2-oxosuccinic acid (4.9 g, 37 mmol), benzene-1,2-diamine (4 g, 37 mmol) and 4N hydrochloride solution (9 mL) in MeOH (30 mL) was refluxed for 7 hours. After the completion of the reaction, it was concentrated in vacuo to remove the solvent. The residue was dissolved in ethyl acetate, washed with aq. sodium bicarbonate and brine. The organic layers were combined and concentrated under reduced pressure. The residue was purified by column chromatograph (silica gel, PE/EA=5/1) to obtain the desired product (4 g, 67%). MS [MH]⁺ calcd for C₉H₉N₂O 161.06, found 161.1.

Step2: Synthesis of 1-(1H-benzo[d]imidazol-2-yl)-2-bromoethanone (3)

1-(1H-benzo[d]imidazol-2-yl)ethanone (4 g, 25 mmol) was dissolved in tetrachloromethane (50 mL). 1-Bromopyrrolidine-2,5-dione (5.3 g, 30 mmol) and 2,2'-(diazene-1,2-diyl)bis(2-methylpropane-nitrile) (411 mg, 2.5 mmol) were added. The mixture was stirred at 100° C. for 2 hours, then it was concentrated in vacuo and re-dissolved in ethyl acetate. The organic layer was washed with water and concentrated to obtain the crude product (2 g, 33%), which was used in the next step without further purification. MS [MH]⁺ calcd for C₉H₈BrN₂O 238.97, found 239.0.

Step3: Synthesis of 3-(1H-benzo[d]imidazol-2-yl)-3-oxopropanenitrile (4)

A mixture of 1-(1H-benzo[d]imidazol-2-yl)-2-bromoethanone (2 g, 8.4 mmol), trimethylsilane-carbonitrile (1.66 g, 16.7 mmol), TBAF (2.2 g, 8.4 mmol) in dichloromethane (15 mL) was stirred at room temperature for 24 hours. Then it was concentrated in vacuo and re-dissolved in ethyl acetate. The organic layer was washed with water and concentrated to obtain the crude product (400 mg, 26%), which was used in the next step without further purification. MS [MH]⁺ calcd for C₁₀H₇N₃O 186.06, found 186.1.

Step4: Synthesis of 2-(1H-benzo[d]imidazole-2-carbonyl)-3-(3,4-dihydroxy-5-nitrophenyl)acrylonitrile (5)

A solution of 3,4-dihydroxy-5-nitrobenzaldehyde (107 mg, 0.59 mmol) and 3-(1H-benzo[d]imida-zole-2-yl)-3- oxopropanenitrile (130 mg, 0.7 mmol) and NH₄OAc (273 mg, 3.54 mmol) in methanol (10 mL) was heated to reflux for overnight. LCMS showed the desired product was formed, the reaction mixture was cooled to room temperature and concentrated in vacuo to remove the solvent. The desired product was obtained by Prep-HPLC (50 mg, 24%). ¹H-NMR (400 MHz, DMSO-d⁶) δ (ppm) 12.63 (s, 1H), 8.95 (s, 1H), 7.85 (s, 1H), 7.76 (d, J=8.2 Hz, 1H), 7.65 (s, 1H), 7.50 (t, J=7.5 Hz, 1H), 7.38-7.26 (m, 2H), 7.12 (s, 2H). MS [MH]⁺ calcd for $C_{17}H_{11}N_4O_5$ 351.07, found 351.0.

Compound 382:

382 was prepared in two synthetic steps from ethyl 2-cyanoacetate, according to the following procedure:

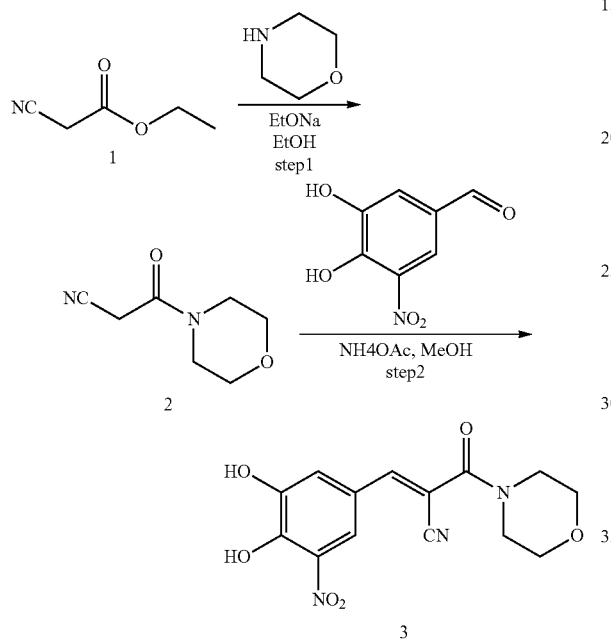

Step1: Synthesis of 3-morpholino-3-oxopropanenitrile (2)

A mixture of sodium ethoxide (0.1 mmol) in ethanol (3 mL), ethyl cyanoacetate (1.13 g, 10 mmol) and morpholine (0.85 g, 10 mmol) was stirred at room temperature for 24 hours. The precipitate was collected by filtration, washed with diethylether and recrystallised in ethanol to provide a white solid of 3-morpholino-3-oxopropanenitrile (0.56 g, 35%).

Step2: Synthesis of (E)-3-(3,4-dihydroxy-5-nitrophenyl)-2-(piperidine-1-carbonyl)acrylonitrile (3)

A solution of 3-morpholino-3-oxopropanenitrile (300 mg, 2.0 mmol), 3,4-dihydroxy-5-nitro-benzaldehyde (188 mg, 1.1 mmol) and NH₄OAc (462 mg, 6 mmol) in MeOH (10 mL) was heated to reflux for 5 hours. LCMS showed no 3,4-dihydroxy-5-nitrobenzaldehyde left. The reaction mixture was cooled to room temperature, concentrated in vacuo to dryness. Further purification by Prep-HPLC (0.5% TFA, MeOH/H₂O) afforded the desired product as a yellow solid (60 mg, 19%). ¹H NMR (400 MHz, DMSO) δ 10.87 (s, 2H), 7.94 (d, J=2.1 Hz, 1H), 7.77 (d, J=2.1 Hz, 1H), 7.68 (s, 1H), 3.56-3.66 (m, 8H). MS [MH]⁺ calcd for $C_{14}H_{13}N_3O_6$ 320.1, found 320.0.

Compound 351:

351 was prepared in three synthetic steps from 3,4-dimethoxy-5-nitrobenzoic acid, according to the following procedure:

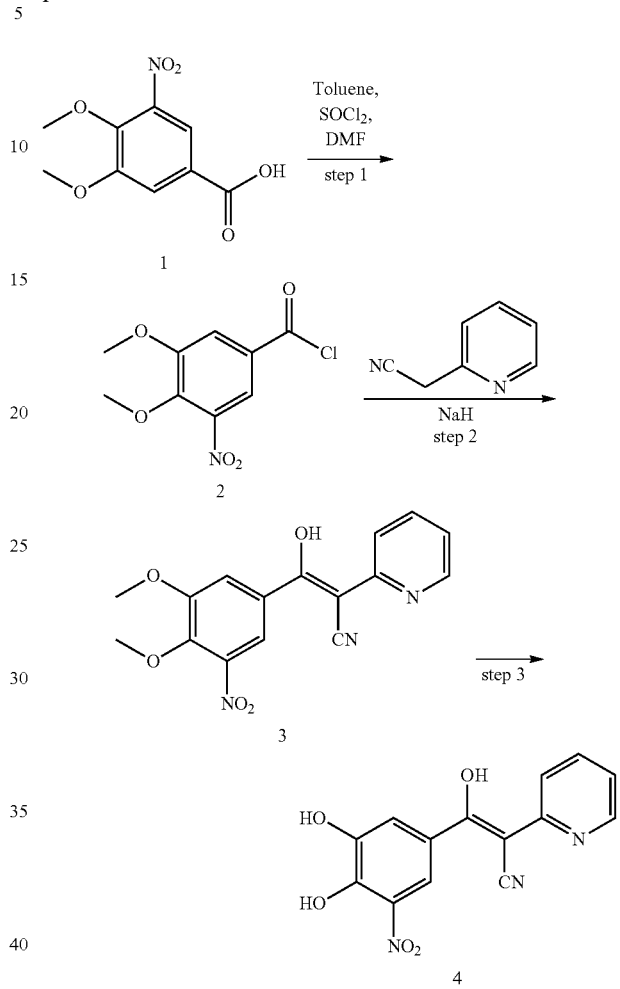

Step1: Synthesis of 3,4-dimethoxy-5-nitrobenzoyl Chloride (2)

Under a nitrogen atmosphere, SOCl₂ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. for 15 hours. The solvent was removed under reduced pressure. The resulting yellowish solid (500 mg, 92%) was used in the next step without further workup.

Step2: Synthesis of 3-(3,4-dimethoxy-5-nitrophenyl)-3-oxo-2-(pyridin-2-yl)propanenitrile (3)

Under a nitrogen atmosphere, NaH (60% w/w, 176 mg, 4.4 mmol) was added to solution of 2-(pyridin-2-yl)acetonitrile (236 mg, 2.0 mmol) in anhydrous THF (10 mL) at −5° C. The resulting suspension was stirred at −5° C. for 15 min and the solution of 3,4-dimethoxy-5-nitrobenzoyl chloride (500 mg, 2.2 mmol) in THF (5 mL) was added over 10 min and stirred for an additional 1 hour at −5° C. The reaction mixture was warmed to 0° C., quenched by the addition of 1N.HCl solution (4 mL) and stirred for 10 min at room temperature. The mixture was extracted with ethyl acetate (25 mL×2). The combined organic layers were dried with anhydrous sodium sulfate and concentrated in vacuo to give the desired product (425 mg, 64%). MS [MH]+ calcd for $C_{16}H_{14}N_3O_5$ 328.09, found 328.1.

Step3: Synthesis of 3-(3,4-dihydroxy-5-nitrophenyl)-3-oxo-2-(pyridin-2-yl)propanenitrile (4)

A solution of 3-(3,4-dimethoxy-5-nitrophenyl)-3-oxo-2-(pyridin-2-yl)propanenitrile (425 mg, 1.3 mmol) in dichloromethane (5 mL) was added 1.0 M solution of $BBr_3$ in dichloromethane (10 mL, 10 mmol) at −15° C. under a nitrogen atmosphere. The resulting suspension was stirred for 1 hours at −15° C. and allowed to warm to room temperature for overnight. The reaction was quenched slowly by the addition of water (4 mL) and stirred for another 30 min. The aqueous phase was extracted with ethyl acetate (30 mL×3). The organic layers were combined, washed with brine and dried over with anhydrous sodium sulfate. The solvent was removed under reduced pressure to give the crude product. Further purification was conducted by Prep-HPLC to obtain the desired product (65 mg, 17%). $^1$H-NMR (400 MHz, DMSO-d$^6$) δ(ppm) 16.11 (s, 1H), 10.65 (s, 2H), 8.38 (t, J=5.7 Hz, 1H), 8.28-7.96 (m, 1H), 7.84 (d, J=2.0 Hz, 1H), 7.55 (d, J=2.1 Hz, 1H), 7.47 (d, J=8.7 Hz, 1H), 7.26 (t, J=6.6 Hz, 1H). MS [MH]+ calcd for $C_{14}H_{10}N_3O_5$ 300.05, found 300.0.

Compound 371:

371 was prepared in two synthetic steps from 2-cyanoacetyl chloride, according to the following procedure:

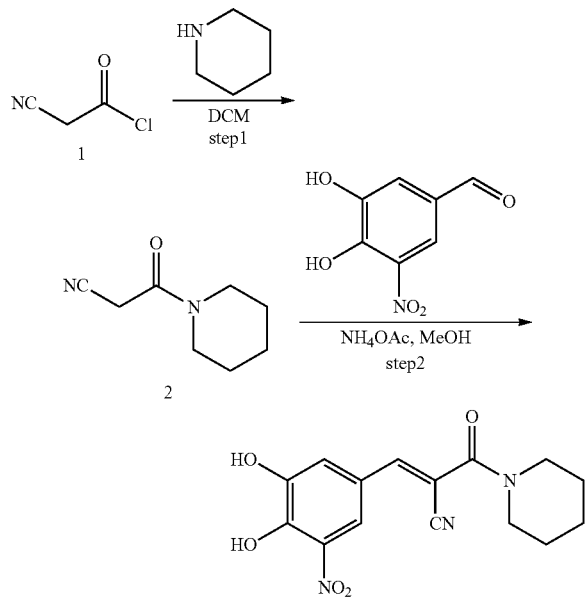

Step1: Synthesis of 3-oxo-3-(piperidin-1-yl)propanenitrile (2)

A mixture of piperidine (5 mL, 50.6 mmol), in DCM (25 mL) was added 2-cyanoacetyl chloride (5 mL) at 0° C., then warmed to room temperature overnight. The reaction mixture was quenched by $H_2O$, and concentrated in vacuo to dryness, the residue was purified by column chromatography (SiO$_2$, PE/EA=1/1) to give the 3-oxo-3-(piperidin-1-yl)propanenitrile as a yellow oil (500 mg, 7%). MS [MH]+ calcd for $C_8H_{12}N_2O$ 153.1, found 153.1.

Step2: Synthesis of (E)-3-(3,4-dihydroxy-5-nitrophenyl)-2-(piperidine-1-carbonyl)acrylonitrile (3)

A solution of 3-oxo-3-(piperidin-1-yl)propanenitrile (300 mg, 2 mmol), 3,4-dihydroxy-5-nitrobenzaldehyde (273 mg, 1.5 mmol) and NH$_4$OAc (924 mg, 12 mmol) in MeOH (15 mL) was heated to reflux for 3 hours. The solid was filtered and washed by MeOH and H$_2$O to give the crude product. The solid dissolved in MeOH (5 mL) was added 1N.HCl (0.5 mL), the color was changed and the solid was formed, the solid was filtered and washed by H$_2$O, dried in vacuo to give the (E)-3-(3,4-dihydroxy-5-nitrophenyl)-2-(piperidine-1-carbonyl)acrylonitrile as a bright yellow solid (60 mg, 13%). $^1$H NMR (400 MHz, DMSO) δ 10.86 (s, 2H), 7.92 (d, J=2.1 Hz, 1H), 7.75 (d, J=2.0 Hz, 1H), 7.63 (s, 1H), 3.56-3.45 (m, 4H), 1.55-1.62 (m, 6H). MS [MH]+ calcd for $C_{15}H_{15}N_3O_5$ 318.3, found 318.0.

Compound 518:

518 was prepared in two synthetic steps from 2-(pyridin-3-yl)acetonitrile, according to the following procedure:

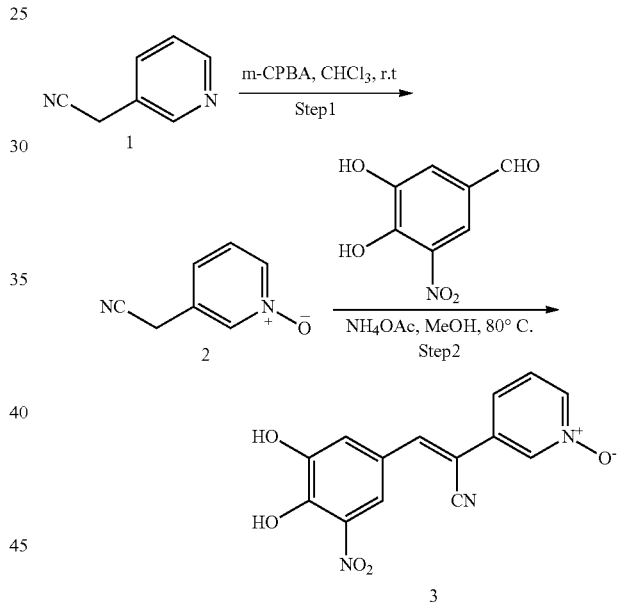

Step1: Synthesis of 3-(cyanomethyl)pyridine 1-oxide (2)

A solution of 2-(pyridin-3-yl)acetonitrile (625 mg, 5.3 mmol) and m-CPBA (1.36 g, 7.95 mmol) in CHCl$_3$ (20 mL) was stirred at room temperature for overnight. The reaction mixture was quenched by sat.NaHCO$_3$ and extracted by DCM and MeOH (DCM/MeOH=10/1). The combined organic layers were dried over anhydrous Na$_2$SO$_4$, filtered and dried in vacuo to give the crude product as a white solid (780 mg, >100%), which was used to the next step without further purification. MS [MH]+ calcd for $C_7H_6N_2O$ 135.0 found 135.0.

Step2: Synthesis of (E)-3-(1-cyano-2-(3,4-dihydroxy-5-nitrophenyl)vinyl)pyridine 1-oxide (3)

A solution of 3-(cyanomethyl)pyridine 1-oxide (400 mg, 3.0 mmol), 3,4-dihydroxy-5-nitro-benzaldehyde (270 mg, 1.5 mmol) and NH₄OAc (693 mg, 9 mmol) in MeOH (10 mL) was heated to reflux for overnight. LCMS showed no 3,4-dihydroxy-5-nitrobenzaldehyde left. The reaction mixture was cooled to room temperature. The solid was filtered and washed by MeOH and H₂O. The solid was re-dissolved in MeOH (5 mL). 5 mL of 1N aqueous HCl was added to adjust pH 3~4. The desired product was obtained by filter as a bright solid (110 mg, 18%). ¹H NMR (301 MHz, DMSO) δ 13.71 (s, 1H), 10.89 (s, 2H), 8.65 (s, 1H), 8.26 (d, J=6.2 Hz, 1H), 8.14 (s, 1H), 7.99 (d, J=2.0 Hz, 1H), 7.84 (d, J=2.0 Hz, 1H), 7.67-7.50 (m, 2H). MS [MH]⁺ calcd for C₁₄H₉N₃O₅ 300.0 found 300.0.

Compound 523:

523 was prepared in three synthetic steps from 3,4-dimethoxy-5-nitrobenzoic acid, according to the following procedure:

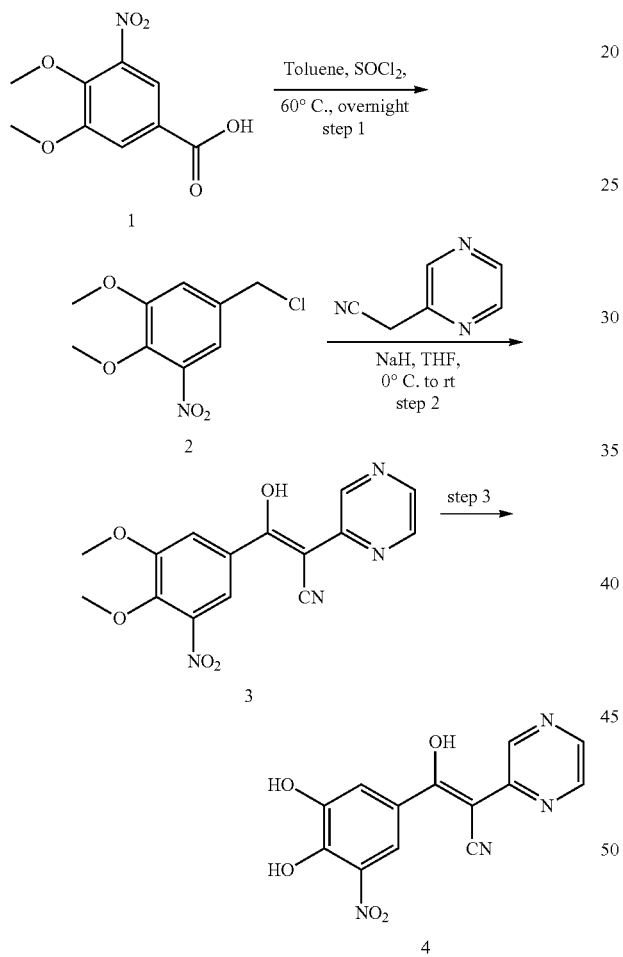

Step1: Synthesis of 3,4-dimethoxy-5-nitrobenzoyl Chloride (2)

Under a nitrogen atmosphere, SOCl₂ (0.76 mL, 10.56 mmol) and anhydrous DMF (0.02 mL, 0.44 mmol) were added to a suspension of 3,4-dimethoxy-5-nitrobenzoic acid (1 g, 4.4 mmol) in toluene (20 mL) at room temperature. The mixture was heated at 60° C. and stirred for 15 hours. The solvent was removed under reduced pressure. The resulting yellowish solid 3,4-dimethoxy-5-nitrobenzoyl chloride (1 g, 93%) was used in the next step without further workup.

Step2: Synthesis of 3-(3,4-dimethoxy-5-nitrophenyl)-3-hydroxy-2-(pyrazin-2-yl)acrylonitrile (3)

Under a nitrogen atmosphere, 60% NaH (336 mg, 8.4 mmol) was added to solution of 2-(pyrazin-2-yl)acetonitrile (500 mg, 4.2 mmol) in anhydrous THF (5 mL) at −5° C. The resulting suspension was stirred at −5° C. for 15 min and the THF solution of 3,4-dimethoxy-5-nitrobenzoyl chloride (500 mg, 4.07 mmol) was added over 10 min and stirred for an additional 1 hour at −5° C. The reaction mixture was warmed to 0° C., quenched by the addition of 1N.HCl solution (8 mL) and stirred for 10 min at room temperature, then extracted with ethyl acetate (30 mL×3), the organic layer was dried with anhydrous sodium sulfate and concentrated in vacuo to obtain the desired product (440 mg, 33%). MS [MH]⁻ calcd for C₁₅H₁₁N₄O₅ 327.08, found 327.1.

Step3: Synthesis of 3-(3,4-dihydroxy-5-nitrophenyl)-3-hydroxy-2-(pyrazin-2-yl)acrylonitrile (4)

To a solution of 3-(3,4-dimethoxy-5-nitrophenyl)-3-hydroxy-2-(pyrazin-2-yl)acrylonitrile (200 mg, 0.61 mmol) in anhydrous dichloromethane (5 mL) was added 1.0 M solution of BBr₃ in dichloromethane (3 mL, 3 mmol) at −15° C. under a nitrogen atmosphere. The resulting suspension was stirred for 1 hour at −15° C. and allowed to warm to room temperature for overnight. The reaction was quenched by the addition of water (2 mL) and stirred for another 30 min. The aqueous phase was extracted with ethyl acetate (30 mL×3). The organic layers were combined, washed with brine and dried over anhydrous sodium sulfate. The solvent was removed under reduced pressure to give the crude product. Further purification was conducted by Prep-HPLC to obtain the desired product (35 mg, 19%). ¹H-NMR (400 MHz, DMSO-d⁶)δ(ppm) 15.85 (s, 1H), 10.75 (s, 2H), 8.88 (s, 1H), 8.34 (d, J=3.7 Hz, 1H), 8.22 (d, J=2.5 Hz, 1H), 7.88 (d, J=2.1 Hz, 1H), 7.56 (d, J=2.1 Hz, 1H). MS [MH]⁻ calcd for C₁₃H₇N₄O₅ 299.05, found 299.0.

Compound 525:

525 was prepared in two synthetic steps from 3,4-dimethoxy-5-nitrobenzoic acid, according to the following procedure:

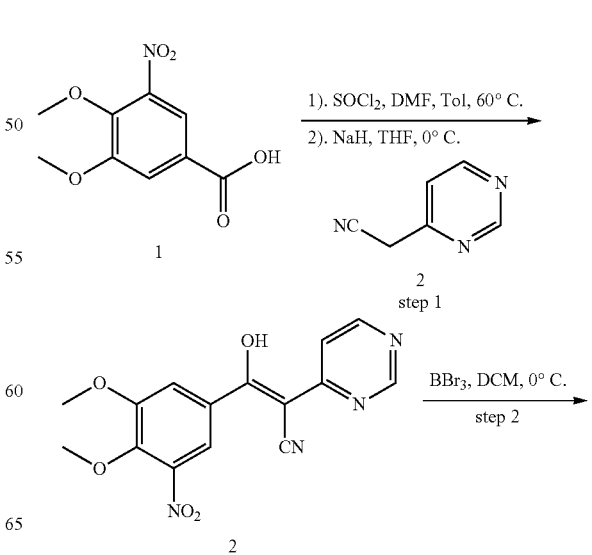

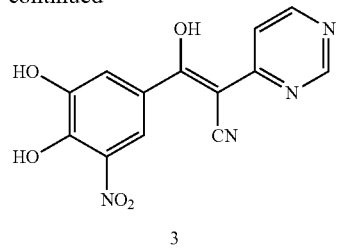

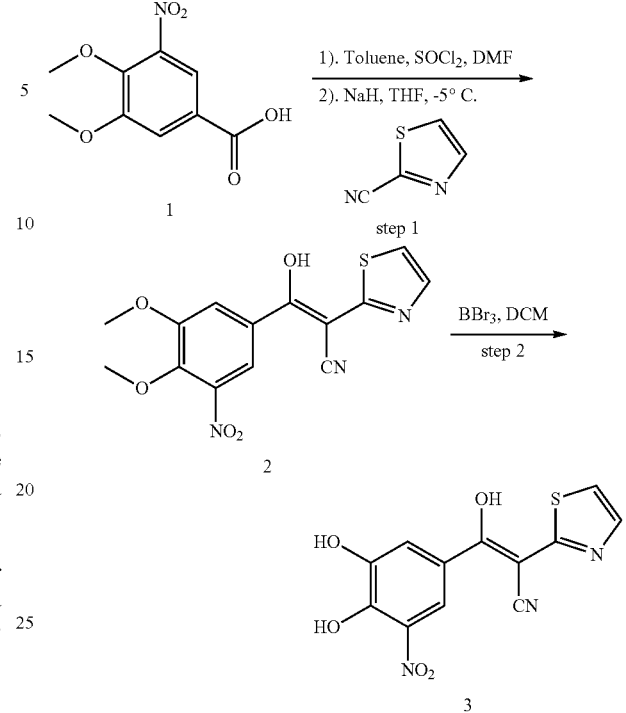

Step1: Synthesis of (E)-3-(3,4-dimethoxy-5-nitrophenyl)-3-hydroxy-2-(pyrimidin-4-yl)acrylonitrile (2)

Under a nitrogen atmosphere, SOCl$_2$ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. and stirred for 15 hours. The organic solvent was eliminated by distillation under reduced pressure. More touene was added and eliminated again. The resulting yellowish solid 3,4-dimethoxy-5-nitrobenzoyl chloride was dissolved in anhydrous THF (5 mL).

Under a nitrogen atmosphere, 60% NaH (0.18 g, 4.4 mmol) was added to solution of 2-(pyrimidin-4-yl)acetonitrile (0.44 g, 2.0 mmol) in anhydrous THF (10 mL) at −5° C. The resulting suspension was stirred at −5° C. for 15 min and the THF solution of 3,4-dimethoxy-5-nitrobenzoyl chloride was added over 10 min and stirred for an additional 1 hour at −5° C. The reaction mixture was warmed to 0° C., quenched by the addition of 1N.HCl solution (4 mL) and stirred for 10 min at room temperature, extracted by ethyl acetate (25 mL×2), the organic layers was dried with Na$_2$SO$_4$ and concentrated in vacuo to give the title compound as an orange solid (550 mg, 85%). MS [MH]$^+$ calcd for C$_{15}$H$_{12}$N$_4$O$_5$ 329.0 found 329.0.

Step2: Synthesis of (E)-3-(3,4-dihydroxy-5-nitrophenyl)-3-hydroxy-2-(pyrimidin-4-yl)acrylonitrile (3)

A solution of (E)-3-(3,4-dimethoxy-5-nitrophenyl)-3-hydroxy-2-(pyrimidin-4-yl)acrylonitrile (250 mg, 0.76 mmol) in DCM (5 mL) was added BBr$_3$ (0.5 mL, 5 mmol) at −5° C. under a nitrogen atmosphere. The resulting red suspension was stirred for 1 h at −5° C. and allowed to warm to room temperature overnight. The reaction was quenched by the addition of H$_2$O (2 mL) and stirred for 30 min. The aqueous phase was extracted with ethyl acetate (30 mL×3). The organic layers were combined, washed with brine and dried over Na$_2$SO$_4$. The solvent was eliminated under reduced pressure to give the crude product. Further purification by Prep-HPLC (0.5% TFA, MeOH/H$_2$O) gave the desired product as a bright yellow solid (46 mg, 19%). $^1$H NMR (400 MHz, DMSO) δ 15.35 (s, 1H), 10.67 (s, 2H), 8.95-7.16 (m, 5H). MS [MH]$^+$ calcd for C$_{15}$H$_{14}$N$_2$O$_5$ 337.0 found 301.0 (free).

Compound 503:

503 was prepared in two synthetic steps from 3,4-dimethoxy-5-nitrobenzoic acid, according to the following procedure:

It Step1: Synthesis of 3-(3,4-dimethoxy-5-nitrophenyl)-3-oxo-2-(thiazol-2-yl)propanenitrile (2)

Under a nitrogen atmosphere, SOCl$_2$ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. and stirred for 15 hours. The organic solvent was eliminated by distillation under reduced pressure. More toluene was added and eliminated again. The resulting yellowish solid 3,4-dimethoxy-5-nitrobenzoyl chloride was dissolved in anhydrous THF (5 mL).

Under a nitrogen atmosphere, 60% NaH (0.18 g, 4.4 mmol) was added to the solution of 2-(thiazol-2-yl) acetonitrile (0.24 g, 2.0 mmol) in anhydrous THF (5 mL) at −5° C. The resulting suspension was stirred at −5° C. for 15 min and the solution of 3,4-dimethoxy-5-nitrobenzoyl chloride in THF was added over 10 min and stirred for an additional 1 hour at −5° C. The reaction mixture was warmed to 0° C., quenched by the addition of 1N.HCl solution (4 mL) and stirred for 10 min at room temperature, extracted by ethyl acetate (25 mL*2), the organic layers was dried with Na$_2$SO$_4$ and concentrated in vacuo to give the title compound as an orange solid (240 mg, 39%). MS [MH]$^+$ calcd for C$_{14}$H$_{11}$N$_3$O$_5$S 334.3, found 334.3.

Step2: Synthesis of 3-(3,4-dihydroxy-5-nitrophenyl)-3-oxo-2-(thiazol-2-yl)propanenitrile (3)

A solution of 3-(3,4-dimethoxy-5-nitrophenyl)-3-oxo-2-(thiazol-2-yl)propanenitrile (224 mg, 0.67 mmol) in DCM (5 mL) was added 1.0 M solution of BBr$_3$ in DCM (3 mL, 3 mmol) at −15° C. under nitrogen atmosphere. The resulting red suspension was stirred for 1 hour at −15° C. and allowed to warm to room temperature overnight. The reaction was quenched by the addition of H₂O (2 mL) and stirred for 30 min. The aqueous phase was extracted with ethyl acetate (30 mL×3). The organic layers were combined, washed with brine and dried over Na₂SO₄. The solvent was eliminated under reduced pressure to give the crude product. Further purification by Prep-HPLC (0.5% TFA, MeOH/H₂O) gave the desired product as a bright yellow solid (24 mg, 12%). ¹H NMR (400 MHz, DMSO) δ 7.88 (d, J=2.0 Hz, 1H), 7.60 (d, J=4.0 Hz, 1H), 7.56 (d, J=2.0 Hz, 1H), 7.31 (d, J=4.0 Hz, 1H). MS [MH]⁻ calcd for C₁₂H₇N₃O₅S 304.0, found 304.0.

Compound 374:

374 was prepared in two synthetic steps from 3,4-dimethoxy-5-nitrobenzoic acid, according to the following procedure:

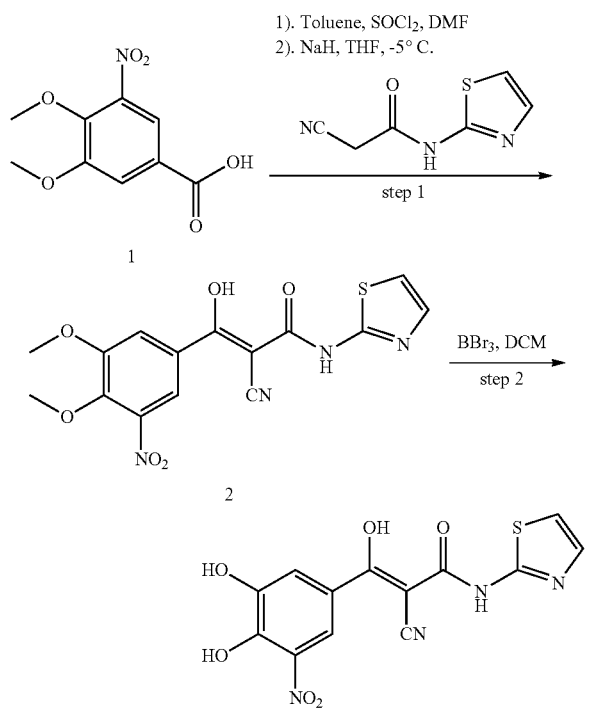

Step1: Synthesis of 2-cyano-3-(3,4-dimethoxy-5-nitrophenyl)-3-oxo-N-(thiazol-2-yl)propanamide (2)

Under a nitrogen atmosphere, SOCl₂ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. and stirred for 15 hours. The organic solvent was eliminated by distillation under reduced pressure. More touene was added and eliminated again. The resulting yellowish solid 3,4-dimethoxy-5-nitrobenzoyl chloride was dissolved in anhydrous THF (5 mL).

Under a nitrogen atmosphere, 60% NaH (0.18 g, 4.4 mmol) was added to solution of 2-cyano-N-(thiazol-2-yl)acetamide (0.35 g, 2.0 mmol) in anhydrous THF (10 mL) at −5° C. The resulting suspension was stirred at −5° C. for 15 min and the THF solution of 3,4-dimethoxy-5-nitrobenzoyl chloride was added over 10 min and stirred for an additional 1 hour at −5° C. The reaction mixture was warmed to 0° C., quenched by the addition of 1N.HCl solution (4 mL) and stirred for 10 min at room temperature, extracted by ethyl acetate (25 mL×2), the organic layers was dried with Na₂SO₄ and concentrated in vacuo to give the title compound as an orange solid (510 mg, 67%). MS [MH]⁺ calcd for C₁₅H₁₂N₄O₆S 377.0, found 377.0.

Step2: Synthesis of 2-cyano-3-(3,4-dihydroxy-5-nitrophenyl)-3-oxo-N-(thiazol-2-yl)propanamide (3)

A solution of 2-cyano-3-(3,4-dimethoxy-5-nitrophenyl)-3-oxo-N-(thiazol-2-yl)propanamide (400 mg, 1.1 mmol) in DCM (5 mL) was added 1.0 M solution of BBr₃ in DCM (5 mL, 5 mmol) at −15° C. under a nitrogen atmosphere. The sesulting red suspension was stirred for 1 h at −15° C. and allowed to warm to room temperature overnight. The reaction was quenched by the addition of H₂O (2 mL) and stirred for 30 min. The aqueous phase was extracted with ethyl acetate (30 mL×3). The organic layers were combined, washed with brine and dried over Na₂SO₄. The solvent was eliminated under reduced pressure to give the crude product. Further purification by Prep-HPLC (0.5% TFA, MeOH/H₂O) gave the desired product as a bright yellow solid (100 mg, 28%). ¹H NMR (400 MHz, DMSO) δ 7.88 (d, J=2.0 Hz, 1H), 7.60 (d, J=4.0 Hz, 1H), 7.56 (d, J=2.0 Hz, 1H), 7.31 (d, J=4.0 Hz, 1H). MS [MH]⁺ calcd for C₁₃H₈N₄O₆S 349.0, found 349.0.

Compound 655:

655 was prepared in four synthetic steps from methyl 5-chloropyrazine-2-carboxylate, according to the following procedure:

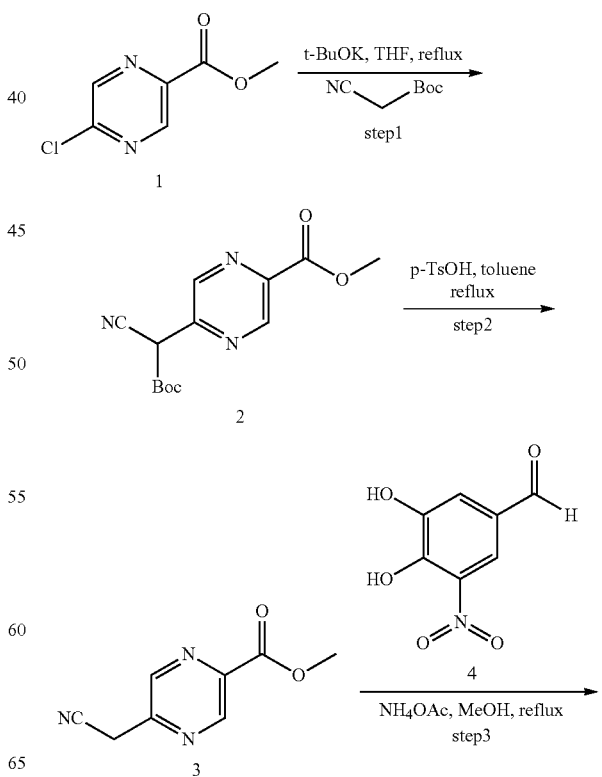

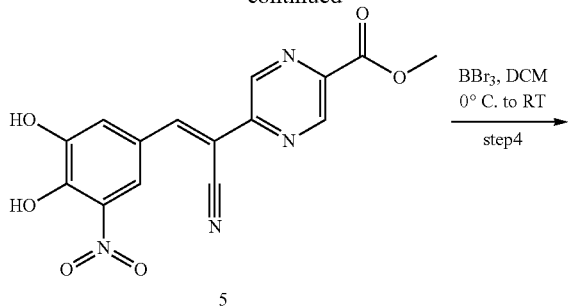

Step1: Synthesis of Methyl 5-(2-(tert-butoxy)-1-cyano-2-oxoethyl)pyrazine-2-carboxylate (2)

A solution of tert-butyl 2-cyanoacetate (2.1 g, 15 mmol) and t-BuOK (1.6 g, 15 mmol) in dry THF (50 mL) stirred at rt for 30 min, then methyl 5-chloropyrazine-2-carboxylate (1.7 g, 10.0 mmol) was added, the reaction mixture was heated to reflux overnight, After the reaction was completed, cooled it to rt and quenched by H$_2$O (100 mL), the solid was filtered and dried in vacuo to afford the desired product as yellow solid (1.7 g, 61%). MS [M+H]$^+$ calcd for C$_{13}$H$_{15}$N$_3$O$_4$ 278.1, found 278.1.

Step2: Synthesis of Methyl 5-(cyanomethyl)pyrazine-2-carboxylate (3)

A solution of 5-(2-(tert-butoxy)-1-cyano-2-oxoethyl)pyrazine-2-carboxylate (1.7 g, 6.14 mmol) and p-TsOH (314 mg, 1.84 mmol) was heated to reflux for 3 h, then TLC showed no starting materials left. The reaction mixture was quenched by H$_2$O (5 mL), extracted by EA, washed with sat. NaHCO$_3$, the organic layer was dried with Na$_2$SO$_4$, filtered and dried in vacuo to afford the crude product, further purification by column chromatography (SiO$_2$, 100 g, 200-300m, eluted by PE/EA=5/1) to afford the desired product methyl 5-(cyanomethyl)pyrazine-2-carboxylate (800 mg, 74%) as yellow solid. MS [M+H]$^+$ calcd for C$_8$H$_7$N$_3$O$_2$ 178.1ound 178.1.

Step3: Synthesis of Methyl (Z)-methyl 5-(1-cyano-2-(3,4-dihydroxy-5-nitrophenyl)vinyl)pyrazine-2-carboxylate (4)

A solution of methyl 5-(cyanomethyl)pyrazine-2-carboxylate (170 mg, 1.0 mmol), 3,4-dihydroxy-5-nitrobenzaldehyde (183 mg, 1.0 mmol) and NH$_4$OAc (554 mg, 7.2 mmol) in MeOH (15 mL) was heated to reflux for 3 hours, then cooled it to room temperature. The solid was filtered and washed by H$_2$O (15 mL), The solid was re-dissolved in MeOH (5 mL). 5 mL of 1N aqueous HCl was added to till pH=3-4. The desired product was obtained by filter and dried in vacuo as bright solid (210 mg, 61%). MS [M+H]$^+$ calcd for C$_{15}$H$_{10}$N$_4$O$_6$ 343.0, found 343.0.

Step4: Synthesis of (Z)-5-(1-cyano-2-(3,4-dihydroxy-5-nitrophenyl)vinyl)pyrazine-2-carboxylic Acid (5)

A solution of (Z)-methyl 5-(1-cyano-2-(3,4-dihydroxy-5-nitrophenyl)vinyl)pyrazine-2-carboxylate (150 mg, 0.44 mmol) in DCM (5 mL) was added 1.0 M solution of BBr$_3$ in DCM (2 mL, 2 mmol) at −15° C. under a nitrogen atmosphere. The suspension was stirred for 1 hour at −15° C. and allowed to warm to room temperature overnight. The reaction was quenched by the addition of H$_2$O (2 mL) and stirred for 30 min. The aqueous phase was extracted with ethyl acetate (30 mL×3). The organic layers were combined, washed with brine and dried with Na$_2$SO$_4$. The solvent was eliminated in vacuo to give the crude product. Further purification by Prep-HPLC (0.5% TFA, MeOH/H$_2$O) gave the desired product as bright yellow solid (55 mg, 38%). $^1$H NMR (300 MHz, DMSO) δ 9.27 (s, 1H), 9.22 (s, 1H), 8.57 (s, 1H), 8.12 (s, 1H), 7.98 (s, 1H), 2.52 (s, 19H), 0.02 (s, 1H). MS [MH]$^+$ calcd for C$_{14}$H$_8$N$_4$O$_6$ 329.0, found 329.0.

Compound 656:

656 was prepared in two synthetic steps from 5-chloro-1,2,4-thiadiazole, according to the following procedure:

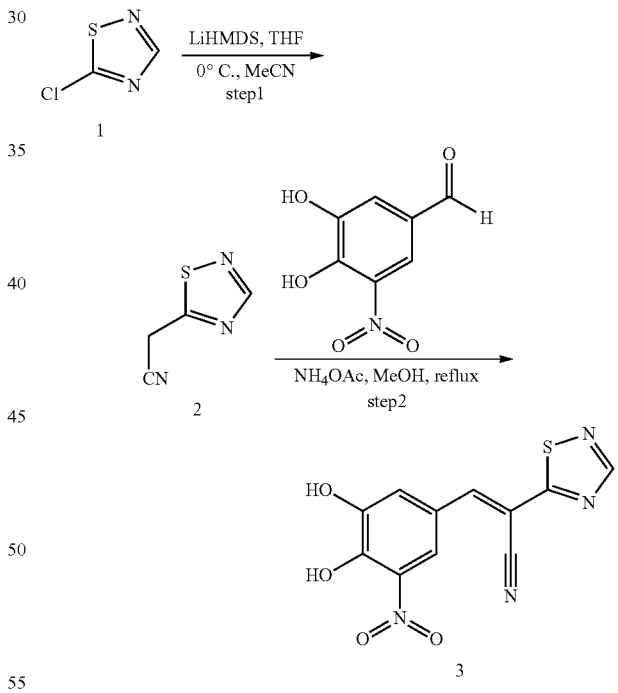

Step1: Synthesis of 2-(1,2,4-thiadiazol-5-yl)acetonitrile (2)

A solution of dry MeCN (226 mg, 11 mmol) in dry THF (25 ml) was added LiHMDS (5.5 mmol, 5.5 mL) at 0° C., then the mixture was stirred at 0° C. for 30 min, 5-chloro-1,2,4-thiadiazole (691 mg, 5.5 mmol) in dry THF (5 mL) was added to the mixture at 0° C., then stirred at rt overnight. The reaction mixture was quenched by H$_2$O (1 mL), and extracted by EA (30 mL×3), dried with Na$_2$SO$_4$, filtered and dried in vacuo to afford the crude product. Further purification by column chromatography (SiO$_2$, 100 g, 200-300 m, eluted by PE/EA=5:1) gave the desired product (410 mg, 60%) as yellow solid. MS [M+H]$^+$ calcd for C$_4$H$_3$N$_3$S 126.0, found 126.0.

Step2: Synthesis of (E)-3-(3,4-dihydroxy-5-nitrophenyl)-2-(1,2,4-thiadiazol-5-yl)acrylonitrile (3)

A solution of 2-(1,2,4-thiadiazol-5-yl)acetonitrile (150 mg, 1.2 mmol), 3,4-dihydroxy-5-nitrobenzaldehyde (182 mg, 1 mmol) and NH$_4$OAc (462 mg, 6 mmol) in MeOH (10 mL) was heated to reflux for 5 hours. LC-MS showed no starting materials left. The solid was filtered and washed by MeOH and H$_2$O, then dissolved in MeOH (5 mL). 5 ml of 1N.HCl was added till pH=3-4. The solid was filtered and dried in vacuo to give the desired product as bright yellow solid (200 mg, 69%). $^1$H NMR (400 MHz, DMSO) δ 10.96 (s, 1H), 8.97 (s, 1H), 8.45 (s, 1H), 8.14 (d, J=2.1 Hz, 1H), 7.95 (d, J=2.2 Hz, 1H). MS [M+H]$^+$ calcd for C$_{11}$H$_6$N$_4$O$_4$S 291.0, found 291.0.

Compound 660:

660 was prepared in two synthetic steps from (E)-2-cyano-3-(3,4-dihydroxy-5-nitrophenyl)acrylic acid, according to the following procedure:

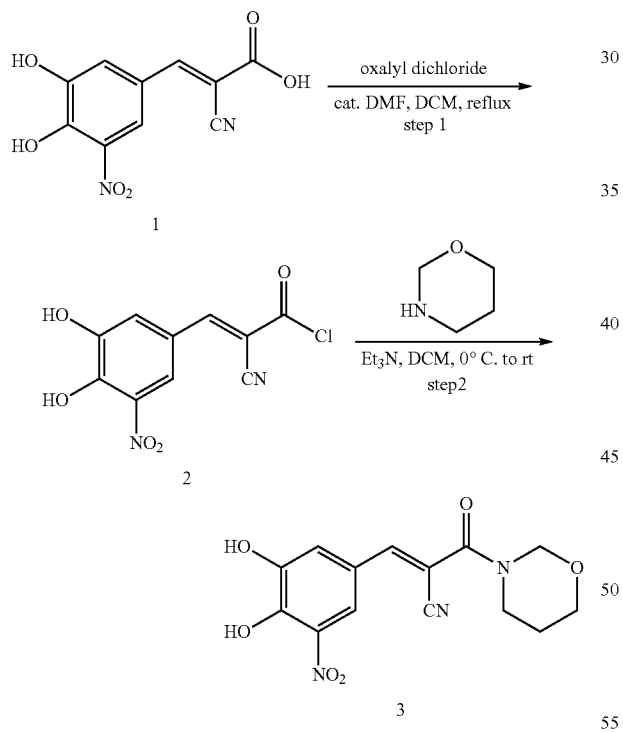

Step1: Synthesis of (E)-2-cyano-3-(3,4-dihydroxy-5-nitrophenyl)acryloyl Chloride (2)

A solution of (E)-2-cyano-3-(3,4-dihydroxy-5-nitrophenyl)acrylic acid (25 mg, 0.1 mmol) in DCM (25 ml) was added a drop of DMF and oxalyl dichloride (25 mg, 0.2 mmol). The reaction mixture was heated till the solid dissolved, cooled to rt, concentrated in vacuo to dryness. It was used in the next step without purification (27 mg, 100%).

Step2: Synthesis of (E)-3-(3,4-dihydroxy-5-nitrophenyl)-2-(1,3-oxazinane-3-carbonyl)acrylonitrile (3)

A solution of 1,3-oxazinane (9 mg, 0.12 mmol), Et$_3$N (24 mg, 0.24 mmol) in DCM (3 mL) was added acyl chloride dissolved in DCM (3 mL) dropwise at 0° C., when the addition was completed, the reaction mixture was slowly warmed to rt overnight. The reaction mixture was quenched by H$_2$O, separated the organic layer, and dried with Na$_2$SO$_4$, concentrated in vacuo to afford the crude product, further purification by Prep-HPLC (0.5% TFA, MeOH/H$_2$O) afford the desired product as yellow solid (5 mg, 16%). 1H NMR (400 MHz, DMSO) δ 10.87 (s, 2H), 7.95 (d, J=2.0 Hz, 1H), 7.76 (d, J=2.1 Hz, 1H), 7.69 (s, 1H), 5.01 (s, 2H), 3.88-3.84 (m, 2H), 3.74 (s, 2H), 1.72-1.66 (m, 2H). MS [M+H]+ calcd for C$_{14}$H$_{14}$N$_3$O$_6$ 320.1 found. 319.9

Compound 661:

661 was prepared in two synthetic steps from 3,4-dimethoxy-5-nitrobenzoic acid, according to the following procedure:

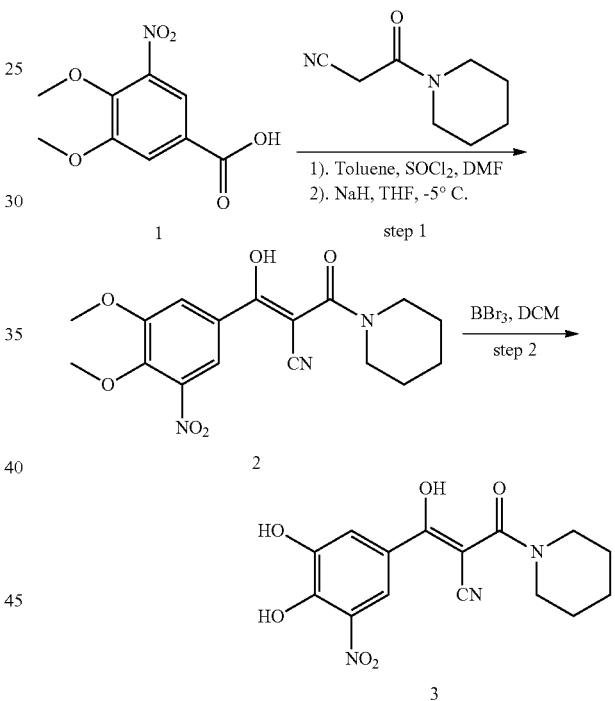

Step1: Synthesis of (Z)-3-(3,4-dimethoxy-5-nitrophenyl)-3-hydroxy-2-(piperidine-1-carbonyl) acrylonitrile (2)

Under a nitrogen atmosphere, SOCl$_2$ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. and stirred for 15 hours. The organic solvent was eliminated by distillation under reduced pressure. More toluene was added and eliminated again. The resulting yellowish solid 3,4-dimethoxy-5-nitrobenzoyl chloride was dissolved in anhydrous THF (5 mL).

Under a nitrogen atmosphere, 60% NaH (0.18 g, 4.4 mmol) was added to the solution of 3-oxo-3-(piperidin-1- yl)propanenitrile (0.30 g, 2.0 mmol) in anhydrous THF (5 mL) at −5° C. The resulting suspension was stirred at −5° C. for 15 min and the solution of 3,4-dimethoxy-5-nitrobenzoyl chloride in THF was added over 10 min and stirred for an additional 1 hour at −5° C. The reaction mixture was warmed to 0° C., quenched by the addition of 1N.HCl solution (4 mL) and stirred for 10 min at room temperature, extracted by ethyl acetate (25 mL*2), the organic layers was dried with $Na_2SO_4$ and concentrated in vacuo to give the title compound 3 as an orange solid (260 mg, 36%). MS [MH]$^+$ calcd for $C_{17}H_{20}N_3O_6$ 362.1, found 362.1.

Step2: Synthesis of (Z)-3-(3,4-dihydroxy-5-nitrophenyl)-3-hydroxy-2-(piperidine-1-carbonyl)acrylonitrile (3)

A solution of (Z)-3-(3,4-dimethoxy-5-nitrophenyl)-3-hydroxy-2-(piperidine-1-carbonyl)acrylonitrile (180 mg, 0.5 mmol) in DCM (5 mL) was added 1.0 M solution of $BBr_3$ in DCM (3 mL, 3 mmol) at −15° C. under nitrogen atmosphere. The resulting red suspension was stirred for 1 hour at −15° C. and allowed to warm to room temperature overnight. The reaction was quenched by the addition of $H_2O$ (2 mL) and stirred for 30 min. The aqueous phase was extracted with ethyl acetate (30 mL×3). The organic layers were combined, washed with brine and dried with $Na_2SO_4$. The solvent was eliminated under reduced pressure to give the crude product. Further purification by Prep-HPLC (0.5% TFA, MeOH/$H_2O$) gave the desired product as yellow solid (63 mg, 38%).1H NMR (400 MHz, DMSO) δ 10.96 (s, 1H), 7.87 (d, J=2.0 Hz, 1H), 7.49 (s, 1H), 3.65 (s, 4H), 1.60 (s, 6H). MS [M−H]-calcd for $C_{15}H_{16}N_3O_6$ 334.1, found 333.9.

Compound 666:

666 was prepared in two synthetic steps from 3,4-dimethoxy-5-nitrobenzoic acid, according to the following procedure:

Step1: Synthesis of 2-(cyanomethyl)thiazole-4-carboxylic Acid (3)

Under a nitrogen atmosphere, 3-bromo-2-oxopropanoic acid in dry THF (5 mL) was added to a suspension of 2-cyanoethanethioamide (1.2 g, 12 mmol) in THF (20 ml) at 0° C. The mixture was heated at 70° C. and stirred for 3 hours. The aqueous phase was extracted with ethyl acetate (30 mL×3). The organic layers were combined, washed with brine and dried with $Na_2SO_4$. The solvent was eliminated under reduced pressure to give the crude product. Further purification by column chromatography (SiO$_2$, 100 g, 200-300 m, eluted by PE/EA=1/1) afforded the desired product as white solid (350 mg, 18%).

Step2: Synthesis of (E)-2-(1-cyano-2-(3,4-dihydroxy-5-nitrophenyl)vinyl)thiazole-4-carboxylic Acid (4)

A solution of 2-(cyanomethyl)thiazole-4-carboxylic acid (168 mg, 1.0 mmol), 3,4-dihydroxy-5-nitrobenzaldehyde (183 mg, 1.0 mmol) and NH$_4$OAc (554 mg, 7.2 mmol) in MeOH (15 mL) was heated to reflux for 3 hours, then cooled to room temperature. The solid was filtered and washed by H$_2$O (15 mL), The solid was re-dissolved in MeOH (5 mL). 5 mL of 1N aqueous HCl was added to adjust pH 3-4. The desired product was obtained by filter and dried in vacuo as bright solid (150 mg, 45%). $^1$H NMR (400 MHz, DMSO) δ 7.98 (s, 1H), 7.91 (s, 1H), 7.84 (s, 1H), 7.15-7.75 (m, 4H). MS [MH]$^+$ calcd for $C_{13}H_7N_3O_6S$ 334.0, found 334.0.

Compound 668:

668 was prepared in three synthetic steps from 3,4-dimethoxy-5-nitrobenzoic acid, according to the following procedure:

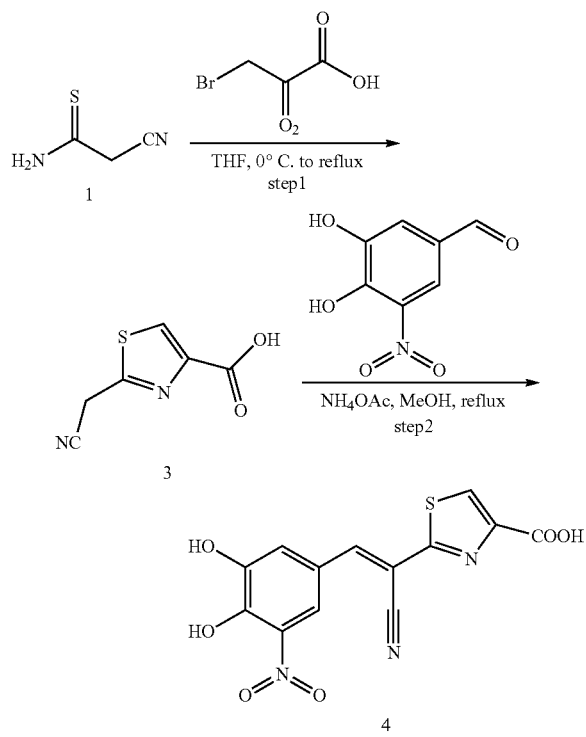

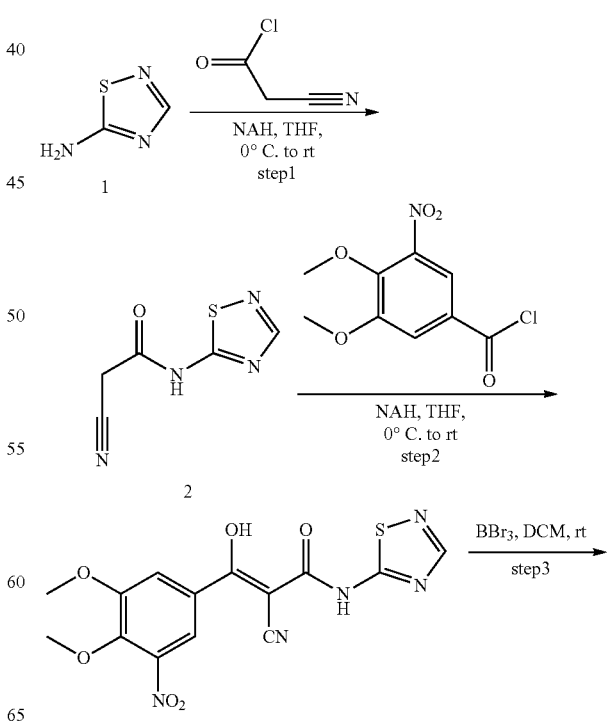

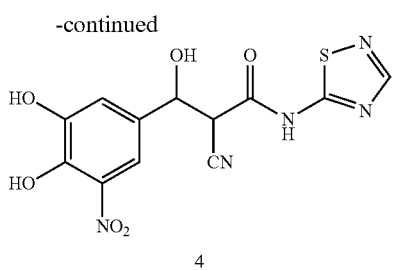

4

Step1: Synthesis of 2-cyano-N-(1,2,4-thiadiazol-5-yl)acetamide (2)

Under a nitrogen atmosphere, NaH (200 mg, 5 mmol, 60%) was added to a suspension of 1,2,4-thiadiazol-5-amine (500 mg, 5 mmol) in THF (25 mL) at 0° C. The resulting suspension was stirred at 0° C. for 15 min and the solution of 2-cyanoacetyl chloride (500 mg, 5 mmol) in THF was added over 10 min and stirred for an additional 1 h at RT, then quenched by the addition of 1N.HCl solution and stirred for 10 min at room temperature. Extracted it by ethyl acetate (25 mL×2), and the organic layers was dried with $Na_2SO_4$ and concentrated in vacuo to give the crude product. Washed it by PE/EA=1:1(5 mL) to afford the purity product (260 mg, 30%). MS $[MH]^+$ calcd for $C_5H_4N_4OS$ 169.0, found 169.0.

Step2: Synthesis of 2-cyano-3-(3,4-dimethoxy-5-nitrophenyl)-3-hydroxy-N-(1,2,4-thiadiazol-5-yl) acrylamide (3)

Under a nitrogen atmosphere, $SOCl_2$ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. and stirred for 15 hours. When the reaction was complete, the organic solvent was eliminated by distillation under reduced pressure. Additional toluene was added and eliminated again. The resulting yellowish solid 3,4-dimethoxy-5-nitrobenzoyl chloride was dissolved in anhydrous THF (5 mL).

Under a nitrogen atmosphere, 60% NaH (80 mg, 2.0 mmol) was added to solution of 2-cyano-N-(1,2,4-thiadiazol-5-yl)acetamide (250 mg, 1.5 mmol) in anhydrous THF (10 mL) at −5° C. The resulting suspension was stirred at −5° C. for 15 min and the THF solution of 3,4-dimethoxy-5-nitrobenzoyl chloride was added over 10 min and stirred for an additional 1 hour at −5° C. The reaction mixture was warmed to 0° C.; quenched by the addition of 1N.HCl solution (4 mL) and stirred for 10 min at room temperature. Extracted by ethyl acetate (25 mL×2), the organic layers was dried with $Na_2SO_4$ and concentrated in vacuo to give the title compound as orange solid (210 mg, 37%). MS $[M+H]^+$ calcd for $C_{14}H_{11}N_5O_6S$ 378.0, found 378.0.

Step3: Synthesis of 2-cyano-3-(3,4-dihydroxy-5-nitrophenyl)-3-hydroxy-N-(1,2,4-thiadiazol-5-yl) acrylamide (4)

A solution of 2-cyano-3-(3,4-dimethoxy-5-nitrophenyl)-3-hydroxy-N-(1,2,4-thiadiazol-5-yl)acrylamide (150 mg, 0.40 mmol) in DCM (5 mL) was added 1.0 M solution of $BBr_3$ in DCM (2 mL, 2 mmol) at −15° C. under a nitrogen atmosphere. The suspension was stirred for 1 hour at −15° C. and allowed to warm to room temperature overnight. The reaction was quenched by the addition of $H_2O$ (2 mL) and stirred for 30 min. The aqueous phase was extracted with ethyl acetate (30 mL×3). The organic layers were combined, washed with brine and dried with $Na_2SO_4$. The solvent was eliminated under reduced pressure to give the crude product. Further purification by Prep-HPLC (0.5% TFA, MeOH/$H_2O$) gave the desired product as bright yellow solid (50 mg, 36%). $^1H$ NMR (400 MHz, DMSO) δ 13.80 (s, 1H), 8.33 (s, 1H), 7.72 (d, J=1.8 Hz, 1H), 7.47 (d, J=1.8 Hz, 1H). MS $[MH]^+$ calcd for $C_{12}H_7N_5O_6S$ 350.0, found 350.0.

Compound 673:

673 was prepared in two synthetic steps from 3,4-dimethoxy-5-nitrobenzoic acid, according to the following procedure:

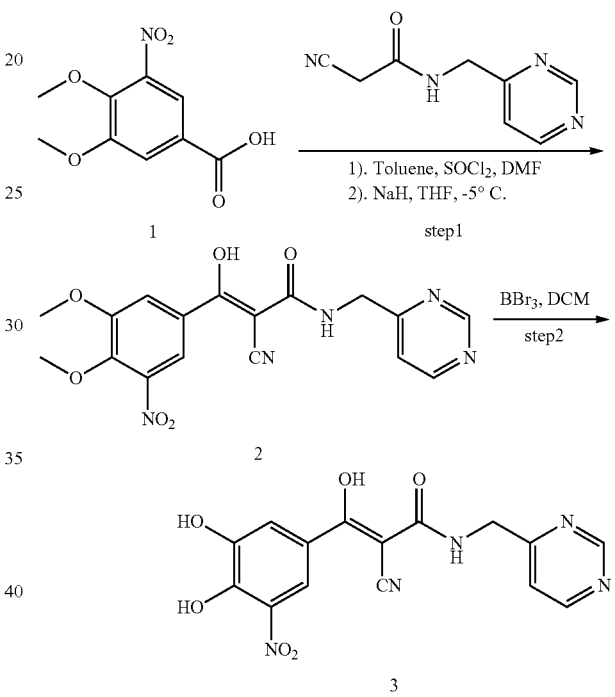

Step1: Synthesis of (Z)-2-cyano-3-(3,4-dimethoxy-5-nitrophenyl)-3-hydroxy-N-(pyrimidin-4-ylmethyl) acrylamide (2)

Under a nitrogen atmosphere, $SOCl_2$ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. and stirred for 15 hours. The organic solvent was eliminated by distillation under reduced pressure. More toluene was added and eliminated again. The resulting yellowish solid 3,4-dimethoxy-5-nitrobenzoyl chloride was dissolved in anhydrous THF (5 mL).

Under a nitrogen atmosphere, 60% NaH (0.18 g, 4.4 mmol) was added to the solution of 2-cyano-N-(pyrimidin-4-ylmethyl)acetamide (0.35 g, 2.0 mmol) in anhydrous THF (5 mL) at −5° C. The resulting suspension was stirred at −5° C. for 15 min and the solution of 3,4-dimethoxy-5-nitrobenzoyl chloride in THF was added over 10 min and stirred for an additional 1 hour at −5° C. The reaction mixture was warmed to 0° C., quenched by the addition of 1N.HCl solution (4 mL) and stirred for 10 min at room temperature, extracted by ethyl acetate (25 mL*2), the organic layers was dried with $Na_2SO_4$ and concentrated in vacuo to give the title compound 3 as an orange solid (169 mg, 22%). MS $[M+H]^+$ calcd for $C_{17}H_{16}N_5O_6$ 386.1, found 386.0.

Step2: Synthesis of (Z)-2-cyano-3-(3,4-dihydroxy-5-nitrophenyl)-3-hydroxy-N-(pyrimidin-4-ylmethyl) acrylamide (3)

A solution of (Z)-2-cyano-3-(3,4-dimethoxy-5-nitrophenyl)-3-hydroxy-N-(pyrimidin-4-ylmethyl)acrylamide (115 mg, 0.3 mmol) in DCM (5 mL) was added 1.0 M solution of $BBr_3$ in DCM (3 mL, 3 mmol) at −15° C. under nitrogen atmosphere. The resulting red suspension was stirred for 1 hour at −15° C. and allowed to warm to room temperature overnight. The reaction was quenched by the addition of $H_2O$ (2 mL) and stirred for 30 min. The aqueous phase was extracted with ethyl acetate (30 mL×3). The organic layers were combined, washed with brine and dried with $Na_2SO_4$. The solvent was eliminated under reduced pressure to give the crude product. Further purification by Prep-HPLC (0.5% TFA, MeOH/$H_2O$) gave the desired product as yellow solid (8 mg, 7%).1H NMR (400 MHz, DMSO) δ 14.18 (s, 1H), 10.74 (s, 2H), 9.12 (s, 1H), 8.75 (d, J=5.2 Hz, 1H), 7.88 (s, 1H), 7.55 (d, J=2.1 Hz, 1H), 7.45 (d, J=4.7 Hz, 1H), 4.52 (s, 2H). MS $[M+H]^+$ calcd for $C_{15}H_{12}N_5O_6$ 356.1, found 356.0

Compound 675:

675 was prepared by four synthetic steps from methyl 3-hydroxyisoxazole-5-carboxylate according to the following procedure:

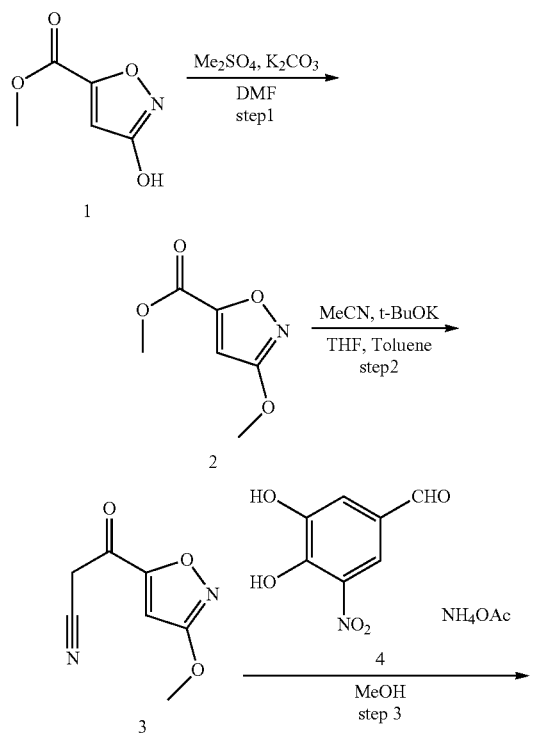

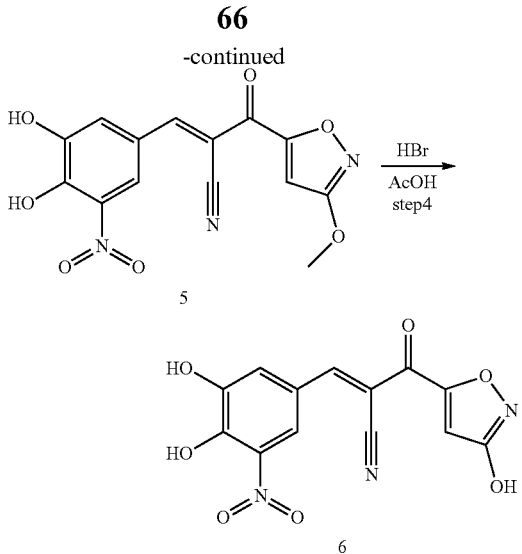

Step1: Synthesis of Methyl 3-methoxyisoxazole-5-carboxylate (2)

A mixture of methyl 3-hydroxyisoxazole-5-carboxylate (1.0 g, 7.0 mmol) and $K_2CO_3$ (1.9 g, 14 mmol) in dry DMF (15 mL) was added $Me_2SO_4$ (1.0 g, 8.4 mmol) at 0° C. The reaction solution was stirred at 0° C. continuously, and monitored by TLC until all the starting material was consumed completely; 50 mL of water was added. The residue was extracted by EA for two times (25 mL×2), and the organic layer was washed with brine (25 mL×3), and dried over anhydrous $Na_2SO_4$. The organic layer was concentrated in vacuo to afford the desired product (850 mg, 77%) without further purification. MS $[M+H]^+$ calcd for $C_6H_7NO_4$ 158.0, found 158.0.

Step2: Synthesis of 3-(3-methoxyisoxazol-5-yl)-3-oxopropanenitrile (3)

A mixture of MeCN (553 mg, 13.5 mmol) and t-BuOK (1.5 g, 13.5 mmol) in dry THF (25 mL) and toluene (15 mL) was added methyl 3-methoxyisoxazole-5-carboxylate (850 mg, 5.4 mmol) at rt. The reaction solution was stirred at 80° C. continuously for 24 h, and monitored by TLC until all the starting material was consumed completely. 50 mL of water was added. The aqueous phase was extracted by EA for two times (25 mL×2), and the organic layer was combined and washed with brine (25 mL×3), and dried over anhydrous $Na_2SO_4$. The organic layer was concentrated in vacuo to afford the crude product which was purified by silica chromatograph (100 g, 200-300 m, eluted by PE/EA=3/1) to afford the desired product as bright yellow solid (650 mg, 72%). MS $[M+H]^+$ calcd for $C_7H_6N_2O_3$ 167.0, found 167.0.

Step3: Synthesis of (E)-3-(3,4-dihydroxy-5-nitrophenyl)-2-(3-methoxyisoxazole-5-carbonyl)acrylonitrile (5)

A mixture of 3-(3-methoxyisoxazol-5-yl)-3-oxopropanenitrile (200 mg, 1.2 mmol), 3,4-dihydroxy-5-nitrobenzaldehyde (183 mg, 1.0 mmol) and $NH_4OAc$ (554 mg, 7.2 mmol) in MeOH (15 mL) was refluxed for 3 hours, then cooled to room temperature. The reaction mixture was filtered and the solid was collected and washed by $H_2O$ (15 mL). The solid was re-dissolved in MeOH (5 mL) and the PH was adjusted to 3-5 by adding 5 mL of 1N aqueous HCl. The desired product was obtained by filter and dried in vacuo as bright yellow solid (250 mg, 76%). MS [MH]+ calcd for $C_{14}H_9N_3O_7$ 332.0, found 332.0.

Step4: Synthesis of (E)-3-(3,4-dihydroxy-5-nitrophenyl)-2-(3-hydroxyisoxazole-5-carbonyl)acrylonitrile (6)

A solution of (E)-3-(3,4-dihydroxy-5-nitrophenyl)-2-(3-methoxyisoxazole-5-carbonyl) acrylonitrile (150 mg, 0.45 mmol) in AcOH (5 mL) was added 0.5 mL 33% HBr (in AcOH) at rt. The reaction solution was stirred at 80° C. continuously for 3 h and monitored by LC-MS until all the starting material was consumed completely. The reaction mixture was concentrated in vacuo to afford the crude product which was purified by by Prep-HPLC (0.5% TFA, MeCN/H$_2$O) to afford the desired product as yellow solid (22 mg, 15%). MS [MH]+ calcd for $C_{13}H_7N_3O_7$ 318.0, found 318.0. $^1$H NMR (400 MHz, DMSO) δ 11.96 (s, 2H), 8.32 (s, 1H), 8.18 (d, J=2.1 Hz, 1H), 7.88 (d, J=2.2 Hz, 1H), 6.93 (s, 1H)

Compound 687:

687 was prepared in two synthetic steps from 2-cyano-acetate according, according to the following procedure:

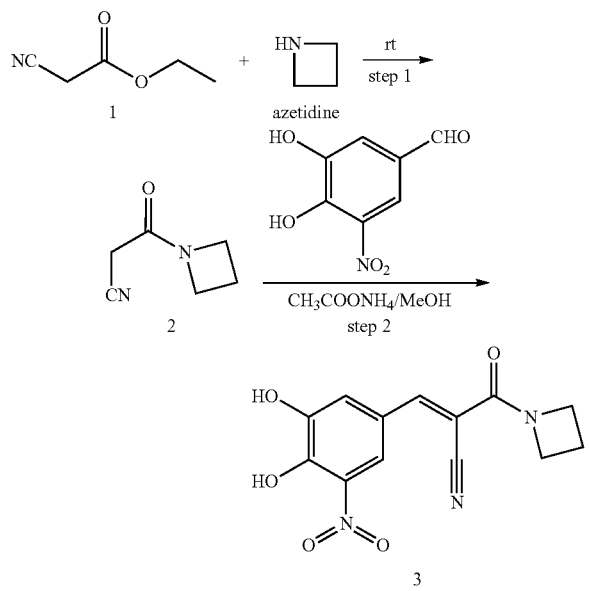

Step1: Synthesis of 3-(azetidin-1-yl)-3-oxopropanenitrile (2)

A mixture of ethyl 2-cyanoacetate (565 mg, 5.0 mmol) and azetidine (285 mg, 5.0 mmol) was stirred at rt overnight. The reaction solution was purified by HPLC to afford the desire product. MS [M+H]+ calcd for $C_6H_9N_2O_1$ 125.1, found 125.1

Step2: Synthesis of 3-(azetidin-1-yl)-3-oxopropanenitrile (3)

A mixture of 3-(azetidin-1-yl)-3-oxopropanenitrile (124 mg, 1.0 mmol), 3,4-dihydroxy-5-nitrobenzaldehyde (183 mg, 1.0 mmol) and CH$_3$COONH$_4$ (770 mg, 10.0 mmol) in MeOH (15 mL) was stirred at 80° C. overnight and then cooled to rt. The reaction mixture was filtered to collect the solid. The solid was re-dissolved in MeOH and the PH was adjusted to 3-5 by adding 1N HCl. The desire product was collected by filtered and dried in vavuo. (116 mg, 40%). MS [M+H]+ calcd for $C_{13}H_{12}N_3O_5$ 290.2, found 289.9. $^1$H NMR (400 MHz, DMSO) δ 10.93 (s, 2H), 8.01 (d, J=2.1 Hz, 1H), 7.97 (s, 1H), 7.81 (d, J=2.1 Hz, 1H), 4.48 (t, J=7.2 Hz, 2H), 4.03 (t, J=7.3 Hz, 2H), 2.32-2.22 (m, 2H).

Compound 688:

688 was prepared in two synthetic steps from 2-cyano-acetate according to the following procedure:

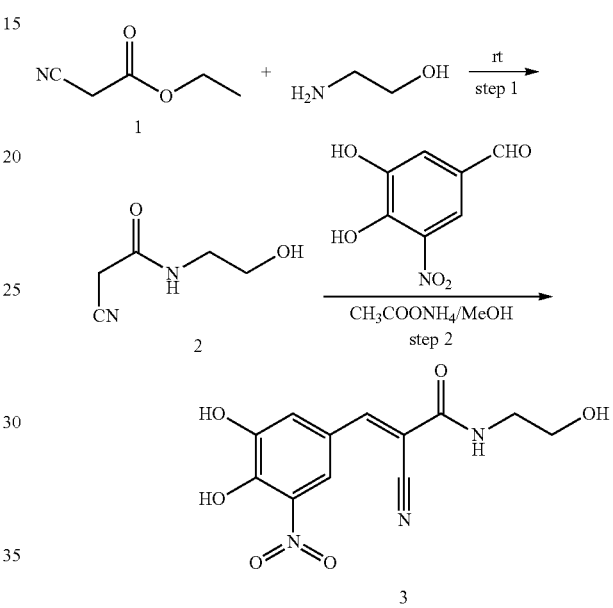

Step1: Synthesis of 2-cyano-N-(2-hydroxyethyl)acetamide (2)

A mixture of ethyl 2-cyanoacetate (113 mg, 1.0 mmol) and 2-aminoethanol (305 mg, 5.0 mmol) was stirred at rt overnight. The reaction solution was purified by HPLC to afford the desire product. MS [M+H]+ calcd for $C_5H_9N_2O_2$ 129.1, found 129.1

Step2: Synthesis of (E)-2-cyano-3-(3,4-dihydroxy-5-nitrophenyl)-N-(2-hydroxyethyl)acrylamide (3)

A mixture of 2-cyano-N-(2-hydroxyethyl)acetamide (65 mg, 0.5 mmol), 3,4-dihydroxy-5-nitrobenzaldehyde (92 mg, 0.5 mmol) in MeOH (15 mL) and CH$_3$COONH$_4$ (385 mg, 5.0 mmol) was stirred at 80° C. overnight and then cooled to rt. The reaction mixture was filtered to collect the solid. The solid was re-dissolved in MeOH and the PH was adjusted to 3~5 by adding 1N HCl. The desire product was collected by filtered and dried in vavuo. (80 mg, 54%). MS [M+H]+ calcd for $C_{13}H_{12}N_3O_6$ 294.2, found 293.8. $^1$H NMR (400 MHz, DMSO) δ 10.92 (s, 2H), 8.30 (t, J=5.5 Hz, 1H), 8.06 (s, 1H), 7.95 (d, J=2.1 Hz, 1H), 7.78 (d, J=2.2 Hz, 1H), 3.49 (t, J=6.1 Hz, 2H), 3.28 (q, J=5.9 Hz, 2H), 3.17 (s, 1H).

Compound 691:

691 was prepared in two synthetic steps from 3,4-dimethoxy-5-nitrobenzoic acid, according to the following procedure:

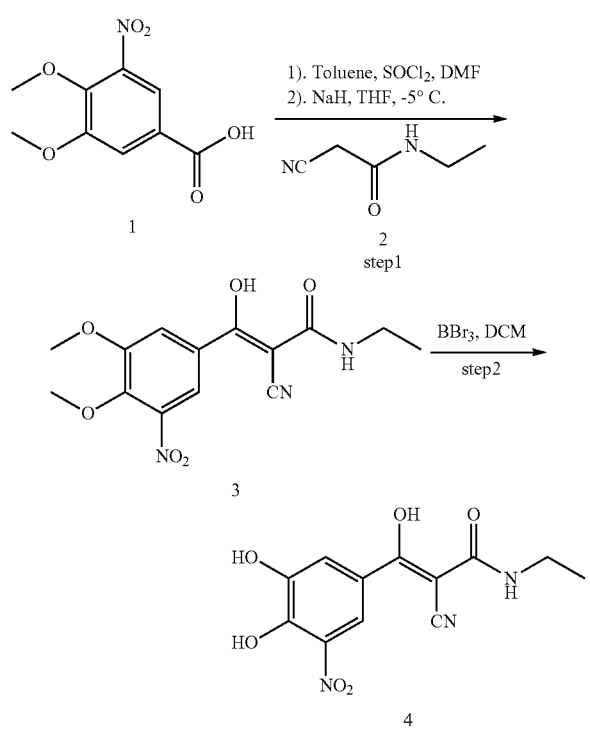

Step1: Synthesis of (Z)-2-cyano-3-(3,4-dimethoxy-5-nitrophenyl)-3-hydroxy-N-ethylacrylamide (3)

Under a nitrogen atmosphere, SOCl₂ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. and stirred for 15 hours. The organic solvent was eliminated by distillation under reduced pressure. More toluene was added and eliminated again. The resulting yellowish solid 3,4-dimethoxy-5-nitrobenzoyl chloride was dissolved in anhydrous THF (5 mL).

Under a nitrogen atmosphere, 60% NaH (0.18 g, 4.4 mmol) was added to the solution of 2-cyano-N-ethylacetamide (0.23 g, 2.0 mmol) in anhydrous THF (5 mL) at −5 OC. The resulting suspension was stirred at −5° C. for 15 min and the solution of 3,4-dimethoxy-5-nitrobenzoyl chloride in THF was added over 10 min and stirred for an additional 1 h at −5° C. The reaction mixture was warmed to 0° C., quenched by the addition of 1N.HCl solution (4 mL) and stirred for 10 min at room temperature, extracted by ethyl acetate (25 mL*2), the organic layers was dried with Na₂SO₄ and concentrated in vacuo to give the title compound 3 as an yellow solid (288 mg, 39%).

Step2: Synthesis of (Z)-2-cyano-3-(3,4-dihydroxy-5-nitrophenyl)-N-ethyl-3-hydroxyacrylamide (4)

A solution of (Z)-2-cyano-3-(3,4-dimethoxy-5-nitrophenyl)-3-hydroxy-N-ethylacrylamide (167 mg, 0.5 mmol) in DCM (5 mL) was added 1.0 M solution of BBr₃ in DCM (3 mL, 3 mmol) at −15° C. under nitrogen atmosphere. The resulting red suspension was stirred for 1 hour at −15° C. and allowed to warm to room temperature overnight. The reaction was quenched by the addition of H₂O (2 mL) and stirred for 30 min. The aqueous phase was extracted with ethyl acetate (30 mL*3). The organic layers were combined, washed with brine and dried with Na₂SO₄. The solvent was eliminated under reduced pressure to give the crude product. Further purification by Prep-HPLC gave the desired product as yellow solid (48 mg, 33%).1H NMR (400 MHz, DMSO) δ 14.18 (s, 1H), 10.74 (s, 2H), 9.12 (s, 1H), 8.75 (d, J=5.2 Hz, 1H), 7.88 (s, 1H), 7.55 (d, J=2.1 Hz, 1H), 7.45 (d, J=4.7 Hz, 1H), 4.52 (s, 2H). MS [M+H]⁺ calcd for C₁₂H₁₂N₃O₆ 294.2, found 293.8

Compound 692:

692 was prepared in two synthetic steps from 3,4-dimethoxy-5-nitrobenzoic acid, according to the following procedure:

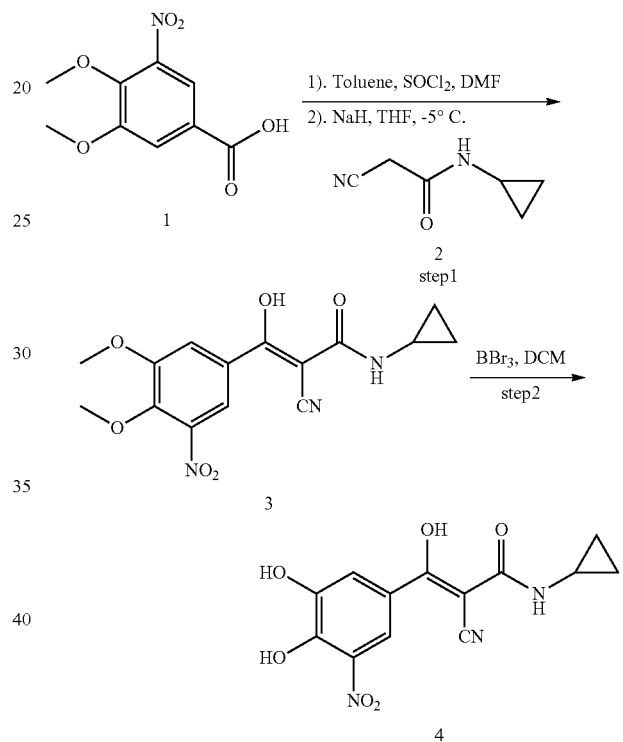

Step1: Synthesis of (Z)-2-cyano-N-cyclopropyl-3-(3,4-dimethoxy-5-nitrophenyl)-3-hydroxyacrylamide (3)

Under a nitrogen atmosphere, SOCl₂ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. and stirred for 15 hours. The organic solvent was eliminated by distillation under reduced pressure. More toluene was added and eliminated again. The resulting yellowish solid 3,4-dimethoxy-5-nitrobenzoyl chloride was dissolved in anhydrous THF (5 mL).

Under a nitrogen atmosphere, 60% NaH (0.18 g, 4.4 mmol) was added to the solution of 2-cyano-N-cyclopropylacetamide (250 mg, 2.0 mmol) in anhydrous THF (5 mL) at −5 OC. The resulting suspension was stirred at −5 OC for 15 min and the solution of 3,4-dimethoxy-5-nitrobenzoyl chloride in THF was added over 10 min and stirred for an additional 1 h at −5° C. The reaction mixture was warmed to 0° C., quenched by the addition of 1N.HCl solution (4 mL) and stirred for 10 min at room temperature, extracted by ethyl acetate (25 mL*2), the organic layers was dried with Na$_2$SO$_4$ and concentrated in vacuo to give the compound 3 as an yellow solid (242 mg, 36%).

Step2: Synthesis of (Z)-2-cyano-N-cyclopropyl-3-(3,4-dihydroxy-5-nitrophenyl)-3-hydroxyacrylamide (4)

A solution of (Z)-2-cyano-N-cyclopropyl-3-(3,4-dimethoxy-5-nitrophenyl)-3-hydroxyacrylamide (166 mg, 0.5 mmol) in DCM (5 mL) was added 1.0 M solution of BBr$_3$ in DCM (3 mL, 3 mmol) at −15 OC under nitrogen atmosphere. The resulting red suspension was stirred for 1 hour at −15° C. and allowed to warm to room temperature overnight. The reaction was quenched by the addition of H$_2$O (2 mL) and stirred for 30 min. The aqueous phase was extracted with ethyl acetate (30 mL*3). The organic layers were combined, washed with brine and dried with Na$_2$SO$_4$. The solvent was eliminated under reduced pressure to give the crude product. Further purification by Prep-HPLC gave the desired product as yellow solid (25 mg, 26%). 1H NMR (400 MHz, DMSO) δ 10.81 (s, 1H), 8.82 (s, 1H), 7.88 (d, J=1.9 Hz, 1H), 7.54 (d, J=2.1 Hz, 1H), 2.83-2.77 (m, 1H), 0.74-0.64 (m, 4H). MS [M−H]$^-$ calcd for C$_{13}$H$_{10}$N$_3$O$_6$ 304.2, found 303.9.

Compound 697:

697 was prepared in two synthetic steps from methyl 5-(cyanomethyl)pyrazine-2-carboxylate, according to the following procedure:

Step1: Synthesis of (E)-methyl 5-(1-cyano-2-(3,4-dimethoxy-5-nitrophenyl)-2-hydroxyvinyl)pyrazine-2-carboxylate (3)

Under a nitrogen atmosphere, 60% NaH (0.072 g, 1.8 mmol) was added to the solution of methyl 5-(cyanomethyl)pyrazine-2-carboxylate (0.15 g, 0.9 mmol) in anhydrous THF (5 mL) at −5° C. The resulting suspension was stirred at −5 OC for 15 min and the solution of 3,4-dimethoxy-5-nitrobenzoyl chloride in THF was added over 10 min and stirred for an additional 1 hour at −5 OC. The reaction mixture was warmed to 0° C., quenched by the addition of 1N.HCl solution (4 mL) and stirred for 10 min at room temperature, extracted by ethyl acetate (25 mL*2), the organic layers was dried with Na$_2$SO$_4$ and concentrated in vacuo to give the title compound (E)-methyl 5-(1-cyano-2-(3,4-dimethoxy-5-nitrophenyl)-2-hydroxyvinyl)pyrazine-2-carboxylate as an orange solid (125 mg, 30%). MS [M+H]$^+$ calcd for C$_{17}$H$_{14}$N$_4$O$_7$ 387.0, found 387.0.

Step2: Synthesis of (E)-5-(1-cyano-2-(3,4-dihydroxy-5-nitrophenyl)-2-hydroxyvinyl) pyrazine-2-carboxylic Acid (4)

A solution of (E)-methyl 5-(1-cyano-2-(3,4-dimethoxy-5-nitrophenyl)-2-hydroxyvinyl) pyrazine-2-carboxylate (125 mg, 0.3 mmol) in DCM (5 mL) was added 1.0 M solution of BBr$_3$ in DCM (3 mL, 3 mmol) at −15 OC under nitrogen atmosphere. The resulting red suspension was stirred for 1 hour at −15° C. and allowed to warm to room temperature overnight. The reaction was quenched by the addition of H$_2$O (2 mL) and stirred for 30 min. The aqueous phase was extracted with ethyl acetate (30 mL*3). The organic layers were combined, washed with brine and dried with Na$_2$SO$_4$. The solvent was eliminated under reduced pressure to give the crude product. Further purification by Prep-HPLC (0.5% TFA, MeOH/H$_2$O) gave the desired product as yellow solid (15 mg, 15%).1H NMR (400 MHz, DMSO) δ 10.57 (s, 1H), 9.17 (s, 1H), 8.68 (s, 1H), 7.81 (s, 1H), 7.51 (s, 1H). MS [M+H]$^+$ calcd for C$_{14}$H$_8$N$_4$O$_7$ 345.0, found 345.0

Compound 701:

701 was prepared in two synthetic steps from 3,4-dimethoxy-5-nitrobenzoic acid, according to the following procedure:

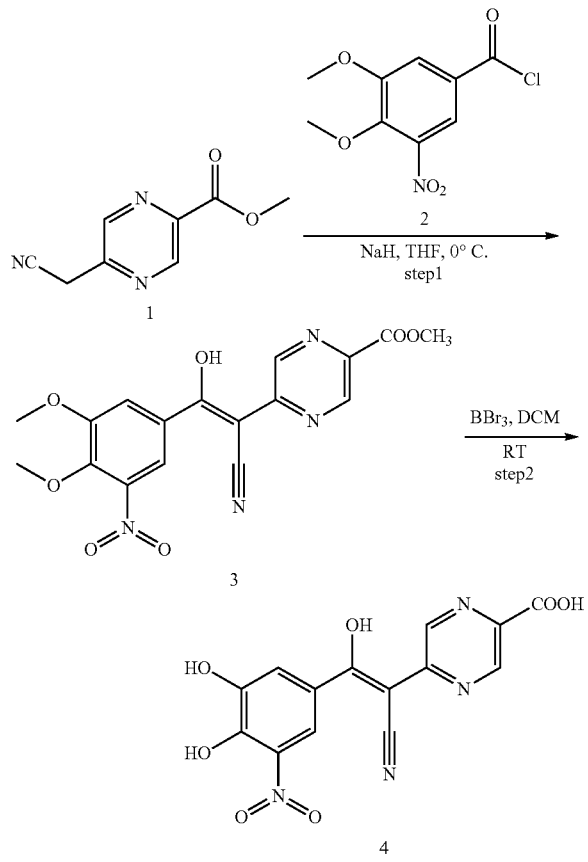

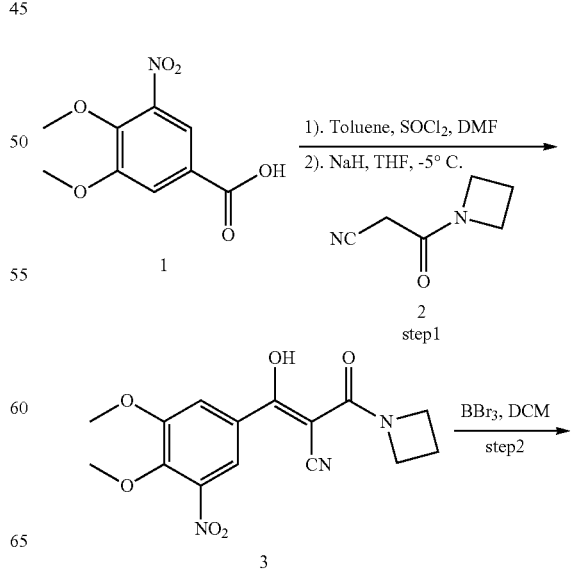

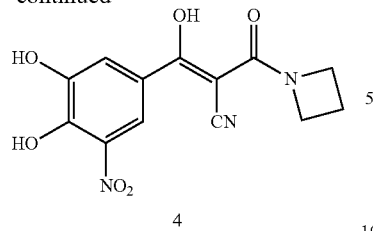

Step1: Synthesis of (Z)-2-(azetidine-1-carbonyl)-3-(3,4-dimethoxy-5-nitrophenyl)-3-hydroxyacrylonitrile (3)

Under a nitrogen atmosphere, $SOCl_2$ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. and stirred for 15 hours. The organic solvent was eliminated by distillation under reduced pressure. More toluene was added and eliminated again. The resulting yellowish solid 3,4-dimethoxy-5-nitrobenzoyl chloride was dissolved in anhydrous THF (5 mL).

Under a nitrogen atmosphere, 60% NaH (0.18 g, 4.4 mmol) was added to the solution of 2-cyano-N-cyclopropy-lacetamide (250 mg, 2.0 mmol) in anhydrous THF (5 mL) at −5 OC. The resulting suspension was stirred at −5° C. for 15 min and the solution of 3,4-dimethoxy-5-nitrobenzoyl chloride in THF was added over 10 min and stirred for an additional 1 h at −5° C. The reaction mixture was warmed to 0° C., quenched by the addition of 1N.HCl solution (4 mL) and stirred for 10 min at room temperature, extracted by ethyl acetate (25 mL*2), the organic layers was dried with $Na_2SO_4$ and concentrated in vacuo to give the compound 3 (146 mg, 22%).

Step2: Synthesis of (Z)-2-(azetidine-1-carbonyl)-3-(3,4-dihydroxy-5-nitrophenyl)-3-hydroxyacrylonitrile (4)

A solution of (Z)-2-(azetidine-1-carbonyl)-3-(3,4-dimethoxy-5-nitrophenyl)-3-hydroxyacrylonitrile (146 mg, 0.4 mmol) in DCM (5 mL) was added 1.0 M solution of $BBr_3$ in DCM (2 mL, 2 mmol) at −15 OC under nitrogen atmosphere. The resulting red suspension was stirred for 1 hour at −15° C. and allowed to warm to room temperature overnight. The reaction was quenched by the addition of $H_2O$ (2 mL) and stirred for 30 min. The aqueous phase was extracted with ethyl acetate (30 mL*3). The organic layers were combined, washed with brine and dried with Na2SO4. The solvent was eliminated under reduced pressure to give the crude product. Further purification by Prep-HPLC gave the desired product (18 mg, 15%). 11H NMR (400 MHz, DMSO) δ 10.93 (s, 2H), 7.93 (d, J=2.1 Hz, 1H), 7.55 (d, J=2.1 Hz, 1H), 4.36 (s, 4H), 2.35-2.27 (m, 2H). MS [M+H]+ calcd for $C_{13}H_{12}N_3O_6$ 306.2, found 305.9

Compound 711:

711 was prepared in two synthetic steps from 3-oxo-3-(thiazol-4-yl)propanenitrile, according to the following procedure:

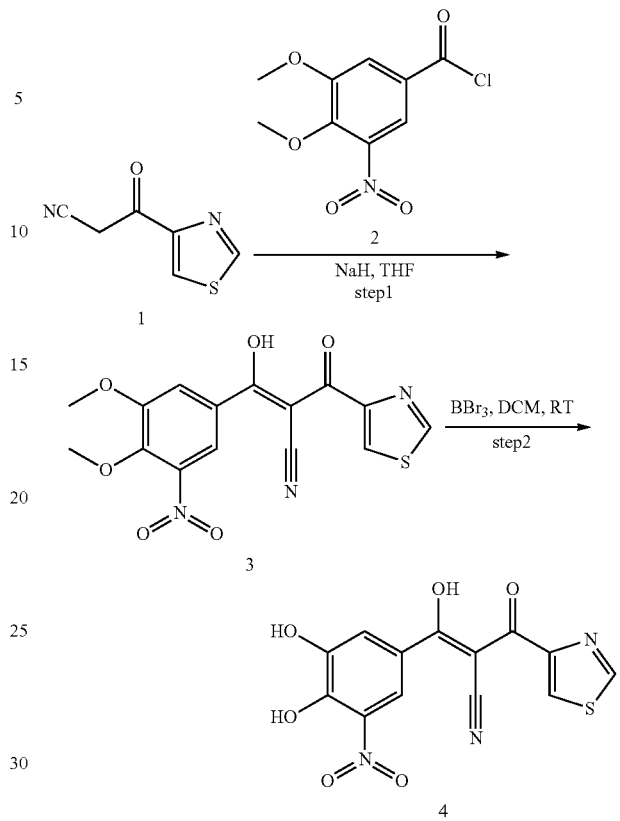

Step1: Synthesis of (Z)-3-(3,4-dimethoxy-5-nitrophenyl)-3-hydroxy-2-(thiazole-4-carbonyl)acrylonitrile (2)

Under a nitrogen atmosphere, 60% NaH (0.072 g, 1.8 mmol) was added to the solution of 3-oxo-3-(thiazol-4-yl)propanenitrile (0.41 g, 2.7 mmol) in anhydrous THF (15 mL) at −5 OC. The resulting suspension was stirred at −5° C. for 15 min and the solution of 3,4-dimethoxy-5-nitrobenzoyl chloride (661 mg, 2.7 mmol) in THF was added over 5 min and stirred for an additional 1 hour at −5 OC. The reaction mixture was warmed to 0° C., quenched by the addition of 1N.HCl solution (4 mL) and stirred for 10 min at room temperature, extracted by ethyl acetate (25 mL*2), the organic layers was dried with $Na_2SO_4$ and concentrated in vacuo to give the title compound (E)-methyl 5-(1-cyano-2-(3,4-dimethoxy-5-nitrophenyl)-2-hydroxyvinyl)pyrazine-2-carboxylate as an orange solid (600 mg, 62%). MS [M+H]+ calcd for $C_{15}H_{11}N_3O_6S$ 362.0, found 362.0.

Step2: Synthesis of (Z)-3-(3,4-dihydroxy-5-nitrophenyl)-3-hydroxy-2-(thiazole-4-carbonyl)acrylonitrile (4)

A solution of (Z)-3-(3,4-dimethoxy-5-nitrophenyl)-3-hydroxy-2-(thiazole-4-carbonyl)acrylonitrile (70 mg, 0.2 mmol) in DCM (5 mL) was added 1.0 M solution of $BBr_3$ in DCM (1 mL, 1 mmol) at −15 OC under nitrogen atmosphere. The resulting red suspension was stirred for 1 hour at −15° C. and allowed to warm to room temperature overnight. The reaction was quenched by the addition of 0.5 $N.NH_4OH$ (2 mL) and stirred for 30 min. The aqueous phase was extracted with ethyl acetate (30 mL*3). The organic layers were combined, washed with brine and dried with Na$_2$SO$_4$. The solvent was eliminated under reduced pressure to give the crude product. Further purification by Prep-HPLC (0.5% TFA, MeOH/H$_2$O) gave the desired product as yellow solid (11 mg, 17%). 1H NMR (400 MHz, DMSO) δ 10.66 (s, 1H), 8.61 (s, 1H), 7.97 (s, 1H), 7.65 (s, 1H). MS [M+H]$^+$ calcd for C$_{13}$H$_7$N$_3$O$_6$S 334.0, found 334.0.

Compound 709:

709 was prepared in two synthetic steps from (E)-2-cyano-3-(3,4-dihydroxy-5-nitrophenyl)acrylic acid, according to the following procedure:

aqueous phase was extracted with ethyl acetate (30 mL*3). The organic layers were combined, washed with brine and dried with Na$_2$SO$_4$. The solvent was eliminated under reduced pressure to give the crude product. Further purification by Prep-HPLC gave the desired product (7 mg, 6.2%). 1H NMR (400 MHz, DMSO) δ 8.65 (t, J=5.8 Hz, 1H), 8.10 (s, 1H), 7.98 (d, J=2.1 Hz, 1H), 7.79 (d, J=2.1 Hz, 1H), 3.88 (d, J=5.8 Hz, 2H). MS [M+H]$^+$ calcd for C$_{12}$H$_{10}$N$_3$O$_7$ 308.2, found 308.0.

Compound 693:

693 was prepared in three synthetic steps from ethyl 2-cyanoacetate, according to the following procedure:

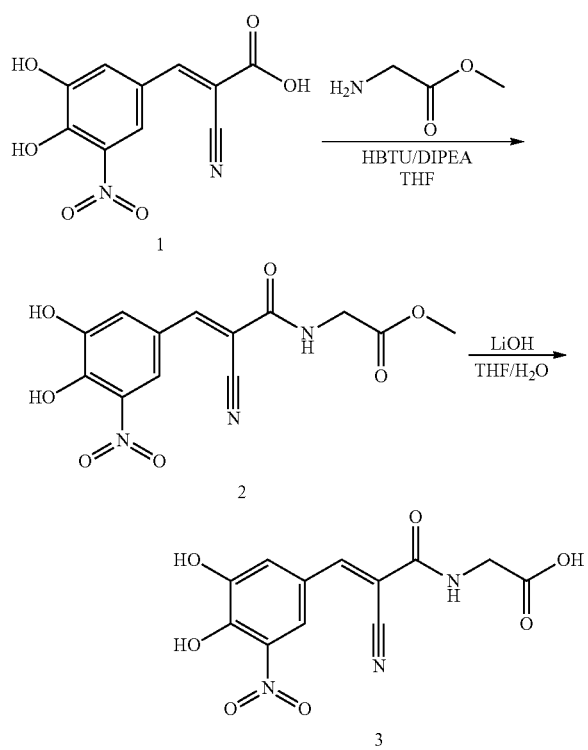

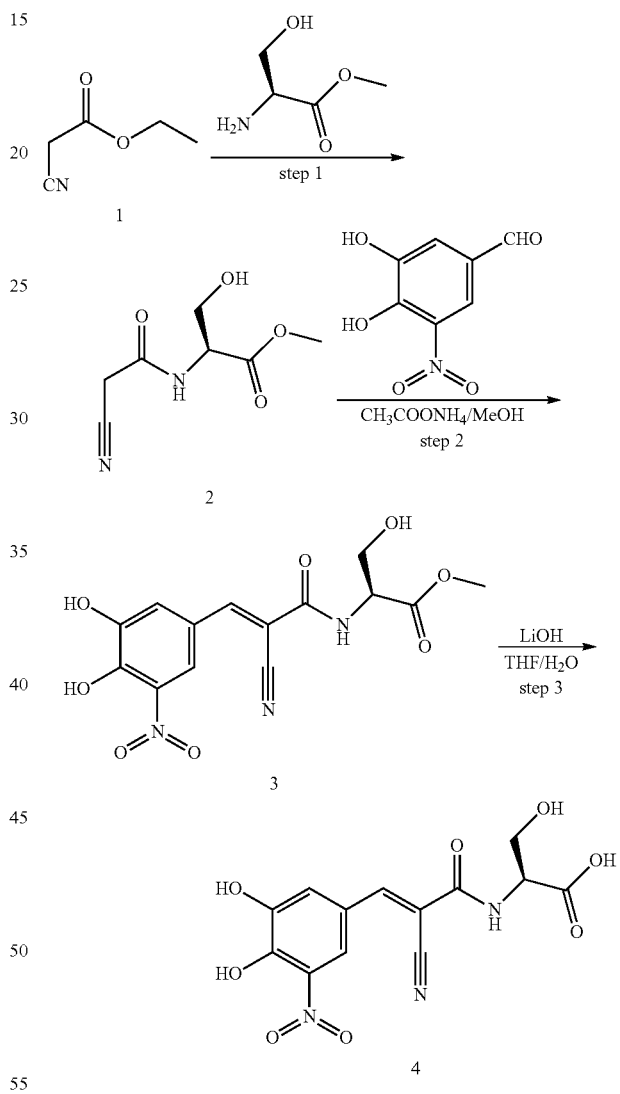

Step1: Synthesis of (E)-methyl 2-(2-cyano-3-(3,4-dihydroxy-5-nitrophenyl)acrylamido)acetate (2)

A solution of (E)-2-cyano-3-(3,4-dihydroxy-5-nitrophenyl)acrylic acid (1) (250 mg, 1 mmol) and methyl 2-aminoacetate (89 mg, 1 mmol) in THF (15 mL) was added HBTU (600 mg, 1.5 mmol) and DIPEA (388 mg, 3 mmol) at rt. The resulting suspension was stirred for 5 hours at 60° C. and allowed to cool to room temperature overnight. The reaction was added H$_2$O and extracted with ethyl acetate (30 mL*3). The organic layers were combined to afford the crude product which was used in the next step without further purification (120 mg, 37.4%).

Step2: Synthesis of (E)-2-(2-cyano-3-(3,4-dihydroxy-5-nitrophenyl)acrylamido)acetic Acid (3)

A solution of (E)-methyl 2-(2-cyano-3-(3,4-dihydroxy-5-nitrophenyl)acrylamido)acetate (2) (120 mg, 0.37 mmol) in THF/H$_2$O (5 mL/5 mL) was added LiOH (24 mg, 0.55 mmol) at 0° C. The resulting suspension was stirred for 1 hour at 0° C. and was quenched by adding aqueous HCl. The Step1: Synthesis of (S)-methyl 2-(2-cyanoacetamido)-3-hydroxypropanoate (2)

A mixture of ethyl 2-cyanoacetate (1130 mg, 10.0 mmol) and (S)-methyl 2-amino-3-hydroxypropanoate (1190 mg, 10.0 mmol) was stirred at r.t. overnight. The reaction solution was added 10 mL MeOH and filtered to collect the solid as crude product, which was used in next step without further purification. MS [M+H]$^+$ calcd for C$_7$H$_{11}$N$_2$O$_4$ 187.2, found 187.2.

Step2: Synthesis of (S,E)-methyl 2-(2-cyano-3-(3,4-dihydroxy-5-nitrophenyl)acrylamido)-3-hydroxypropanoate (3)

A solution of (S)-methyl 2-(2-cyanoacetamido)-3-hydroxypropanoate (930 mg, 5 mmol) (2) and 3,4-dihydroxy-5-nitrobenzaldehyde (915 mg, 5 mmol) in MeOH (25 mL) was added $CH_3COONH_4$ (3850 mg, 50 mmol) at rt. The reaction solution was stirred at 60° C. continuously for 5 h and monitored by TLC until all the starting material was consumed completely. Then the reaction mixture was cooled to rt and the solvent was eliminated under reduced pressure, then the Sat. aq. NaCl (100 mL) was added. The aqueous solution was extracted by EA for three times (50 mL*3). The organic layer was concentrated in vacuo to afford crude product which was purified by silica chromatograph chromatography to afford the desired product (705 mg, 40%). MS $[M+H]^+$ calcd for $C_{14}H_{14}N_3O_8$ 352.3, found 352.3.

Step3: Synthesis of (S,E)-2-(2-cyano-3-(3,4-dihydroxy-5-nitrophenyl)acrylamido)-3-hydroxypropanoic Acid (4)

A solution of (S,E)-methyl 2-(2-cyano-3-(3,4-dihydroxy-5-nitrophenyl)acrylamido)-3-hydroxypropanoate (3) (705 mg, 2 mmol) in $THF/H_2O$ (10 mL/10 mL) was added LiOH (126 mg, 3 mmol) at 0° C. The resulting suspension was stirred for 1 hour at 0° C. and was quenched by adding aqueous HCl. The aqueous phase was extracted with ethyl acetate (30 mL*3). The organic layers were combined, washed with brine and dried with $Na_2SO_4$. The solvent was eliminated under reduced pressure to give the crude product. Further purification by Prep-HPLC gave the desired product (220 mg, 32.6%). 1H NMR (400 MHz, DMSO) δ 12.89 (s, 1H), 10.94 (s, 2H), 8.22 (d, J=7.6 Hz, 1H), 8.15 (s, 1H), 7.97 (d, J=2.1 Hz, 1H), 7.82 (d, J=2.1 Hz, 1H), 5.05 (s, 1H), 4.41 (m, 1H), 3.79 (m, 2H). MS $[M+H]^+$ calcd for $C_{13}H_{12}N_3O_8$ 338.2, found 337.8

Compound 702:

702 was prepared in three synthetic steps from ethyl 2-cyanoacetate, according to the following procedure:

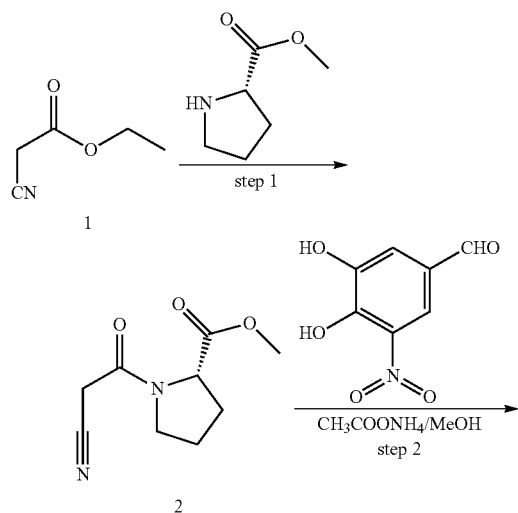

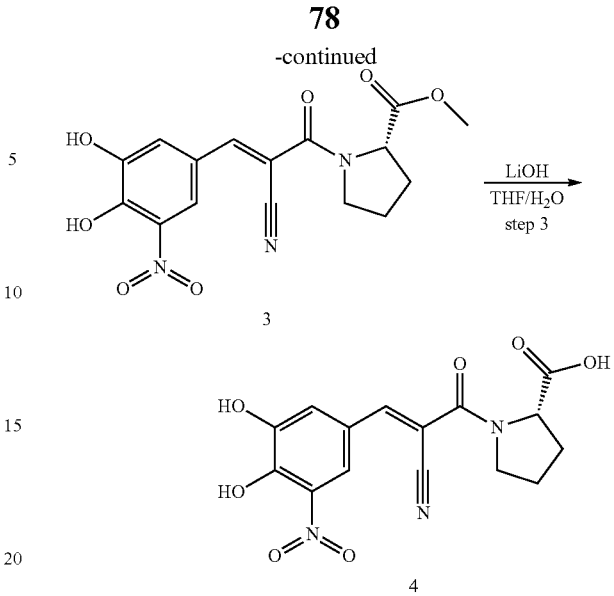

Step1: Synthesis of (S)-methyl 1-(2-cyanoacetyl)pyrrolidine-2-carboxylate (2)

A mixture of ethyl 2-cyanoacetate (113 mg, 1.0 mmol) and (S)-methyl pyrrolidine-2-carboxylate (129 mg, 1.0 mmol) was stirred at r.t. overnight. The reaction solution was added 10 mL MeOH and filtered to collect the solid as crude product, which was used in next step without further purification. MS $[M+H]^+$ calcd for $C_9H_{13}N_2O_3$ 197.2, found 197.2.

Step2: Synthesis of (S,E)-methyl 2-(2-cyano-3-(3,4-dihydroxy-5-nitrophenyl)acrylamido)-3-hydroxypropanoate (3)

A solution of (S)-methyl 1-(2-cyanoacetyl)pyrrolidine-2-carboxylate (2) (196 mg, 1 mg) and 3,4-dihydroxy-5-nitrobenzaldehyde (183 mg, 1 mmol) in MeOH (5 mL) was added $CH_3COONH_4$ (770 mg, 10 mmol) at rt. The reaction solution was stirred at 60° C. overnight and monitored by TLC until all the starting material was consumed completely. Then the reaction mixture was cooled to r.t. and the solvent was eliminated under reduced pressure, then the Sat. aq. NaCl (100 mL) was added. The aqueous solution was extracted by EA for three times (50 mL*3). The organic layer was concentrated in vacuo to afford crude product which was purified by silica chromatograph chromatography to afford the desired product (43 mg, 12%). MS $[M+H]^+$ calcd for $C_{16}H_{16}N_3O_7$ 362.3, found 362.3.

Step3: Synthesis of (S,E)-1-(2-cyano-3-(3,4-dihydroxy-5-nitrophenyl)acryloyl)pyrrolidine-2-carboxylic Acid (4)

A solution of (S,E)-methyl 2-(2-cyano-3-(3,4-dihydroxy-5-nitrophenyl)acrylamido)-3-hydroxypropanoate (3) (43 mg, 0.12 mmol) in $THF/H_2O$ (2 mL/1 mL) was added LiOH (8 mg, 0.18 mmol) at 0° C. The resulting suspension was stirred for 1 hour at 0° C. and was quenched by adding aqueous HCl. The aqueous phase was extracted with ethyl acetate (30 mL*3). The organic layers were combined, washed with brine and dried with $Na_2SO_4$. The solvent was eliminated under reduced pressure to give the crude product.

Further purification by Prep-HPLC gave the desired product (6 mg, 15%). 1H NMR (400 MHz, DMSO) δ 7.25 (t, J=7.4 Hz, 1H), 7.21-7.09 (m, 2H), 2.30 (s, 2H), 2.07 (s, 4H). MS [M+H]+ calcd for $C_{15}H_{14}N_3O_7$ 348.3, found 347.8

Compound 347N:

347N was prepared in single synthetic step from 2-cyano-3-(3,4-dihydroxy-5-nitrophenyl)-N,N-diethyl-3-oxopropanamide (1, compound 347), according to the following procedure:

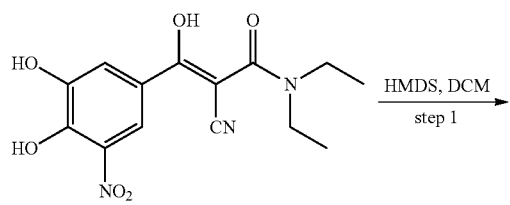

Step1: Synthesis of 2-cyano-3-(3,4-dihydroxy-5-nitrophenyl)-N,N-diethyl-3-hydroxyacrylamide (2)

A solution of 2-cyano-3-(3,4-dihydroxy-5-nitrophenyl)-N,N-diethyl-3-oxopropanamide (350 mg, 1 mmol) in DCM (5 mL) was added HMDS (0.5 mL) at rt, then stirred for 48 h. After the reaction was completed, the reaction mixture was concentrated in vacuo to afford the crude product, further purification by Prep-HPLC afforded the desired product as yellow solid (60 mg, 19%). MS [M+H]+ calcd for $C_{14}H_{16}N_4O_5$ 321.1, found 321.1.

Compound 661N:

661N was prepared in one synthetic step from (Z)-3-(3,4-dihydroxy-5-nitrophenyl)-3-hydroxy-2-(piperidine-1-carbonyl)acrylonitrile, according to the following procedure:

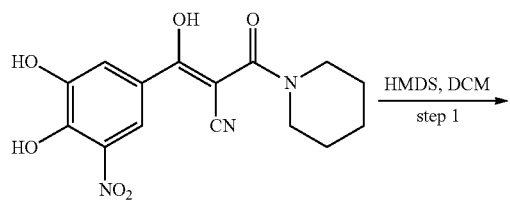

Step1: Synthesis of 3-amino-3-(3,4-dihydroxy-5-nitrophenyl)-2-(piperidine-1-carbonyl)acrylonitrile (2)

A solution of 3-(3,4-dihydroxy-5-nitrophenyl)-3-hydroxy-2-(piperidine-1-carbonyl)acrylonitrile (20 mg, 0.06 mmol) in DCM (5 mL) was added HMDS (1 mL) and stirred at rt for 72 h. And then the reaction mixture was concentrated in vacuo to afford the crude product, which was further purified by HPLC to afford the desired product as a yellow solid (1 mg, 5%). MS [MH]+ calcd for $C_{15}H_{16}N_4O_5$ 333.3, found 333.1. 1H NMR (400 MHz, DMSO) δ 8.21 (s, 1H), 7.66 (s, 1H), 6.74 (s, 1H), 1.25-1.65 (m, 6H), 1.23 (s, 1H).

Compound 691N:

691N was prepared in four synthetic steps from 3,4-dimethoxy-5-nitrobenzoic acid, according to the following procedure:

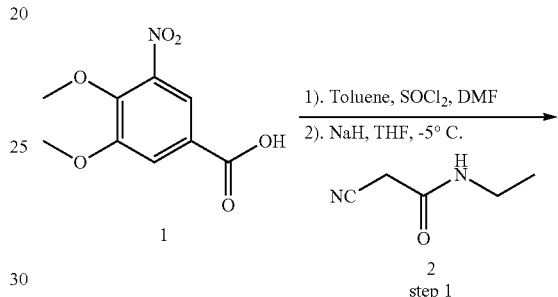

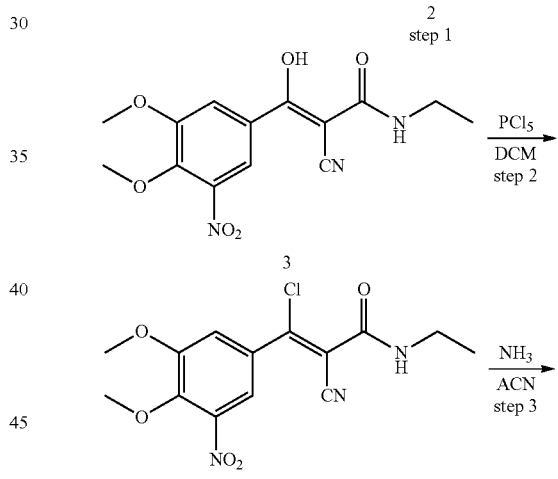

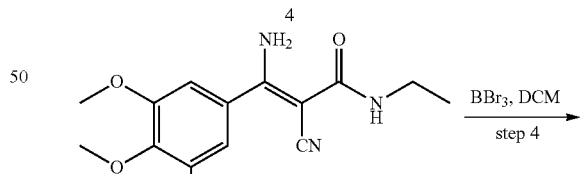

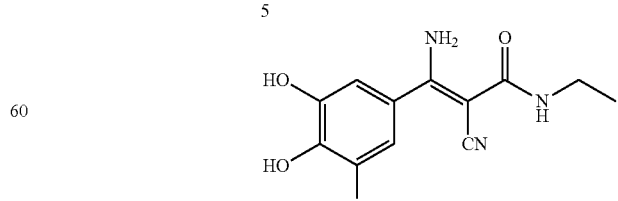

Step 1: Synthesis of (Z)-2-cyano-3-(3,4-dimethoxy-5-nitrophenyl)-3-hydroxy-N-ethylacrylamide (3)

Under a nitrogen atmosphere, SOCl₂ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. and stirred for 15 hours. The organic solvent was eliminated by distillation under reduced pressure. More toluene was added and eliminated again. The resulting yellowish solid 3,4-dimethoxy-5-nitrobenzoyl chloride was dissolved in anhydrous THF (5 mL).

Under a nitrogen atmosphere, 60% NaH (0.18 g, 4.4 mmol) was added to the solution of 2-cyano-N-ethylacetamide (0.23 g, 2.0 mmol) in anhydrous THF (5 mL) at −5° C. The resulting suspension was stirred at −5° C. for 15 min and the solution of 3,4-dimethoxy-5-nitrobenzoyl chloride in THF was added over 10 min and stirred for an additional 1 hour at −5° C. The reaction mixture was warmed to 0° C., quenched by the addition of 1N.HCl solution (4 mL) and stirred for 10 min at room temperature, extracted by ethyl acetate (25 mL*2), the organic layers was dried with Na₂SO₄ and concentrated in vacuo to give the title compound 3 as an yellow solid (265 mg, 36%).

Step 2: Synthesis of (Z)-3-chloro-2-cyano-3-(3,4-dimethoxy-5-nitrophenyl)-N-ethylacrylamide (4)

A solution of (Z)-2-cyano-3-(3,4-dimethoxy-5-nitrophenyl)-3-hydroxy-N-ethylacrylamide (176 mg, 0.5 mmol) in DCM (5 mL) was added PCl₅ (104 mg, 0.5 mmol) at 0° C. The resulting suspension was stirred at overnight until all the start materials were consumed detected by LC-MS. Then the reaction mixture was allowed to cool to room temperature and used in the next step without further purification.

Step 3: Synthesis of (Z)-3-amino-2-cyano-3-(3,4-dimethoxy-5-nitrophenyl)-N-ethylacrylamide (5)

A solution of (Z)-3-chloro-2-cyano-3-(3,4-dimethoxy-5-nitrophenyl)-N-ethylacrylamide (150 mg, 0.4 mmol) in DCM was added a saturated solution of NH₃ in ACN at 0° C., and then the reaction solution was stirred at 0° C. continuously until all the starting materials were consumed completely. The reaction was quenched by the addition of H₂O and stirred for 30 min. The aqueous phase was extracted with ethyl acetate. The organic layers were combined, washed with brine and dried with Na₂SO₄. The solvent was eliminated under reduced pressure to give the crude product.

Step 4: Synthesis of (Z)-3-amino-2-cyano-3-(3,4-dihydroxy-5-nitrophenyl)-N-ethylacrylamide (6)

A solution of (Z)-3-amino-2-cyano-3-(3,4-dimethoxy-5-nitrophenyl)-N-ethylacrylamide (67 mg, 0.2 mmol) in DCM (5 mL) was added 1.0 M solution of BBr₃ in DCM (1 mL, 1 mmol) at −15° C. under nitrogen atmosphere. The resulting red suspension was stirred for 1 hour at −15° C. and allowed to warm to room temperature overnight. The reaction was quenched by the addition of H2O (2 mL) and stirred for 30 min. The aqueous phase was extracted with ethyl acetate (30 mL*3). The organic layers were combined, washed with brine and dried with Na₂SO₄. The solvent was eliminated under reduced pressure to give the crude product. Further purification by Prep-HPLC gave the desired product as yellow solid (5 mg, 9%). 1H NMR (400 MHz, DMSO) δ 10.53 (s, 2H), 9.44 (s, 1H), 8.02 (s, 2H), 7.63 (d, J=2.0 Hz, 1H), 7.36 (d, J=2.0 Hz, 1H), 3.32-3.25 (m, 2H), 1.14 (t, J=7.1 Hz, 3H). MS [M+H]⁺ calcd for C₁₂H₁₃N₄O₅ 293.2, found 292.8.

Compound 692N:

692N was prepared in four synthetic steps from 3,4-dimethoxy-5-nitrobenzoic acid, according to the following procedure:

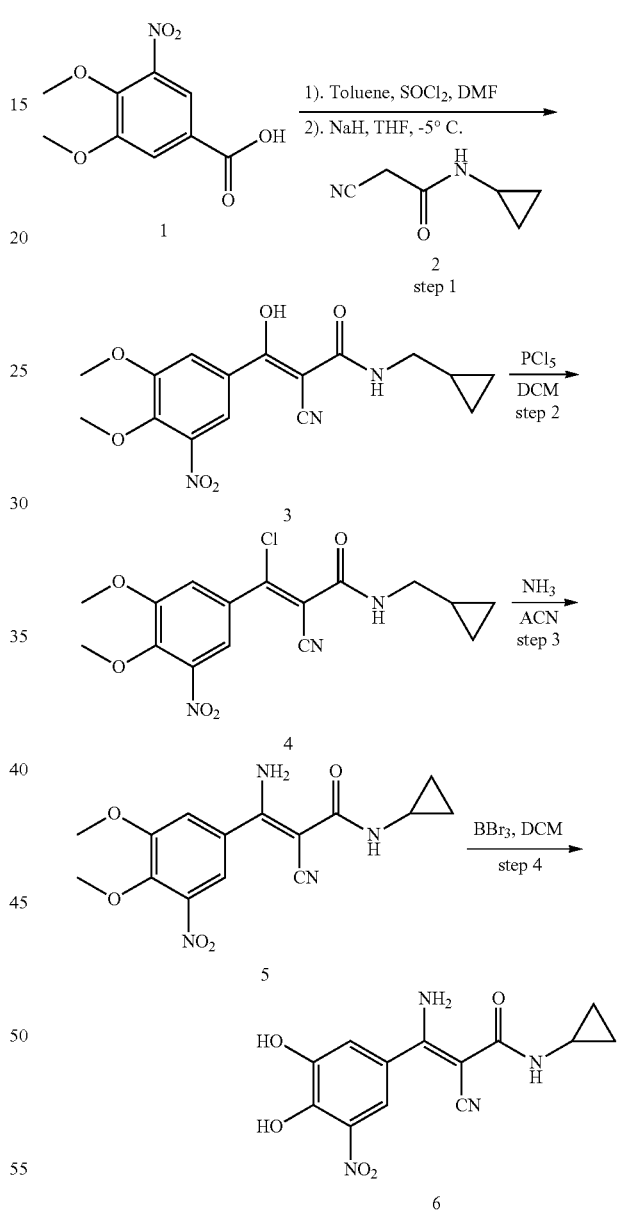

Step 1: Synthesis of (Z)-2-cyano-N-(cyclopropylmethyl)-3-(3,4-dimethoxy-5-nitrophenyl)-3-hydroxyacrylamide (3)

Under a nitrogen atmosphere, SOCl₂ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature.

The mixture was heated at 60° C. and stirred for 15 hours. The organic solvent was eliminated by distillation under reduced pressure. More toluene was added and eliminated again. The resulting yellowish solid 3,4-dimethoxy-5-nitrobenzoyl chloride was dissolved in anhydrous THF (5 mL).

Under a nitrogen atmosphere, 60% NaH (0.18 g, 4.4 mmol) was added to the solution of 2-cyano-N-cyclopropylacetamide (250 mg, 2.0 mmol) in anhydrous THF (5 mL) at −5 OC. The resulting suspension was stirred at −5 OC for 15 min and the solution of 3,4-dimethoxy-5-nitrobenzoyl chloride in THF was added over 10 min and stirred for an additional 1 hour at −5° C. The reaction mixture was warmed to 0° C., quenched by the addition of 1N.HCl solution (4 mL) and stirred for 10 min at room temperature, extracted by ethyl acetate (25 mL*2), the organic layers was dried with $Na_2SO_4$ and concentrated in vacuo to give the title compound 3 as an yellow solid (165 mg, 23%).

Step2: Synthesis of (Z)-3-chloro-2-cyano-N-(cyclopropylmethyl)-3-(3,4-dimethoxy-5-nitrophenyl)acrylamide (4)

A solution of (Z)-2-cyano-3-(3,4-dimethoxy-5-nitrophenyl)-3-hydroxy-N-propylacrylamide (165 mg, 0.5 mmol) in DCM (5 mL) was added $PCl_5$ (104 mg, 0.5 mmol) at 0° C. The resulting suspension was stirred at overnight until all the start materials were consumed detected by LC-MS. Then the reaction mixture was allowed to cool to room temperature and used in the next step without further purification.

Step3: Synthesis of (Z)-3-amino-2-cyano-N-cyclopropyl-3-(3,4-dimethoxy-5-nitrophenyl)acrylamide (5)

A solution of (Z)-3-chloro-2-cyano-N-(cyclopropylmethyl)-3-(3,4-dimethoxy-5-nitrophenyl)acrylamide (164 mg, 0.5 mmol) in DCM was added a saturated solution of $NH_3$ in ACN at 0° C., and then the reaction solution was stirred at 0° C. continuously until all the starting materials were consumed completely. The reaction was quenched by the addition of $H_2O$ and stirred for 30 min. The aqueous phase was extracted with ethyl acetate. The organic layers were combined, washed with brine and dried with $Na_2SO_4$. The solvent was eliminated under reduced pressure to give the crude product which was used in the next step without further purification.

Step4: Synthesis of (Z)-3-amino-2-cyano-N-cyclopropyl-3-(3,4-dihydroxy-5-nitrophenyl)acrylamide (6)

A solution of (Z)-3-amino-2-cyano-N-cyclopropyl-3-(3,4-dimethoxy-5-nitrophenyl)acrylamide (66 mg, 0.2 mmol) in DCM (5 mL) was added 1.0 M solution of $BBr_3$ in DCM (1 mL, 1 mmol) at −15 OC under nitrogen atmosphere. The resulting red suspension was stirred for 1 hour at −15° C. and allowed to warm to room temperature overnight. The reaction was quenched by the addition of $H_2O$ (2 mL) and stirred for 30 min. The aqueous phase was extracted with ethyl acetate (30 mL*3). The organic layers were combined, washed with brine and dried with $Na_2SO_4$. The solvent was eliminated under reduced pressure to give the crude product. Further purification by Prep-HPLC gave the desired product. (7 mg, 12%).1H NMR (400 MHz, DMSO) δ 10.52 (s, 2H), 9.53 (s, 1H), 7.63 (d, J=2.0 Hz, 1H), 7.35 (d, J=2.0 Hz, 1H), 2.61-2.55 (m, 1H), 0.86-0.81 (m, 2H), 0.66-0.61 (m, 2H). MS [M+H]$^+$ calcd for $C_{13}H_{13}N_4O_5$ 305.3, found 304.9

Compound 697N:

697N was prepared in two synthetic steps from (E)-methyl 5-(1-cyano-2-(3,4-dimethoxy-5-nitrophenyl)-2-hydroxyvinyl)pyrazine-2-carboxylate, according to the following procedure:

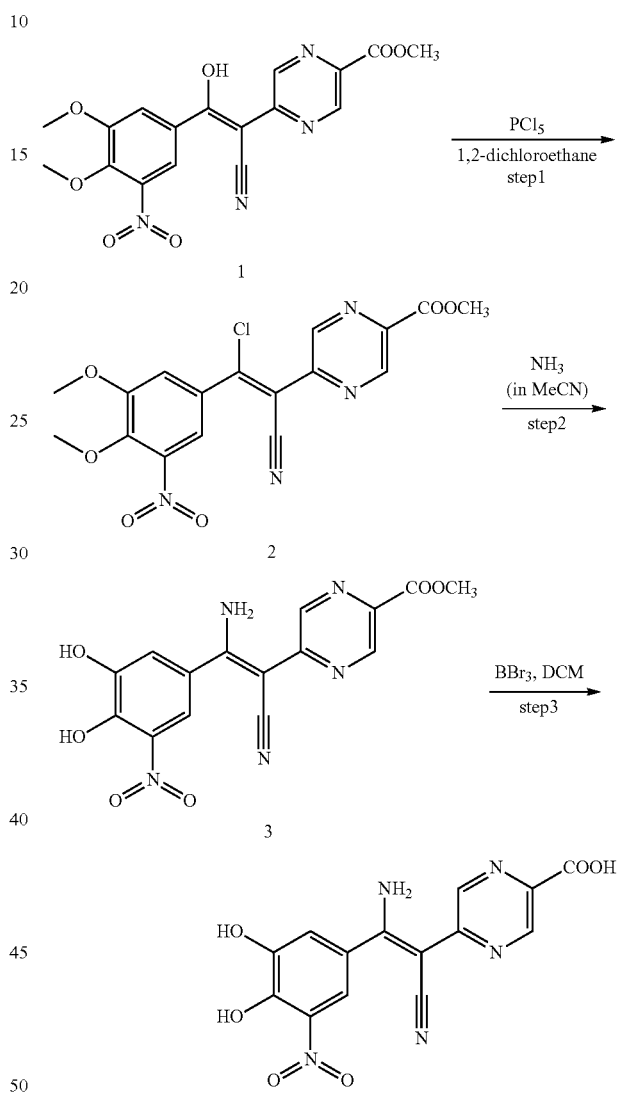

Step1: Synthesis of (E)-methyl 5-(2-chloro-1-cyano-2-(3,4-dimethoxy-5-nitrophenyl)vinyl)pyrazine-2-carboxylate (2)

A solution of (E)-methyl 5-(1-cyano-2-(3,4-dimethoxy-5-nitrophenyl)-2-hydroxyvinyl) pyrazine-2-carboxylate (150 mg, 0.39 mmol) in 1,2-dichloroethane (25 mL) was added $PCl_5$ (83 mg, 0.40 mmol) at 0° C. The resulting suspension was stirred at overnight until all the start materials were consumed detected by LC-MS. Then the reaction mixture was allowed to cool and used in the next step without further purification.

Step2: Synthesis of (E)-methyl 5-(2-amino-1-cyano-2-(3,4-dimethoxy-5-nitrophenyl)vinyl)pyrazine-2-carboxylate (3)

A solution of (E)-methyl 5-(2-chloro-1-cyano-2-(3,4-dimethoxy-5-nitrophenyl)vinyl) pyrazine-2-carboxylate (180 mg, 0.45 mmol) in 1,2-dichloroethane (25 mL) was added a saturated solution of NH$_3$ in ACN at 0° C., and then the reaction solution was stirred at 0° C. continuously until all the starting materials were consumed completely. The reaction was quenched by the addition of H$_2$O and stirred for 30 min. The aqueous phase was extracted with ethyl acetate. The organic layers were combined, washed with brine and dried with Na$_2$SO$_4$. The solvent was eliminated under reduced pressure to give the crude product which was used in the next step without further purification.

Step3: Synthesis of (E)-methyl 5-(2-chloro-1-cyano-2-(3,4-dimethoxy-5-nitrophenyl)vinyl)pyrazine-2-carboxylate (4)

A solution of (E)-methyl 5-(2-amino-1-cyano-2-(3,4-dimethoxy-5-nitrophenyl)vinyl) pyrazine-2-carboxylate (98 mg, 0.25 mmol) in DCM (5 mL) was added 1.0 M solution of BBr$_3$ in DCM (3 mL, 3 mmol) at −15 OC under nitrogen atmosphere. The resulting red suspension was stirred for 1 hour at −15° C. and allowed to warm to room temperature overnight. The reaction was quenched by the addition of H$_2$O (2 mL) and stirred for 30 min. The aqueous phase was extracted with ethyl acetate (30 mL*3). The organic layers were combined, washed with brine and dried with Na$_2$SO$_4$. The solvent was eliminated under reduced pressure to give the crude product. Further purification by Prep-HPLC (0.5% TFA, MeOH/H$_2$O) gave the desired product as yellow solid (11 mg, 13%).1H NMR (400 MHz, DMSO) δ 10.96-11.2 (m, 1H), 10.42 (s, 1H), 8.94 (s, 1H), 8.66 (s, 1H), 7.76 (s, 1H), 6.79 (s, 1H). MS [M+H]$^+$ calcd for C$_{14}$H$_9$N$_5$O$_6$ 344.0, found 344.0

Compound 701N:

701N was prepared in four synthetic steps from 3,4-dimethoxy-5-nitrobenzoic acid, according to the following procedure:

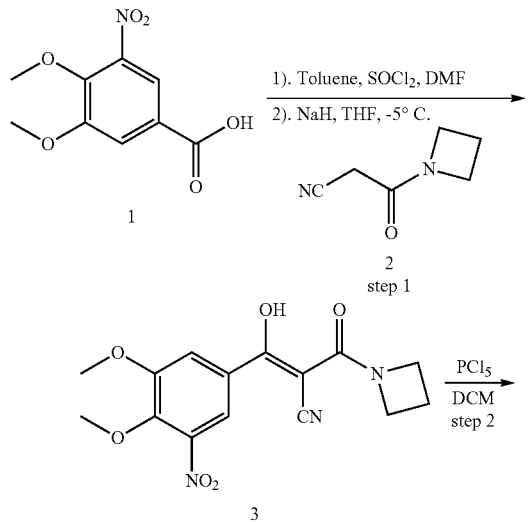

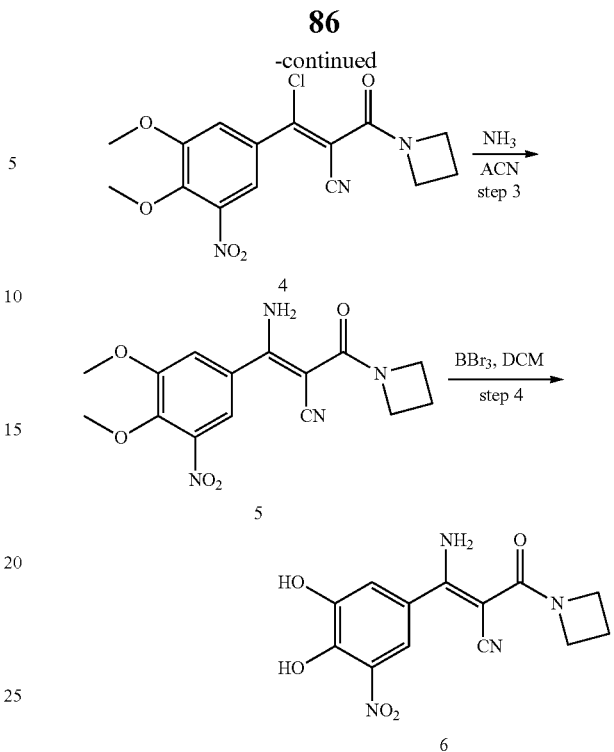

Step1: Synthesis of (Z)-2-(azetidine-1-carbonyl)-3-(3,4-dimethoxy-5-nitrophenyl)-3-hydroxyacrylonitrile (3)

Under a nitrogen atmosphere, SOCl$_2$ (0.38 mL, 5.28 mmol) and anhydrous DMF (0.01 mL, 0.22 mmol) were added to a suspension of 3,4-dimethoxy-5-nitrobenzoic acid (500 mg, 2.2 mmol) in toluene (10 mL) at room temperature. The mixture was heated at 60° C. and stirred for 15 hours. The organic solvent was eliminated by distillation under reduced pressure. More toluene was added and eliminated again. The resulting yellowish solid 3,4-dimethoxy-5-nitrobenzoyl chloride was dissolved in anhydrous THF (5 mL).

Under a nitrogen atmosphere, 60% NaH (0.18 g, 4.4 mmol) was added to the solution of 3-(azetidin-1-yl)-3-oxopropanenitrile (250 mg, 2.0 mmol) in anhydrous THF (5 mL) at −5 OC. The resulting suspension was stirred at −5 OC for 15 min and the solution of 3,4-dimethoxy-5-nitrobenzoyl chloride in THF was added over 10 min and stirred for an additional 1 hour at −5° C. The reaction mixture was warmed to 0° C., quenched by the addition of 1N.HCl solution (4 mL) and stirred for 10 min at room temperature, extracted by ethyl acetate (25 mL*2), the organic layers was dried with Na$_2$SO$_4$ and concentrated in vacuo to give the compound 3.

Step2: Synthesis of (Z)-2-(azetidine-1-carbonyl)-3-chloro-3-(3,4-dimethoxy-5-nitrophenyl)acrylonitrile (4)

A solution of (Z)-2-(azetidine-1-carbonyl)-3-(3,4-dimethoxy-5-nitrophenyl)-3-hydroxyacrylonitrile (175 mg, 0.5 mmol) in DCM (5 mL) was added PCl$_5$ (104 mg, 0.5 mmol) at 0° C. The resulting suspension was stirred at overnight until all the start materials were consumed detected by LC-MS. Then the reaction mixture was allowed to cool to room temperature and used in the next step without further purification.

Step3: Synthesis of (Z)-3-amino-2-(azetidine-1-carbonyl)-3-(3,4-dimethoxy-5-nitrophenyl)acrylonitrile (5)

A solution of (Z)-2-(azetidine-1-carbonyl)-3-chloro-3-(3,4-dimethoxy-5-nitrophenyl)acrylonitrile (164 mg, 0.5 mmol) in DCM was added a saturated solution of NH₃ in ACN at 0° C., and then the reaction solution was stirred at 0° C. continuously until all the starting materials were consumed completely. The reaction was quenched by the addition of H₂O and stirred for 30 min. The aqueous phase was extracted with ethyl acetate. The organic layers were combined, washed with brine and dried with Na₂SO₄. The solvent was eliminated under reduced pressure to give the crude product which was used in the next step without further purification.

Step4: Synthesis of (Z)-3-amino-2-(azetidine-1-carbonyl)-3-(3,4-dihydroxy-5-nitrophenyl)acrylonitrile (6)

A solution of (Z)-3-amino-2-(azetidine-1-carbonyl)-3-(3,4-dimethoxy-5-nitrophenyl)acrylonitrile (66 mg, 0.2 mmol) in DCM (5 mL) was added 1.0 M solution of BBr₃ in DCM (1 mL, 1 mmol) at −15 OC under nitrogen atmosphere. The resulting red suspension was stirred for 1 hour at −15° C. and allowed to warm to room temperature overnight. The reaction was quenched by the addition of H₂O (2 mL) and stirred for 30 min. The aqueous phase was extracted with ethyl acetate (30 mL*3). The organic layers were combined, washed with brine and dried with Na₂SO₄. The solvent was eliminated under reduced pressure to give the crude product. Further purification by Prep-HPLC gave the desired product (7 mg, 12%). 1H NMR (400 MHz, DMSO) δ 10.52 (s, 2H), 9.87 (s, 1H), 7.60 (d, J=2.1 Hz, 1H), 7.35 (d, J=2.1 Hz, 1H), 4.26 (s, 4H), 2.29 (m, 2H). MS [M+H]⁺ calcd for C₁₃H₁₃N₄O₅ 305.3, found 305.0

Compound 711N:

711N was prepared in three synthetic steps from (Z)-3-(3,4-dimethoxy-5-nitrophenyl)-3-hydroxy-2-(thiazole-4-carbonyl)acrylonitrile, according to the following procedure:

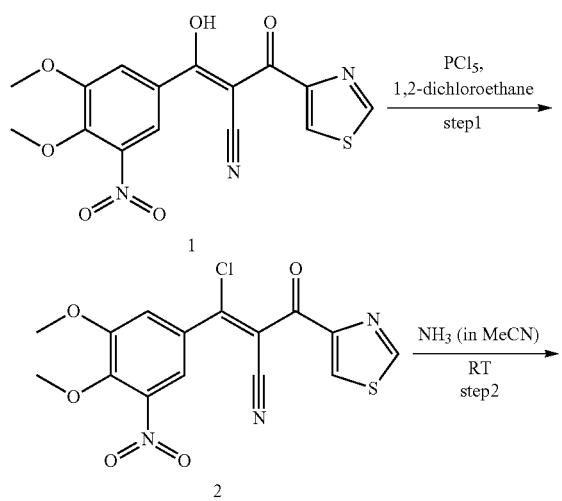

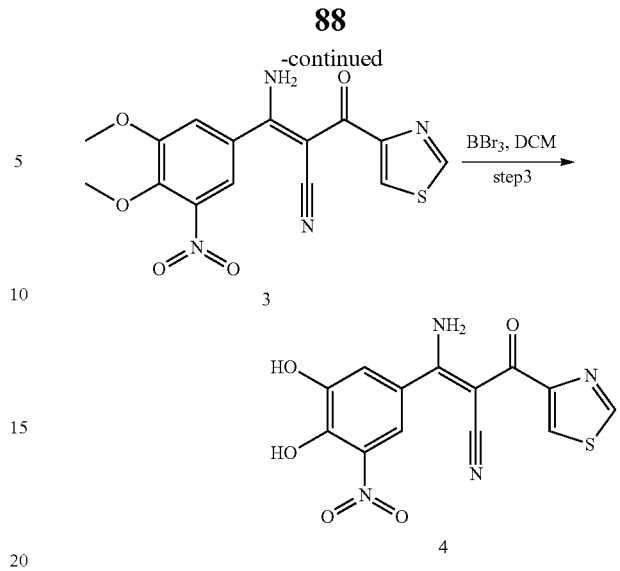

Step1: Synthesis of (Z)-3-chloro-3-(3,4-dimethoxy-5-nitrophenyl)-2-(thiazole-4-carbonyl)acrylonitrile (2)

A solution of (Z)-3-(3,4-dimethoxy-5-nitrophenyl)-3-hydroxy-2-(thiazole-4-carbonyl)acrylonitrile (150 mg, 0.42 mmol) in 1,2-dichloroethane (25 mL) was added PCl₅ (86 mg, 0.42 mmol) at 0° C. The resulting suspension was stirred at overnight until all the start materials were consumed detected by LC-MS. Then the reaction mixture was allowed to cool to room temperature and used in the next step without further purification.

Step2: Synthesis of (Z)-3-amino-3-(3,4-dimethoxy-5-nitrophenyl)-2-(thiazole-4-carbonyl)acrylonitrile (3)

A solution of (Z)-3-chloro-3-(3,4-dimethoxy-5-nitrophenyl)-2-(thiazole-4-carbonyl)acrylonitrile (185 mg, 0.42 mmol) in 1,2-dichloroethane (25 mL) was added a saturated solution of NH₃ in ACN at 0° C., and then the reaction solution was stirred at 0° C. continuously until all the starting materials were consumed completely. The reaction was quenched by the addition of H₂O and stirred for 30 min. The aqueous phase was extracted with ethyl acetate. The organic layers were combined, washed with brine and dried with Na₂SO₄. The solvent was eliminated under reduced pressure to give the crude product which was used in the next step without further purification. MS [M+H]⁺ calcd for C₁₅H₁₂N₄O₅S 361.0, found 361.0

Step3: Synthesis of ammonium (Z)-5-(1-amino-2-cyano-3-oxo-3-(thiazol-4-yl)prop-1-enyl)-2-hydroxy-3-nitrophenolate (4)

A solution of (Z)-3-amino-3-(3,4-dimethoxy-5-nitrophenyl)-2-(thiazole-4-carbonyl)acrylonitrile (100 mg, 0.28 mmol) in DCM (5 mL) was added 1.0 M solution of BBr₃ in DCM (1 mL, 1 mmol) at −15 OC under nitrogen atmosphere. The resulting red suspension was stirred for 1 hour at −15° C. and allowed to warm to room temperature overnight. The reaction was quenched by the addition of 0.5 N.NH₄OH (2 mL) and stirred for 5 min. The aqueous phase was washed with ethyl acetate. The hydrous layer was eliminated under reduced pressure to give the crude product.

Further purification by Prep-HPLC (0.05% FA, MeOH/H$_2$O) gave the desired product as yellow solid (11 mg, 15%). 1H NMR (400 MHz, DMSO) δ 8.85 (s, 1H), 7.66 (s, 1H), 7.38 (s, 1H), 6.80-6.99 (m, 1H), 6.66-6.74 (m, 1H). MS [M+H]$^+$ calcd for C$_{13}$H$_{11}$N$_5$O$_5$S 333.0, found 333.0

Compound 347M:

347M was prepared in three synthetic steps from 2-cyano-3-(3,4-dimethoxy-5-nitrophenyl)-N,N-diethyl-3-hydroxyacrylamide according to the following procedure:

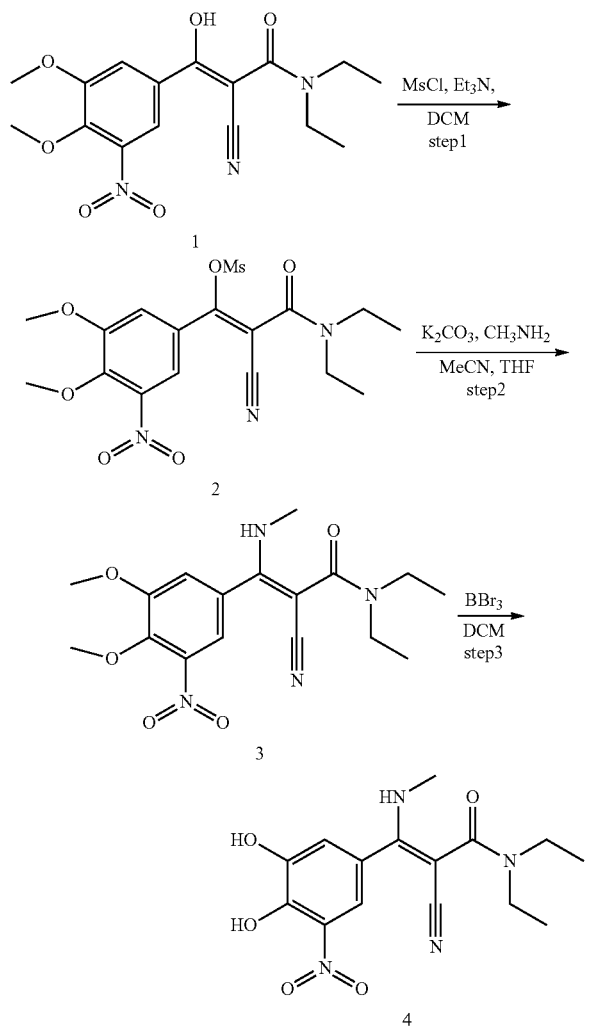

Step1: Synthesis of 2-cyano-3-(diethylamino)-1-(3,4-dimethoxy-5-nitrophenyl)-3-oxoprop-1-enyl methanesulfonate (2)

A solution of 2-cyano-3-(3,4-dimethoxy-5-nitrophenyl)-N,N-diethyl-3-hydroxyacrylamide (350 mg, 1 mmol) and Et$_3$N (202 mg, 2 mmol) in DCM (15 mL) was added MsCl (250 mg, 2 mmol) at 0° C. The reaction solution was stirred at rt for 3 h, then it was concentrated in vacuo to afford the crude product (360 mg), which was used in the next step without further purification.

Step2: Synthesis of 2-cyano-3-(3,4-dimethoxy-5-nitrophenyl)-N,N-diethyl-3-(methylamino)acrylamide (3)

A solution of 2-cyano-3-(diethylamino)-1-(3,4-dimethoxy-5-nitrophenyl)-3-oxoprop-1-enyl methanesulfonate (250 mg, 0.7 mmol) and K$_2$CO$_3$ (193 mg, 1.4 mmol) in MeCN (10 mL) was added MeNH$_2$ (1.4 mmol, 0.7 mL, 2N in THF) at rt. The reaction solution was refluxed for 2 h, and then 50 mL of water was added. The aqueous phase was extracted by EA for two times (50 mL×2), and then the organic layer was concentrated in vacuo to afford the crude product (210 mg), which was used in the next step without further purification. MS [M+H]$^+$ calcd for C$_{17}$H$_{22}$N$_4$O$_5$ 363.1., found 363.1.

Step3: Synthesis of 2-cyano-3-(3,4-dihydroxy-5-nitrophenyl)-N,N-diethyl-3-(methylamino)acrylamide (4)

A solution of 2-cyano-3-(3,4-dimethoxy-5-nitrophenyl)-N,N-diethyl-3-(methylamino)acrylamide (210 mg, 0.58 mmol) in DCM (5 mL) was added 1.0 M solution of BBr$_3$ in DCM (2 mL, 2 mmol) at −15° C. under nitrogen atmosphere. The reaction solution was stirred at −15° C. for 1 h then at room temperature overnight. The reaction was quenched by the addition of H$_2$O (2 mL) and stirred for 30 min. The aqueous phase was extracted by ethyl acetate for three times (30 mL×3). The organic layer was washed with brine and dried over Na$_2$SO$_4$, then it was concentrated in vacuo to afford the crude product, which was purified by Prep-HPLC (0.5% TFA, MeOH/H$_2$O) to gain the desired product as bright yellow solid (25 mg, 13%). MS $^1$H NMR (400 MHz, DMSO) δ 10.69 (s, 2H), 7.43 (s, 1H), 7.20 (s, 1H), 3.40-3.43 (m, 4H), 2.69 (d, J=4.9 Hz, 3H), 1.14 (t, J=6.8 Hz, 13H), 1.14 (t, J=6.8 Hz, 3H). [M+H]$^+$ calcd for C$_{12}$H$_7$N$_5$O$_6$S 350.0, found 350.0.

Enzymatic Inhibition.

We measured compound inhibition activity in a demethylation reaction catalyzed by FTO (US2014/0148383A1). The reaction system was incubated at 37° C. for 2 h and stopped by heating at 95° C. for 5 min. ssDNA was digested by nuclease P1 and alkaline phosphatase. The concentrations of N$^6$-mA and A were analyzed by HPLC-MS/MS. When concentration of substrate and enzyme are 0.5 μM and 0.1 μM, respectively, the measured IC$_{50}$ value of entacapone against FTO is ~3 μM. The compounds of Tables 1-3 were consistently active, with IC$_{50}$'s less than 10 NM, and most less than 1 μM.

Exemplary IC50 Data of Submicromolar Representative Compounds

| Compound No. | Enzymatic inhibition (IC50) μM |
| --- | --- |
| 687 | <1 |
| 317 | >1 |
| 371 | ~1 |
| 660 | <1 |
| 382 | >1 |
| 702 | ~1 |
| 698 | >1 |
| 675 | >1 |
| 394 | >1 |
| 664 | ~1 |
| 684 | >1 |
| 688 | >1 |
| 713 | <1 |
| 709 | <1 |

-continued

| Compound No. | Enzymatic inhibition (IC50) μM |
|---|---|
| 712 | ~1 |
| 693 | ~1 |
| 331 | ~1 |
| 333 | >1 |
| 318 | ~1 |
| 365 | ~1 |
| 366 | >1 |
| 390 | ~1 |
| 656 | <1 |
| 666 | <1 |
| 315 | ~1 |
| 319 | <1 |
| 389 | ~1 |
| 502 | <1 |
| 505 | <1 |
| 395 | <1 |
| 396 | <1 |
| 522 | ~1 |
| 655 | <1 |
| 518 | >1 |
| 520 | <1 |
| 347 | <1 |
| 351 | <1 |
| 523 | <1 |
| 524 | ~1 |
| 525 | <1 |
| 503 | ~1 |
| 359 | >1 |
| 374 | <1 |
| 668 | <1 |
| 661 | ~1 |
| 673 | <1 |
| 674 | >1 |
| 691 | <1 |
| 692 | <1 |
| 697 | <1 |
| 701 | <1 |
| 711 | ~1 |
| 715 | <1 |
| 722 | <1 |
| 347N | <1 |
| 661N | <1 |
| 691N | ~1 |
| 692N | >1 |
| 697N | <1 |
| 701N | >1 |
| 711N | >1 |
| 347M | ~1 |

In Vivo Anti-Obesity Efficacy.

Male wistar rats (6 weeks) were fed with high-fat diet (45% fat, OpenSource Diets D12451), and compound (100 mg/kg) was administered to 12 randomly selected rats by gavage. After 8 weeks, the mean body weight of drug treatment group was less than that of control group. However, the body-weight-normalized food intakes of the two groups showed no difference. The LDL-c (Low Density Lipoprotein-cholesterol) in serum of drug treatment group was reduced compared to that of control group, and the adipose and hepatic tissues of rat in drug-treated groups showed reduced size of adipose cells and reduced level of liver steatosis.

Atherosclerosis Model: Ldlr-Deficient Mice.

We measured compound anti-atherosclerosis efficacy using Ldlr$^{-/-}$ mice fed western style diet (20% fat, 0.15% cholesterol), compound (100 mg/day) was orally administered by blending with diet. After 8 weeks, the mean lesion area in aortic sinuses of drug treatment group was less than that of the control group.

In Vivo Anti-Obesity Efficacy in Obese Mice.

Male C57BL/6 mice were fed with high-fat diet (45% fat, OpenSource Diets D12451) for 8 weeks. Then obese mice with body weight 20% larger than that of mice fed with normal diet (20 mice) were selected for experiments. Compound (100 mg/kg) was orally administered to 10 randomly selected obese mice by blending with diet. After 13 weeks, the mean body weight gain of drug treatment group was about less than that of the control group.

In Vivo Anti-Diabetic Efficacy in Genetically Diabetic Db/Db Mice.

Compound (100 mg/kg) was orally administered to 11 randomly selected male db/db mice by blending with normal diet, while the other 9 male db/db mice fed with normal diet as control group. After 20 weeks, the mean fasting plasma glucose of drug treatment group was significantly lower than that of control group (*p-value <0.05).

From our results herein and further data we determine that preferred anti-weight gain, anti-obesity and anti-obesity related disease, such as anti-diabetes, effective human dosages of the compounds should be 0.1-10, 0.5-10, 0.5-5, 0.5-2.5, 0.5-1, 1-10, 1-5, 1-2.5, 2-10, or 2-5 g/day.

COMT Inhibition Assay.

We measured compound COMT inhibitory activity by reaction kinetic model. The test article was diluted with assay buffer to desired concentration. The COMT enzyme was also diluted with assay buffer. Then 5 μL diluted test article, 5 μL diluted COMT and 5 μL Esculetin were added into plate and incubated for 5 min at 37° C., sealed with TopSeal-A 384, Clear Adhesive (PE). Then 5 μL AdoMet was added into the plate. The reaction system contains 1U COMT enzyme, test article, 4 μM Esculetin, 0.6 mM AdoMet, 50 mM $K_3PO_4$, and 10 mM $MgCl_2$. Read plate by using kinetics model (Excitation at 360 nm & emission at 460 nm). The inhibition was calculated from the slope.

Rat Liver Microsome Stability Assay.

Compound stability was tested in rat liver microsome. Microsome working solution contains rat liver microsome 1 mg/ml, test compound 2 μM, NADPH 1 mM in 0.05 M Phosphate buffer (pH=7.4). This reaction system was incubated at 37° C. At each time point of 0, 5, 15, 30 and 60 min, an aliquot of 15 μL was transferred into another tube with 200 μL quenching solution (Internal standard (Terfenadine) 5 ng/ml in Methanol). Vortex, Centrifuge at 3,500 rpm for 12 min, Transfer 100 μL of supernatant to 96 well plate for LC-MS/MS analysis and dilute sample with MeOH:H2O (1:1) if necessary.

Result of Selectivity and Rat Liver Microsome

| Compound | FTO (μM) | COMT (μM) | Selectivity Index* | Rat Liver Microsome | |
|---|---|---|---|---|---|
| | | | | $T^{1/2}$ (min) | CLint (μL/min/ mg protein) |
| Entacapone | 3 | 0.06 | 1.00 | 39.2 | 17.7 |
| 347 | 0.5 | 0.551 | 55.10 | 6931 | 0.100 |
| 315 | 1 | 70% at 200 nM; 19% at 50 nM | | 2.24 | 310 |
| 351 | 0.75 | 80% at 200 nM; 33% at 50 nM | | 77.0 | 9.00 |
| 396 | 0.25 | 0.108 | 21.60 | 33.2 | 20.9 |
| 523 | 0.5 | 0.105 | 10.50 | 239 | 2.90 |
| 395 | 0.5 | 74% at 200 nM; 36% at 50 nM | | 55.0 | 12.6 |
| 525 | 0.5 | 74% at 200 nM; 39% at 50 nM | | 63.6 | 10.9 |
| 390 | 1 | 36% at 200 nM; 12% at 50 nM | | 2.61 | 266 |
| 503 | 1.5 | 24% at 200 nM; 9% at 50 nM | | 1386 | 0.50 |

-continued

| Compound | FTO (μM) | COMT (μM) | Selectivity Index* | Rat Liver Microsome T½ (min) | CLint (μL/min/ mg protein) |
|---|---|---|---|---|---|
| 331 | 1 | 54% at 200 nM; 25% at 50 nM | | 93.7 | 7.40 |
| 374 | 0.5 | 0.065 | 6.50 | 1155 | 0.600 |
| 371 | 1 | 71% at 200 nM; 33% at 50 nM | | 16.1 | 43.0 |
| 661 | 1 | 26% at 200 nM; 12% at 50 nM | | 315 | 2.20 |
| 655 | 0.3 | 0.024 | 4.00 | 433 | 1.60 |
| 697 | 0.75 | 33% at 200 nM; −3 at 50 nM | | 630 | 1.10 |
| 687 | 1 | 0.033 | E65 | 2.44 | 284 |
| 701 | 0.75 | 3.56 | 237.33 | NA | NA |
| Entacapone | 3 | 0.06 | 1.00 | 39.2 | 17.7 |
| 347N | 0.5 | 0.214 | 21.40 | 141 | 4.90 |
| 371 | 1 | 71% at 200 nM; 33% at 50 nM | | 16.1 | 43.0 |
| 661N | 0.75 | 64% at 200 nM; 35% at 50 nM | | 67.3 | 10.3 |
| Entacapone | 3 | 0.06 | 1.00 | 39.2 | 17.7 |
| 347M | 1 | 0.162 | 8.10 | 56.8 | 12.2 |

*Selectivity Index is the normalized COMT/FTO value based on Entacapone's value and was calculated as the following equation: $(COMT_{compound}/FTO_{compound})/(COMT_{entacapone}/FTO_{entacapone})$ It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A pharmaceutical composition comprising an FTO inhibitor selected from a compound formula I, a stereoisomer thereof, a hydrate thereof, and a pharmaceutically-acceptable salt thereof, and a pharmaceutically-acceptable excipient, formulated in an orally-administrable unit dosage form selected from a pill, tablet, capsule, and lozenge, and suitable for administration to a person in need thereof, the inhibitor of structure:

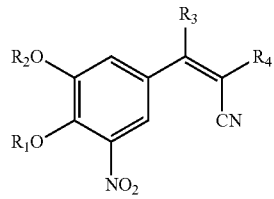

I wherein:
(a)
R1 and R2 are independently H or Me;
R3 is OH or NHR, wherein R is H or an optionally substituted, optionally hetero-, optionally cyclic C1-C18 hydrocarbyl; and
R4 is optionally substituted, optionally hetero-, optionally cyclic C1-C18 hydrocarbyl;
(b)
R1 and R2 are independently H or Me;
R3 is OH or NHR, wherein R is H or C1-C4 alkyl;
R4 is CONHR5; and
R5 is optionally substituted, optionally hetero-, optionally cyclic C1-C18 hydrocarbyl;
(c)
R1 and R2 are independently H or Me;
R3 is OH or NHR, wherein R is H or C1-C4 alkyl;
R4 is COR5; and
R5 is optionally substituted, heterocyclic C3-C18 hydrocarbyl comprising an n-membered ring wherein n=3-18, including 1 to n-1 heteroatoms independently selected from N, O, S and P; or
(d)
R1 and R2 are independently H or Me;
R3 is OH or NHR, wherein R is H or C1-C4 alkyl; and
R4 is optionally substituted, heterocyclic C3-C18 hydrocarbyl comprising an n-membered ring wherein n=3-18, including 1 to n-1 heteroatoms independently selected from N, O, S and P.

2. The composition of claim 1, wherein the FTO inhibitor is a compound of formula:

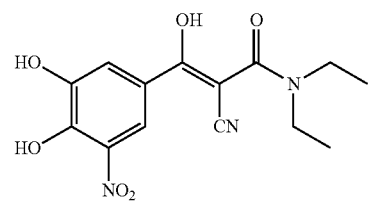

347

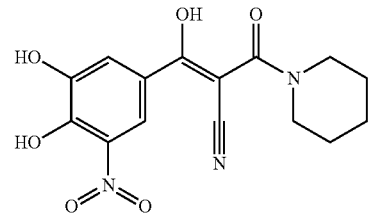

661

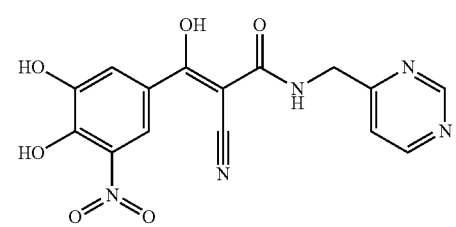

673

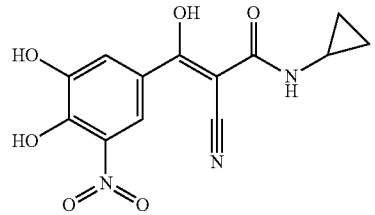

692

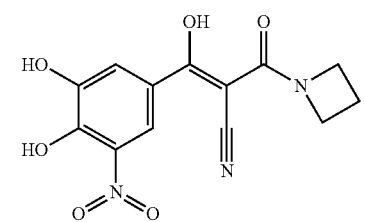 [SMILES: N#C/C(C(=O)N1CCC1)=C(/O)c1cc(O)c(O)c([N+](=O)[O-])c1]

701

-continued

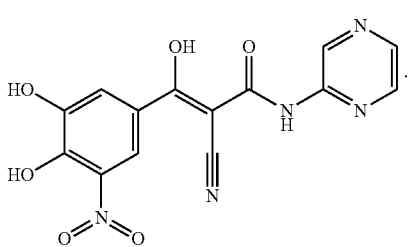
722

3. The composition of claim 1, wherein the FTO inhibitor is a compound of formula:

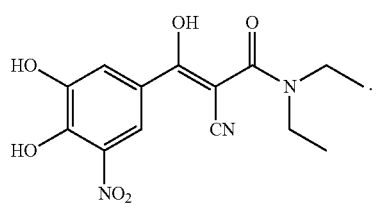
347

4. The composition of claim 1 wherein:
R1 and R2 are independently H or Me;
R3 is OH or NHR, wherein R is H or C1-C4 alkyl; and
R4 is optionally substituted, heterocyclic C3-C18 hydrocarbyl comprising an n-membered ring wherein n=3-18, including 1 to n-1 heteroatoms independently selected from N, O, S and P.

5. The composition of claim 4 wherein the heterocyclic C3-C18 hydrocarbyl is:
a 3 membered ring that is an optionally substituted aziridine, oxirane or oxaziridine;
a 4 membered ring that is an optionally substituted azetidine, oxetane or oxazetidine;
a 5 membered ring that is an optionally substituted pyrrole, 1,2-diazole (pyrazole), 1,3 diazole (imidazole), thiazole, isothiazole, oxazole, isoxazole, furan, dioxole or thiophene;
a 6 membered ring that is an optionally substituted pyridine, diazine, triazine, oxazine, thiazine, dioxine, oxathiine or dithiine;
a 9 membered ring that is an optionally substituted indole, benzothiazole, benzooxazole, benzofuran, benzodioxole, benzothiophene or benzodithiole; or a 10 membered ring that is an optionally substituted quinoline, quinoxaline, quinazoline, chromene, benzodioxine, thiochromene or benzodithiine.

6. The composition of claim 4 wherein the heterocyclic C3-C18 hydrocarbyl is:
a 4 membered ring that is an optionally substituted azetidine, oxetane or oxazetidine.

7. The composition of claim 4 wherein the heterocyclic C3-C18 hydrocarbyl is:
a 5 membered ring that is an optionally substituted pyrrole, 1,2-diazole (pyrazole), 1,3 diazole (imidazole), thiazole, isothiazole, oxazole, isoxazole, furan, dioxole or thiophene.

8. The composition of claim 4 wherein the heterocyclic C3-C18 hydrocarbyl is:
a 5 membered ring that is an optionally substituted thiazole or thiadiazole.

9. The composition of claim 4 wherein the heterocyclic C3-C18 hydrocarbyl is:
a 6 membered ring that is an optionally substituted pyridine, diazine, triazine, oxazine, thiazine, dioxine, oxathiine or dithiine.

10. The composition of claim 4 wherein the heterocyclic C3-C18 hydrocarbyl is:
a 6 membered ring that is an optionally substituted pyridine, diazine, or triazine.

11. The composition of claim 4 wherein the heterocyclic C3-C18 hydrocarbyl is:
a 9 membered ring that is an optionally substituted indole, benzothiazole, benzooxazole, benzofuran, benzodioxole, benzothiophene or benzodithiole.

12. The composition of claim 4 wherein the heterocyclic C3-C18 hydrocarbyl is:
a 9 membered ring that is an optionally substituted benzothiazole.

13. The composition of claim 1 wherein: R3 is OH.

14. A pharmaceutical composition comprising an FTO inhibitor, a stereoisomer thereof, a hydrate thereof, and a pharmaceutically-acceptable salt thereof, and a pharmaceutically-acceptable excipient, formulated in an orally-administrable unit dosage form selected from a pill, tablet, capsule, and lozenge, and suitable for administration to a person in need thereof, wherein the FTO inhibitor is a compound of formula:

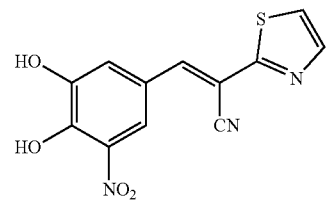 [SMILES: N#C/C(=C\c1cc(O)c(O)c([N+](=O)[O-])c1)c1nccs1]
390

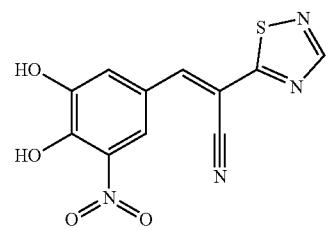 [SMILES: N#C/C(=C\c1cc(O)c(O)c([N+](=O)[O-])c1)c1ncns1]
656

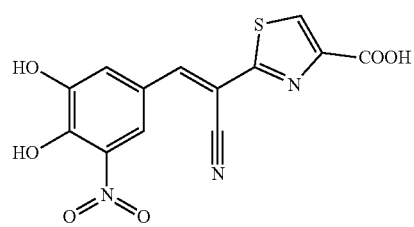 [SMILES: N#C/C(=C\c1cc(O)c(O)c([N+](=O)[O-])c1)c1nc(C(=O)O)cs1]
666

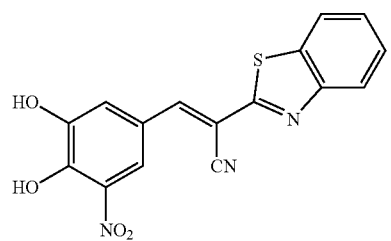 [SMILES: N#C/C(=C\c1cc(O)c(O)c([N+](=O)[O-])c1)c1nc2ccccc2s1]
829

315
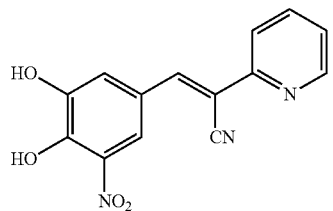 [SMILES: N#C/C(=C\c1cc(O)c(O)c([N+](=O)[O-])c1)c1ccccn1]
400
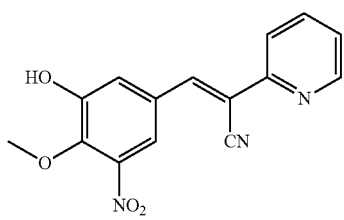 [SMILES: COc1c(O)cc(/C=C(\C#N)c2ccccn2)cc1[N+](=O)[O-]]
319
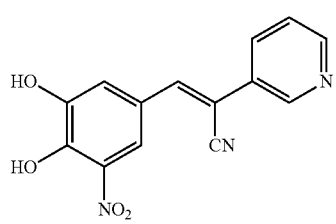
389
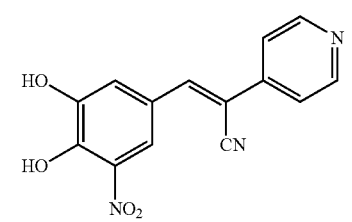
502
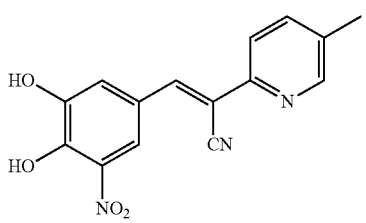 [SMILES: Cc1ccc(/C(C#N)=C/c2cc(O)c(O)c([N+](=O)[O-])c2)nc1]
505
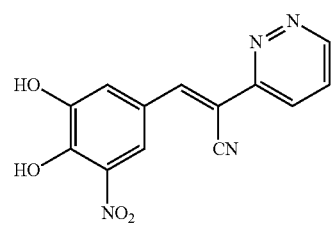 [SMILES: N#C/C(=C\c1cc(O)c(O)c([N+](=O)[O-])c1)c1cccnn1]
395
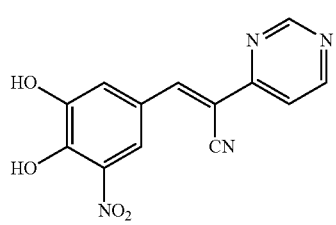 [SMILES: N#C/C(=C\c1cc(O)c(O)c([N+](=O)[O-])c1)c1ccncn1]
396
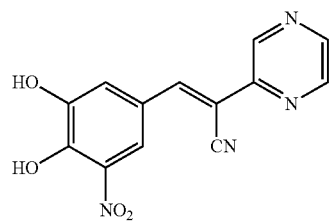
522
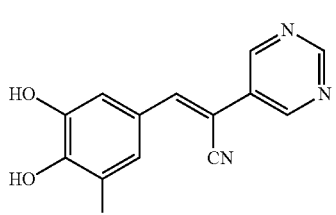
655
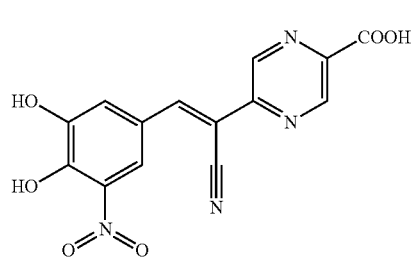
830
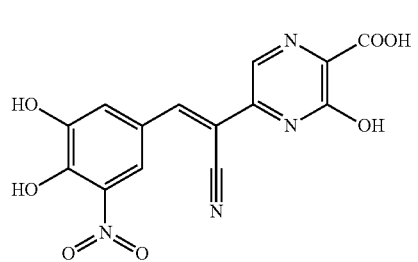
831
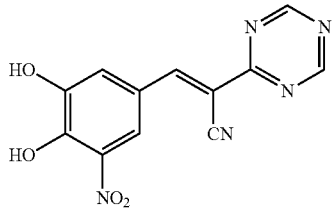
518
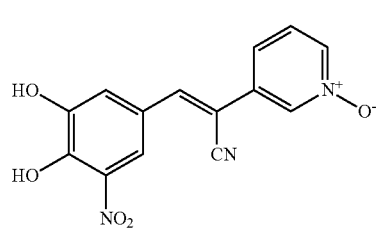 [SMILES: N#C/C(=C\c1cc(O)c(O)c([N+](=O)[O-])c1)c1ccc[n+]([O-])c1]

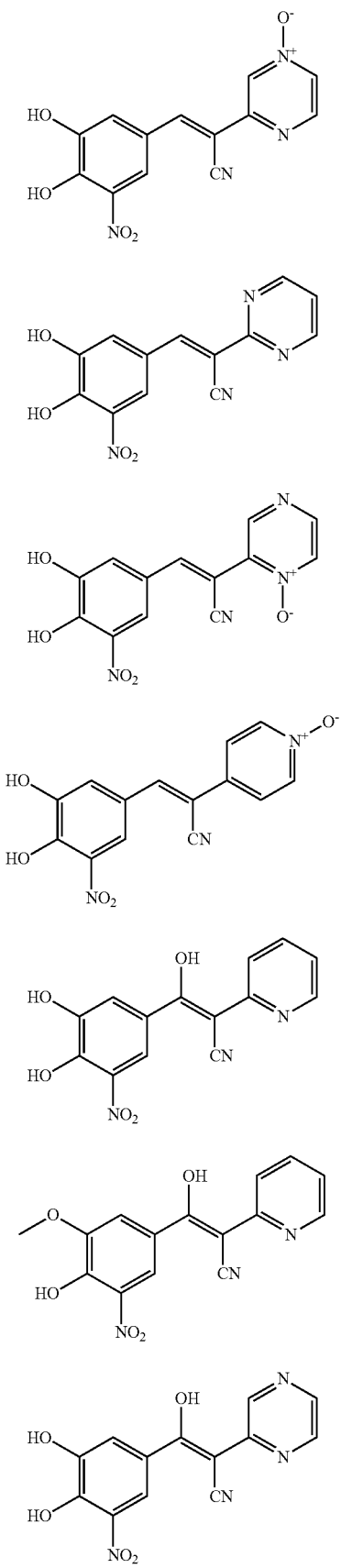

-continued
523N 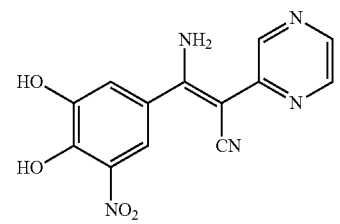
524N 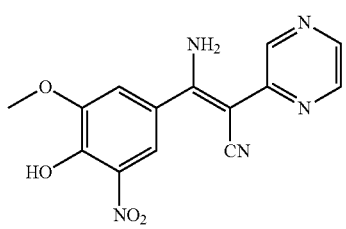 [SMILES: COc1cc(/C(O)=C(\C#N)c2cnccn2)cc([N+](=O)[O-])c1O]
525N 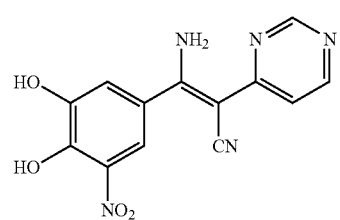 [SMILES: N#C/C(=C(/N)c1cc(O)c(O)c([N+](=O)[O-])c1)c1ccncn1]
503N 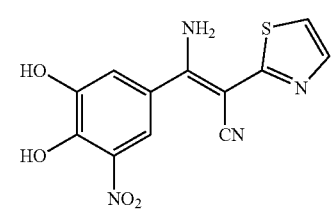 [SMILES: N#C/C(=C(/N)c1cc(O)c(O)c([N+](=O)[O-])c1)c1nccs1]
359N 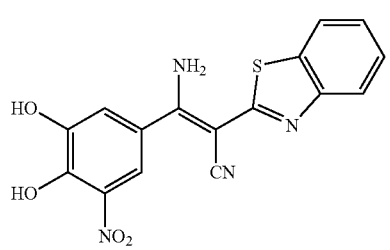
697N 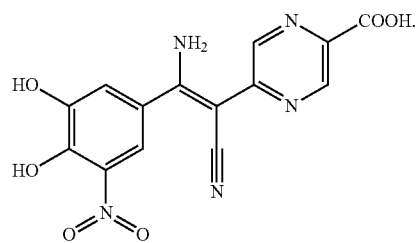
15. The composition of claim 14, wherein the FTO inhibitor is a compound of formula:
351 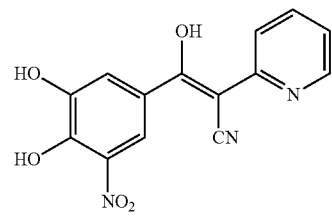
352 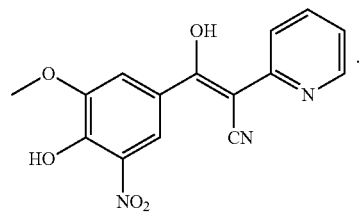
16. The composition of claim 14, wherein the FTO inhibitor is a compound of formula:
523 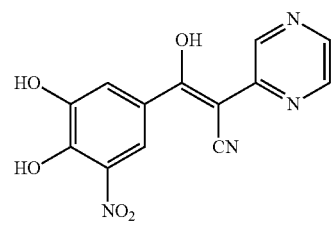
524 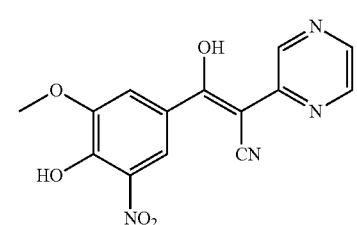
525 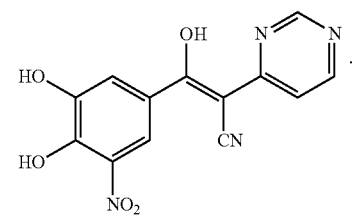
17. The composition of claim 14, wherein the FTO inhibitor is a compound of formula:
502 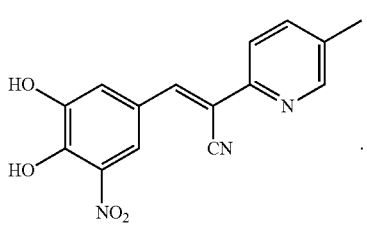

18. The composition of claim 14, wherein the FTO inhibitor is a compound of formula:

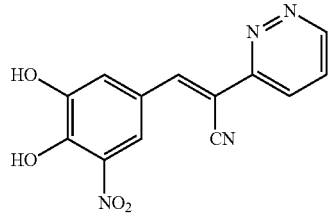
505

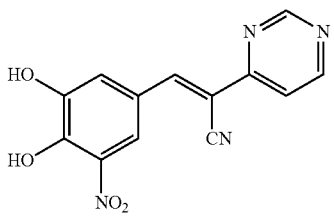
395

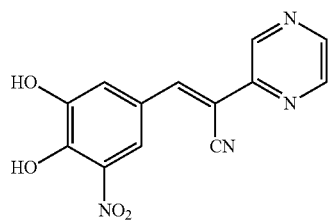
396

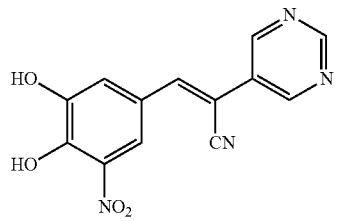
522

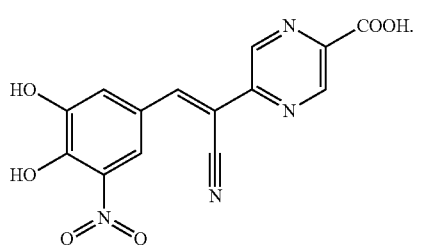
655

19. The composition of claim 14, wherein the FTO inhibitor is a compound of formula:

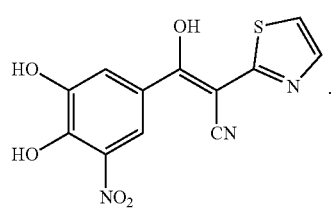
503

20. A method comprising administering to a person in need thereof a composition of claim 1 to inhibit FTO, inhibit weight gain, promote weight loss, reduce serum LDL, cholesterol, LDL-c, or triglycerides, or treat obesity or an obesity related disease or Alzheimer's disease.

* * * * *